(12) United States Patent
Pastor Fernández et al.

(10) Patent No.: US 8,815,918 B2
(45) Date of Patent: Aug. 26, 2014

(54) IMIDAZO [2, 1-B] [1, 3, 4] THIADIAZOLE DERIVATIVES

(75) Inventors: Joaquin Pastor Fernández, Madrid (ES); Guido Kurz, Madrid (ES); Sonia Martinez Gonzalez, Madrid (ES)

(73) Assignee: Centro Nacional de Investigaciones Oncologicas (CNIO), Madrid (ES)

( * ) Notice: Subject to any disclaimer, the term of this patent is extended or adjusted under 35 U.S.C. 154(b) by 0 days.

(21) Appl. No.: 13/262,183

(22) PCT Filed: Apr. 1, 2010

(86) PCT No.: PCT/GB2010/000674
§ 371 (c)(1),
(2), (4) Date: Dec. 20, 2011

(87) PCT Pub. No.: WO2010/112874
PCT Pub. Date: Oct. 7, 2010

(65) Prior Publication Data
US 2012/0094996 A1    Apr. 19, 2012

(30) Foreign Application Priority Data
Apr. 2, 2009 (EP) .............................. 9380069

(51) Int. Cl.
*A61K 31/433* (2006.01)
*A61K 31/4188* (2006.01)
*C07D 285/02* (2006.01)
*C07D 235/00* (2006.01)

(52) U.S. Cl.
USPC ........ 514/363; 514/393; 514/233.2; 548/136; 548/303.1; 546/256; 546/268.7; 544/333; 544/124

(58) Field of Classification Search
USPC .................. 514/363, 393; 548/136, 303.1
See application file for complete search history.

(56) References Cited

U.S. PATENT DOCUMENTS

| | | | |
|---|---|---|---|
| 4,709,031 A | 11/1987 | Ingendoh et al. | |
| 2007/0049591 A1 | 3/2007 | Pinkerton et al. | |
| 2007/0093490 A1 | 4/2007 | Prien et al. | |
| 2011/0190289 A1 * | 8/2011 | Pevarello et al. | ......... 514/233.2 |

FOREIGN PATENT DOCUMENTS

| | | |
|---|---|---|
| CN | 101037445 | 9/2007 |
| EP | 0 041 215 | 12/1981 |
| EP | 0088323 | 2/1983 |
| EP | 0 662 477 | 7/1995 |
| GB | 1464259 | 2/1977 |
| WO | 97/11075 | 3/1997 |
| WO | 02/12250 | 2/2002 |
| WO | 2003/051890 | 6/2003 |
| WO | 2004/058769 | 7/2004 |
| WO | WO-2004/078110 | 9/2004 |
| WO | 2004/111060 | 12/2004 |
| WO | WO-2004/111061 | 12/2004 |
| WO | 2006-051270 | 5/2006 |
| WO | WO-2006/128692 | 12/2006 |
| WO | WO-2007/118318 | 4/2007 |
| WO | 2007/064797 | 6/2007 |
| WO | 2007-129044 | 11/2007 |
| WO | 2007-135398 | 11/2007 |
| WO | 2007/136736 | 11/2007 |
| WO | 2008-025821 | 3/2008 |
| WO | WO-2008/030579 A2 | 3/2008 |
| WO | WO-2008/060578 A2 | 5/2008 |
| WO | 2008/138834 | 11/2008 |
| WO | 2008-144463 | 11/2008 |
| WO | 2008-144464 | 11/2008 |
| WO | WO-2008/144767 | 11/2008 |
| WO | 2009/040552 | 4/2009 |
| WO | 2009-055418 | 4/2009 |
| WO | WO 2009040552 A2 * | 4/2009 |
| WO | WO-2010/012345 | 7/2009 |

OTHER PUBLICATIONS

Dehuri et al., J. Ind. Chem. Soc, 59(10), 1170-3 (1982) cited in IDS.*
Abdel-Magid A. F., et al., J. Org. Chem., (1996), vol. 61, p. 3849.
Abdel-Magid A. F., et al., Synthesis, (1990), p. 537.
Abignente et al., Farmaco, Edizione Scientifica (1985), vol. 40(3), pp. 190-199.
Abignente, et al., II Farmaco, (1990), vol. 45, p. 1075.
Andanappa K. Gadad, et al., Bioorg. Med. Chem., (2004), vol. 12, pp. 5651-5659.
Andreani et al., Arzneimittel-Forschung (2000), vol. 50(6), pp. 550-553.
Asunción Marin, et al., Farmaco, (1992), vol. 47 (1), pp. 63-75.
Bellamy F.D., et al., Tetrahedron Letters, (1985), vol. 25, p. 839.
Bretonnet, et al., J. Med. Chem. (2007), vol. 50, p. 1872.
Cohen, Current Opinion in Chemical Biology, (1999), vol. 3, pp. 459-465.
Defacqz N., et al., Tetrahedron Letters, (2003), vol. 44, p. 9111.

(Continued)

*Primary Examiner* — Yong Chu
(74) *Attorney, Agent, or Firm* — McCarter & English, LLP; Steven G. Davis

(57) ABSTRACT

There is provided compounds of formula (I): wherein $R^1$, $R^2$ and $R^3$ have meanings given in the description, and pharmaceutically-acceptable esters, amides, solvates or salts thereof, which compounds are useful in the treatment of diseases in which inhibition of a protein or lipid kinase (e.g. PI3-K, particularly class I PI3K) is desired and/or required, and particularly in the treatment of cancer.

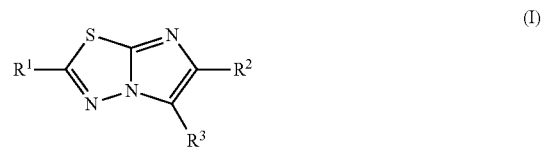

(I)

19 Claims, No Drawings

(56) References Cited

OTHER PUBLICATIONS

Dehuri S. N., et al., Journal of the Indian Chemical Society (1982), vol. 59(10), pp. 1170-1173.
Dermer O. C., Chem. Rev., (1934), vol. 14, p. 385.
Ei-Sherbeny M.A., et al., Boll. Chim. Farm., (1997), vol. 136, pp. 253-256.
Fabio P.F., et al., Journal of Labelled Compounds and Pharmaceuticals, (1978), vol. 15, p. 407.
Gregson S.J., et al., J. Med. Chem., (2004), vol. 47, p. 1161.
Han S. Y., et al., Tetrahedron, (2004), vol. 60, p. 2447.
Hennessey, et al., Nature Rev. Drug Discovery 4: (2005), pp. 988-1004.
Ikemoto T., et al., Heterocycles, (2001), vol. 55, p. 99.
Ikemoto T., et al., Tetrahedron, (2000), vol. 56, p. 7915.
Joshi, et al., Journal of the Indian Chemical Society (1979), vol. 56(7), pp. 716-717.
Katso, et al., Annu. Rev. Cell. Dev. Boil., (2001), vol. 17, pp. 615-675.
Kobe J., et al., Tetrahedron, (1968), vol. 24, p. 239.
Kuwahara M., et al., Chem. Pharm Bull., (1996), vol. 44, p. 122.
Lainton J. A. H., et al., J. Comb. Chem., (2003), vol. 5, p. 400.
Leslie, et al., Chem. Rev., (2001), vol. 101(8), pp. 2365-2380.
Parsons, et al., Nature 436:(2005), p. 792.
Paul Heinz, et al., Monatshefte für Chemie, (1977), vol. 108, pp. 665-680.
Plotkin M., et al., Tetrahedron Letters, (2000), vol. 41, p. 2269.
Schlosser M., et al., Organometallics in Synthesis. A Manual, (M. Schlosser, Ed.), Wiley & Sons Ltd: Chichester, UK, (2002).
Severinsen R., et al., Tetrahedron, (2005), vol. 61, pp. 5565-5575.
Seyden-Penne J., Reductions by the Alumino and Borohydrides, VCH, NY, (1991).
Shintani, R., et al., Org. Letters, (2005), vol. 7(21), pp. 4757-4759.
Terzioglu, et al., Eur. J. of Med. Chem. (2003), vol. 38(7-8), pp. 781-786.
Toker, et al., Cell. Mol. Life Sci., (2002), vol. 59(5), pp. 761-779.
Vanhaesebroeck, et al., Exp. Cell. Res., (1999), vol. 25(1), pp. 239-254.
Vanhaesebroeck, et al., Trends Biochem. Sci., (1997), vol. 22(7), pp. 267-272.
Wenwei L., et al., Tetrahedron Letters, (2006), vol. 47, p. 1941.
Werber G., et al., J. Heterocycl. Chem.; 14; (1977); pp. 823-827.
Wiggins J. M., et al., Synth. Commun., (1988), vol. 18, p. 741.
Wipf P., et al., J. Org. Chem., (2000), vol. 65(20), pp. 6319-6337.
CAS RN 342782-02-9 (2001).
Final Rejection in U.S. Appl. No. 12/679,514 mailed Apr. 5, 2013.
Hegde et al. *J. Sulfur Chem*. 2006, 27, 553-569.
Kolavi et al. *Bioor. Med. Chem*. 2006, 14, 3069-3080.
Kurtz, J. E. et al. *Anticancer Res*. 2012, 32, 2436-2470.
Non-Final Rejection in U.S. Appl. No. 12/679,514 mailed Dec. 28, 2012.
XP-002470755, Dehuri, S.N. et al. "Studied on heterocyclic compounds. Part V. synthesis and antimicrobial activities of N-bridged thiazole and imidazole derivatives" (1982) Database Accession No. 1983:179345.
Zhang et al. *Chem. J. Chinese U*. 2002, 23, 1882-1886.
XP-002470756, Substance Identification, Beilstein Data: 1975.
Wallin J. J., et al., *PLoS One*, 2012, 7(5), e36402, 1-11.
STN Registry 57772-06-2, (1984).
STN Registry RN 85487-48-5 to RN 85487-80-5, (1984).

* cited by examiner

IMIDAZO [2, 1-B] [1, 3, 4] THIADIAZOLE DERIVATIVES

FIELD OF THE INVENTION

This invention relates to novel pharmaceutically-useful compounds, which compounds are useful as inhibitors of protein and lipid kinases (such as inhibitors of the phosphoinositide 3'OH kinase (PI3 kinase) family, particularly the class I sub-type). The compounds are of potential utility in the treatment of diseases such as cancer. The invention also relates to the use of such compounds as medicaments, to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465.

Phosphatidylinositol 3-kinases (PI3Ks) are a family of lipid and serine/threonine kinases that catalyze the phosphorylation of the membrane lipid phosphatidylinositol (PI) on the 3'-OH of the inositol ring to produce phosphoinositol-3-phosphate (PIP), phosphoinositol-3,4-diphosphate ($PIP_2$) and phosphoinositol-3,4,5-triphosphate ($PIP_3$), which act as recruitment sites for various intracellular signalling proteins, which in turn form signalling complexes to relay extracellular signals to the cytoplasmic face of the plasma membrane.

These 3'-phosphoinositide subtypes function as second messengers in intra-cellular signal transduction pathways (see e.g. Trends Biochem. Sci 22 87,267-72 (1997) by Vanhaesebroeck et al.; Chem. Rev. 101 (8), 2365-80 (2001) by Leslie et al (2001); Annu. Rev. Cell. Dev. Boil. 17, 615-75 (2001) by Katso et al; and Cell. Mol. Life Sci. 59 (5), 761-79 (2002) by Toker et al).

Multiple PI3K isoforms categorized by their catalytic subunits, their regulation by corresponding regulatory subunits, expression patterns and signalling specific functions (p110α, β, δ, γ) perform this enzymatic reaction (Exp. Cell. Res. 25 (1), 239-54 (1999) by Vanhaesebroeck and Katso et al., 2001, above).

The closely related isoforms p110α and β are ubiquitously expressed, while δ and γ are more specifically expressed in the haematopoietic cell system, smooth muscle cells, myocytes and endothelial cells (see e.g. Trends Biochem. Sci. 22 (7), 267-72 (1997) by Vanhaesebroeck et al). Their expression might also be regulated in an inducible manner depending on the cellular, tissue type and stimuli as well as disease context. Inductibility of protein expression includes synthesis of protein as well as protein stabilization that is in part regulated by association with regulatory subunits.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain containing p85 adapter subunit. Class Ia PI3Ks are activated through tyrosine kinase signalling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p110 regulatory subunit. PI3Kγ is regulated by G protein coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

These observations show that deregulation of phosphoinositol-3-kinase and the upstream and downstream components of this signalling pathway is one of the most common deregulations associated with human cancers and proliferative diseases (see e.g. Parsons et al., Nature 436:792 (2005); Hennessey et al., Nature Rev. Drug Discovery 4: 988-1004 (2005).

The listing or discussion of an apparently prior-published document in this specification should not necessarily be taken as an acknowledgement that the document is part of the state of the art or is common general knowledge.

International patent application WO 2007/064797 discloses various compounds that may be useful in the treatment of cancer. However, there is no mention in that document of imidazothiadiazoles.

US patent applications US 2007/0049591 and US 2007/0093490 and international patent application WO 2004/058769 all disclose various compounds that may be useful as kinase inhibitors. Further, international patent application WO 2007/0136736 discloses various compounds that may be useful as Lck inhibitors. However, all these documents only mention compounds in which the core ring structure is a 6,5-ring system.

International patent application WO 2004/111060 discloses various imidazothiadiazoles that may be useful in the treatment of neurodegenerative diseases and cancer. However, this document primarily relates to 6-aryl substituted imidazo[2,1-b]-1,3,4-thiadiazoles, substituted in the 2-position with a sulfur (or oxidised derivative thereof) linker group. Further, international patent application WO 03/051890 also discloses various imidazothiadiazoles, which may be useful in the treatment of neurodegenerative diseases and cancer. However, this document primarily relates to 6-aryl substituted imidazo[2,1-b]-1,3,4-thiadiazoles, substituted in the 2-position with a sulfonamide group.

Journal article *European Journal of Medicinal Chemistry* (2003), 38(7-8), 781-786 by Terzioglu et al discloses various compounds that may be useful in the treatment of cancer. However, this document only discloses compounds that contain a carbohydrazide moiety.

Italian journal article *Arzneimittel-Forschung* (2000), 50(6), 550-553 by Andreani et al discloses various compounds including specific imidazothiadiazoles. However, there is no mention in this journal article that the compounds disclosed therein may be useful as protein kinase inhibitors.

International patent application WO 97/11075 discloses various compounds imidazothiadiazoles as herbicides. However, there is no disclosure that such compounds may be useful as pharmaceuticals, e.g. in the treatment of cancer.

European patent application EP 662 477 and journal article *Journal of the Indian Chemical Society* (1979), 56(7), 716-17 by Joshi et al, both disclose various heterobicyclic compounds, including specific imidazolothiadiazole compounds, which may be active as fungicides. However, there is no disclosure in either of these documents that the compounds disclosed therein may be useful as protein kinase inhibitors.

Italian journal article *Farmaco, Edizione Scientifica* (1985), 40(3), 190-9 by Abignente et al and European patent application EP 41215 both disclose various imidazolothiadiazoles, which may have been tested for medicinal properties for research purposes.

Various imidazolothiadiazoles have also been disclosed in *Journal of the Indian Chemical Society* (1982), 59(10), 1170-3 as potential fungicides and/or bactericides.

International patent application WO 2009/040552 discloses various imidazolothiadiazole compounds for use as kinase inhibitors. However, this document does not predominantly relate to imidazolothiadiazoles directly substituted at the 2- and 5-position with an aromatic group.

DISCLOSURE OF THE INVENTION

According to the invention, there is provided a compound of formula I,

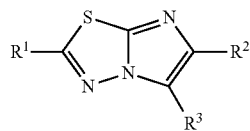

wherein:

$R^1$ represents:
(i) aryl substituted with one or more substituents selected from $A^1$;
(ii) heteroaryl optionally substituted with one or more substituents selected from $A^2$;
$R^2$ represents hydrogen or $C_{1-3}$ alkyl optionally substituted by one or more fluoro atoms;
$R^3$ represents aryl or heteroaryl, each of which is optionally substituted by one or more substituents selected from $A^3$ and $A^4$, respectively;
each $A^1$, $A^2$, $A^3$ and $A^4$ independently represents, on each occasion when used herein:
(i) $Q^1$;
(ii) $C_{1-12}$ alkyl or heterocycloalkyl, both of which are optionally substituted by one or more substituents selected from $=O$, $=S$, $=N(R^{10a})$ and $Q^2$;
(iii) aryl or heteroaryl, both of which are optionally substituted by one or more substituents selected from $Q^3$;
each $Q^1$, $Q^2$ and $Q^3$ independently represents, on each occasion when used herein:
halo, —CN, —NO$_2$, —N(R$^{10a}$)R$^{11a}$, —OR$^{10a}$, —C(=Y)—R$^{10a}$, —C(=Y)—OR$^{10a}$, —C(=Y)N(R$^{10a}$)R$^{11a}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —SC(=Y)OR$^{10a}$, —SC(=Y)N(R$^{10a}$)R$^{11a}$, —S(O)$_2$R$^{10a}$, —SR$^{10a}$, —S(O)R$^{10a}$, —S(O)$_2$OR$^{10a}$, $C_{1-12}$ alkyl, heterocycloalkyl (which latter two groups are optionally substituted by one or more substituents selected from =O, =S, =N(R$^{20}$) and E$^1$), aryl or heteroaryl (which latter two groups are optionally substituted by one or more substituents selected from E$^2$);
each R$^{10a}$, R$^{11a}$ and R$^{12a}$ independently represents, on each occasion when used herein, hydrogen, $C_{1-12}$ alkyl, heterocycloalkyl (which latter two groups are optionally substituted by one or more substituents selected from =O, =S, =N(R$^{20}$) and E$^3$), aryl or heteroaryl (which latter two groups are optionally substituted by one or more substituents selected from E$^4$); or
any relevant pair of R$^{10a}$, R$^{11a}$ and R$^{12a}$ may (for example, when attached to the same atom, adjacent atom (i.e. 1,2-relationship) or to atoms that are two atom atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (e.g. triple or, preferably, double bonds), and which ring is optionally substituted by one or more substituents selected from =O, =S, =N(R$^{20}$) and E$^5$;
each E$^1$, E$^2$, E$^3$, E$^4$ and E$^5$ independently represents, on each occasion when used herein:
(i) $Q^4$;
(ii) $C_{1-12}$ alkyl or heterocycloalkyl, both of which are optionally substituted by one or more substituents selected from =O and $Q^5$;
(iii) aryl or heteroaryl, both of which are optionally substituted by one or more substituents selected from $Q^6$;
each $Q^4$, $Q^5$ and $Q^6$ independently represents, on each occasion when used herein:
halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —SC(=Y)OR$^{20}$, —SC(=Y)N(R$^{20}$)R$^{21}$, —S(O)$_2$R$^{20}$, —SR$^{20}$, —S(O)R$^{20}$, —S(O)$_2$OR$^{20}$, $C_{1-12}$ alkyl, heterocycloalkyl (which latter two groups are optionally substituted by one or more substituents selected from =O and J$^1$), aryl or heteroaryl (which latter two groups are optionally substituted by one or more substituents selected from J$^2$);
each Y independently represents, on each occasion when used herein, =O, =S or =NR$^{23}$;
each R$^{20}$, R$^{21}$, R$^{22}$ and R$^{23}$ independently represents, on each occasion when used herein, hydrogen, $C_{1-6}$ alkyl, heterocycloalkyl (which latter two groups are optionally substituted by one or more substituents selected from J$^3$ and =O), aryl or heteroaryl (which latter two groups are optionally substituted by one or more substituents selected from J$^4$); or
any relevant pair of R$^{20}$, R$^{21}$ and R$^{22}$, may (for example, when attached to the same atom, adjacent atom (i.e. 1,2-relationship) or to atoms that are two atom atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (e.g. triple or, preferably, double bonds), and which ring is optionally substituted by one or more substituents selected from J$^5$ and =O;
each J$^1$, J$^2$, J$^3$, J$^4$ and J$^5$ independently represents, on each occasion when used herein:

(i) $Q^7$;
(ii) $C_{1-6}$ alkyl or heterocycloalkyl, both of which are optionally substituted by one or more substituents selected from =O and $Q^8$;
(iii) aryl or heteroaryl, both of which are optionally substituted by one or more substituents selected from $Q^9$;
each $Q^7$, $Q^8$ and $Q^9$ independently represents, on each occasion when used herein:
—CN or, more preferably, halo, —N($R^{50}$)$R^{51}$, —$OR^{50}$, —C(=$Y^a$)—$R^{50}$, —C(=Y)—$OR^{50}$, —C(=$Y^a$)N($R^{50}$)$R^{51}$, —N($R^{52}$)C(=$Y^a$)$R^{51}$, —$NR^{52}$S(O)$_2$$R^{50}$, —S(O)$_2$$R^{50}$, —$SR^{50}$, —S(O)$R^{50}$ or $C_{1-6}$ alkyl optionally substituted by one or more fluoro atoms;
each $Y^a$ independently represents, on each occasion when used herein, =O, =S or =$NR^{53}$;
each $R^{50}$, $R^{51}$, $R^{52}$ and $R^{53}$ independently represents, on each occasion when used herein, hydrogen or $C_{1-6}$ alkyl optionally substituted by one or more substituents selected from fluoro, —$OR^{60}$ and —N($R^{61}$)$R^{62}$; or
any relevant pair of $R^{50}$, $R^{51}$ and $R^{52}$ may (for example when attached to the same or adjacent atoms) be linked together to form, a 3- to 8-membered ring, optionally containing one or more heteroatoms (for example, in addition to those that may already be present, heteroatoms selected from oxygen, nitrogen and sulfur), optionally containing one or more unsaturations (e.g. triple or, preferably, double bonds), and which ring is optionally substituted by one or more substituents selected from =O and $C_{1-3}$ alkyl;
$R^{60}$, $R^{61}$ and $R^{62}$ independently represent hydrogen or $C_{1-6}$ alkyl optionally substituted by one or more fluoro atoms;
or a pharmaceutically acceptable ester, amide, solvate or salt thereof,
provided that when $R^2$ represents H, then:
(I) when $R^1$ represents 4-chlorophenyl, then $R^3$ does not represent unsubstituted phenyl or 4-chlorophenyl;
(II) when $R^1$ represents 4-methoxyphenyl, then $R^3$ does not represent 4-chlorophenyl or unsubstituted phenyl,
which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of such an ester or amide, and solvates of such an ester, amide or salt. For instance, pharmaceutically acceptable esters and amides such as those defined herein may be mentioned, as well as pharmaceutically acceptable solvates or salts.

Pharmaceutically acceptable esters and amides of the compounds of the invention are also included within the scope of the invention. Pharmaceutically acceptable esters and amides of compounds of formula I may have an appropriate group, for example an acid group, converted to the appropriate ester or amide. For example, pharmaceutically acceptable esters (of carboxylic acids) that may be mentioned include optionally substituted $C_{1-6}$ alkyl, $C_{5-10}$ aryl and/or $C_{5-10}$ aryl-$C_{1-6}$ alkyl-esters. Pharmaceutically acceptable amides (of carboxylic acids) that may be mentioned include those of the formula —C(O)N($R^{z1}$)$R^{z2}$, in which $R^{z1}$ and $R^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Preferably, specific esters and amides of compounds of the invention that may be mentioned include esters and amides of compounds of the invention.

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. I-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$O, $^{17}$O, $^{18}$O, $^{32}$P, $^{33}$P, $^{35}$S, $^{18}$F, $^{36}$Cl, $^{123}$I, and $^{125}$I. Certain isotopically-labeled compounds of the present invention (e.g., those labeled with $^3$H and $^{14}$C) are useful in compound and for substrate tissue distribution assays. Tritiated ($^3$H) and carbon-I4 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise stated, the terms $C_{1-q}$ alkyl, and $C_{1-q}$ alkylene, groups (where q is the upper limit of the range) defined herein may be straight-chain or, when there is a sufficient number of carbon atoms, be branched-chain, saturated or unsaturated (so forming, for example, an alkenyl or alkynyl group).

$C_{3-q}$ cycloalkyl groups (where q is the upper limit of the range) that may be mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double or triple bonds (forming for example a cycloalkenyl or cycloalkynyl group). Substituents may be attached at any point on the cycloalkyl group. Further, where there is a sufficient number (i.e. a minimum of four) such cycloalkyl groups may also be part cyclic. For the avoidance of doubt, optional substituents may also be other cyclic groups, which may be attached via a single carbon atom common to both rings, so forming a spiro-cycle.

The term "halo", when used herein, includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between five and ten. Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) or a $C_{7-q}$ heterocycloalkynyl group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiotanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form (i.e. those heteroatoms may be substituted with one or two =O substituents, as appropriate). As stated herein other carbon atoms of the heterocycloalkyl groups mentioned herein may also be substituted by one or more =O substituents. For the avoidance of doubt, optional substituents may also be other cyclic groups, which may be attached via a single carbon atom common to both rings (so forming a Spiro cycle).

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-10}$ aryl groups. Such groups may be monocyclic, bicyclic or tricyclic and have between 6 and 10 ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. However, when aryl groups are bicyclic or tricyclic, they are linked to the rest of the molecule via an aromatic ring. For the avoidance of doubt, optional substituents include those defined herein and also include =O substituents that may be attached to any non-aromatic rings of a polycyclic (e.g. bicyclic) aryl group (however, in an emdodiment, =O substituents are not included). For the avoidance of doubt, optional substituents may also be other cyclic groups, which may be, when attached to a non-aromatic ring of an aryl group, attached via a single carbon atom common to both rings (so forming a spiro-cycle).

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 10 members and may be monocyclic, bicyclic or tricyclic, provided that at least one of the rings is aromatic (so forming, for example, a mono-, bi-, or tricyclic heteroaromatic group). However, when heteroaryl groups are bicyclic or tricyclic, they are linked to the rest of the molecule via an aromatic ring. Heteroaryl groups that may be mentioned include acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. For the avoidance of doubt, optional substituents include those defined herein and also include =O substituents that may be attached to any non-aromatic rings of a polycyclic (e.g. bicyclic) heteroaryl group (but, in an embodiment, =O substituents are not included). For the avoidance of doubt, optional substituents may also be other cyclic groups, which may be, when attached to a non-aromatic ring of a heteroaryl group, attached via a single carbon atom common to both rings (so forming a spiro-cycle). The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form.

It may be specifically stated that the heteroaryl group is monocyclic or bicyclic. In the case where it is specified that the heteroaryl is bicyclic, then it may be consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulphur.

For the avoidance of doubt, in cases in which the identity of two or more substituents in a compound of the invention may be the same, the actual identities of the respective substituents are not in any way interdependent. For example, in the situation in which there is more than one $A^1$ substituent present, then those $A^1$ substituents may be the same or different. Further, in the case where there are two $A^1$ substituents present, in which one represents —$OR^{10a}$ and the other represents —$C(O)$—$R^{10a}$, then those $R^{10a}$ groups are not to be regarded as being interdependent.

For the avoidance of doubt, in the instance where cyclic substituents (e.g. cycloalkyl or heterocycloalkyl groups) are present on groups (such as alkyl groups), then those cyclic substituents may be attached to the same carbon atom, so forming for example a spiro-cyclic group.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

For the avoidance of doubt, when a term such as "$R^{10a}$ to $R^{12a}$" is employed herein, this will be understood by the skilled person to mean $R^{10a}$, $R^{11a}$ and $R^{12a}$, inclusively. Likewise, a term such as "$A^1$ to $A^4$" when employed herein, will be understood by the skilled person to mean $A^1$, $A^2$, $A^3$ and $A^4$, inclusively.

In an embodiment of the invention, there is provided compounds of the invention as hereinbefore defined but in which $R^2$ represents hydrogen. In another embodiment of the invention, there is provided compounds of the invention as hereinbefore defined but in which $R^2$ represents $C_{1-3}$ alkyl (e.g. methyl) optionally substituted by one or more fluoro atoms (e.g. especially those in which $R^2$ represents unsubstituted methyl).

Compounds of the invention that may be mentioned include those in which, for example, particularly for the embodiment in which $R^2$ represents hydrogen:

when $R^1$ represents substituted aryl, then it is preferably phenyl substituted with one or more substituents selected from $A^1$; and/or $R^1$ represents heteroaryl optionally substituted with one or more substituents selected from $A^2$;

$R^3$ represents unsubstituted aryl (e.g. phenyl); and/or when $R^3$ represents a heteroaryl group then it preferably represents:

(i) a monocyclic 5-membered heteroaryl group optionally substituted with one or more substituents selected from $A^4$;

(ii) a monocyclic 6-membered heteroaryl group in which the heteroatom is selected from oxygen and sulfur, and which group is optionally substituted with one or more substituents selected from $A^4$;

(iii) a monocyclic 6-membered heteroaryl group in which there are two or more nitrogen atoms present, which group is optionally substituted with one or more substituents selected from $A^4$;

(iv) a bicyclic heteroaryl group (e.g. a 8-, 9- or 10-membered ring), in which the point of attachment to the requisite bicycle of formula I is via a ring containing a heteroatom, and which bicyclic ring is optionally substituted with one or more substituents selected from $A^4$;

(v) a bicyclic heteroaryl group substituted with one or more substituents selected from $A^4$.

Further compounds of the invention that may be mentioned include those in which each of the aromatic groups represented by $R^1$ and $R^3$ is substituted by a substituent defined herein.

Preferred compounds of the invention that may be mentioned include those in which:

the point of attachment of heteroaryl groups that $R^1$ and $R^3$ may represent is via a heterocyclic ring (e.g. heteroaromatic ring) of that heteroaryl group (for example, when the heteroaryl ring is bicyclic in which there is benzene ring fused to a heterocyclic ring, then the point of attachment is via the heterocyclic ring, rather than the benzene ring, e.g. an indolyl group is preferably linked via the 2- or 3-position);

when any relevant pair of $R^{10a}$, $R^{11a}$ and $R^{12a}$ and/or $R^{20}$, $R^{21}$ and $R^{22}$ are linked together, then they may be linked when those substituents are attached to the same atom (i.e. the same nitrogen atom to which they are necessarily attached);

when either of $R^1$ and $R^3$ represent a heteroaryl group, then it may be a:

(i) monocyclic 5- or 6-membered ring, containing between one and four heteroatoms (e.g. between one and three, preferably one or two), in which the heteroatoms are preferably selected from oxygen, sulfur and, especially, nitrogen, and which ring is optionally substituted as defined herein;

(ii) a bicyclic 8-, 9- or 10-membered heteroaryl group, containing between one and four heteroatoms (e.g. between one and three, preferably one or two), and in which the bicycle consists of a 5- or 6-membered ring fused with another 5- or 6-membered ring. Preferably, it consists of a benzene ring fused to a monocyclic heteroaryl group as defined herein (e.g. a 5- or 6-membered ring as defined above).

Preferred compounds of the invention include those in which the aromatic groups defined by $R^1$ and/or $R^3$ are substituted (or at least one of those groups are substituted). Preferably, when such groups are substituted, they are substituted with one or two substituents as defined herein. It is preferred that such substituents are located at the para and/or meta position relative to the point of attachment to the requisite (imidazolothiadiazole) bicycle of the compound of formula I (e.g. when $R^1$ and/or $R^3$ represents phenyl, then preferably those substituents are located at the 3- and/or 4-position; when $R^1$ and/or $R^3$ represents substituted 3-pyridyl, then it is preferred that those substituents are substituted at the 5- and/or 6-position; when $R^1$ and/or $R^3$ represents substituted 5-pyrimidinyl, then the substituent is preferably located at the 2-position). Preferably, there is at least one substituent present on the $R^1$ and/or $R^3$ group (more particularly, there is at least one substituent present on both groups), which is located at the meta or, preferably, the para position.

More preferred compounds of the invention include those in which:

$A^1$, $A^2$, $A^3$ and $A^4$ independently represent, on each occasion when used herein, $Q^1$ or $C_{1-6}$ (e.g. $C_{1-3}$) alkyl substituted by one or more substituents selected from $Q^2$;

each $Q^1$, $Q^2$ and $Q^3$ independently represent, on each occasion when used herein halo, —CN, —NO$_2$, —N(R$^{10a}$)R$^{11a}$, —OR$^{10a}$, —C(=Y)—R$^{10a}$, —(=Y)OR$^{10a}$, —C(=Y)N(R$^{10a}$)R$^{11a}$, —N(R$^{12a}$)C(=Y)R$^{11a}$, —N(R$^{12a}$)C(=Y)OR$^{11a}$, —NR$^{12a}$S(O)$_2$R$^{10a}$, —S(O)$_2$N(R$^{10a}$)R$^{11a}$, —S(O)$_2$R$^{10a}$, —SR$^{10a}$, —S(O)R$^{10a}$ or $C_{1-12}$ (e.g. $C_{1-6}$) alkyl (optionally substituted by one or more substituents selected from =O and, preferably, E$^1$);

each $R^{10a}$, $R^{11a}$ and $R^{12a}$ independently represent, on each occasion when used herein, hydrogen or $C_{1-12}$ alkyl optionally substituted by one or more substituents selected from =O and, preferably, E$^3$); or any relevant pair of $R^{10a}$, $R^{11a}$ and $R^{12a}$ (e.g. $R^{10a}$ and $R^{11a}$) may be linked together to form (e.g. when attached to the same nitrogen atom, along with the requisite nitrogen atom to which they are attached) a 4- to 8-membered ring, optionally containing one or more double bonds (e.g. one or two), and which ring may contain a further two or, preferably, one heteroatom (preferably selected from nitrogen and, especially, oxygen), and which ring is optionally substituted by one or more substituents selected from $E^5$ and =O;

$E^1$, $E^2$, $E^3$, $E^4$ and $E^5$ (e.g. $E^1$, $E^2$ and $E^3$) independently represent, on each occasion when used herein, $Q^4$ or $C_{1-6}$ (e.g. $C_{1-3}$) alkyl optionally substituted by one or more substituents selected from =O and, preferably, $Q^5$ (most preferably such $E^1$ to $E^5$ groups represent $Q^4$);

each $Q^4$, $Q^5$ and $Q^6$ (e.g. $Q^4$) independently represents, on each occasion when used herein halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —N(R$^{22}$)C(=Y)R$^{21}$, —N(R$^{22}$)C(=Y)OR$^{21}$, —NR$^{22}$S(O)$_2$R$^{20}$, —S(O)$_2$N(R$^{20}$)R$^{21}$, —S(O)$_2$R$^{20}$, —SR$^{20}$, —S(O)R$^{20}$, or $C_{1-6}$ alkyl optionally substituted by one or more substituents selected from fluoro;

each Y independently represents, on each occasion when used herein, =O;

each $R^{20}$, $R^{21}$, $R^{22}$ and $R^{23}$ independently represent, on each occasion when used herein, hydrogen or $C_{1-3}$ alkyl optionally substituted by one or more substituents selected from $J^3$ and =O; or any pair of $R^{20}$, $R^{21}$ and $R^{22}$ (e.g. $R^{20}$ and $R^{21}$) may be linked together to form (e.g. when attached to the same nitrogen atom, along with the requisite nitrogen atom to which they are attached) a 4- to 8-membered ring, optionally containing one or more double bonds (e.g. one or two), and which ring may contain a further two or, preferably, one heteroatom (preferably selected from nitrogen and, especially, oxygen), and which ring is optionally substituted by one or more substituents selected from $J^5$ and =O;

each $J^1$, $J^2$, $J^3$, $J^4$ and $J^5$ independently represents, on each occasion when used herein: (i) $Q^7$; or (ii) $C_{1-6}$ (e.g. $C_{1-3}$) alkyl optionally substituted by one or more substituents selected from =O and $Q^8$ (more preferably, each $J^1$, $J^2$, $J^3$, $J^4$ and $J^5$ (e.g. each $J^1$ and $J^2$) independently represents $Q^7$);

each $Q^7$, $Q^8$ and $Q^9$ (e.g. $Q^7$) independently represents —N(R$^{50}$)R$^{51}$, —OR$^{50}$ or, preferably, halo (e.g. fluoro) or $C_{1-3}$ alkyl (e.g. methyl) optionally substituted by one or more fluoro atoms;

each $Y^a$ independently represents =O;

each $R^{50}$, $R^{51}$, $R^{52}$ and $R^{53}$ substituent independently represents, on each occasion when used herein, hydrogen or $C_{1-6}$ (e.g. $C_{1-3}$) alkyl optionally substituted by one or more substituents selected from fluoro;

$R^{60}$, $R^{61}$ and $R^{62}$ independently represent methyl or hydrogen.

Preferred aryl and heteroaryl groups that $R^1$ and $R^3$ may independently represent include optionally substituted phenyl, naphthyl, pyrrolyl, furanyl, thienyl, imidazolyl, oxazolyl, isoxazolyl, thiazolyl, pyrazolyl, pyridyl, indazolyl, indolyl, indolinyl, isoindolinyl, quinolinyl, isoquinolinyl, quinolizinyl, benzoxazolyl, benzofuranyl, isobenzofuranyl, chromanyl, benzothienyl, pyridazinyl, pyrimidinyl, pyrazinyl, indazolyl, benzimidazolyl, quinazolinyl, quinoxalinyl, 1,3-benzodioxolyl, tetrazolyl, benzothiazolyl, and/or benzodioxanyl. Particularly preferred groups that $R^1$ and $R^3$ may independently represent include optionally substituted phenyl, pyridyl (e.g. 3-pyridyl) and pyrimidinyl (e.g. 5-pyrimidinyl).

Preferred substituents on aryl or heteroaryl groups that $R^1$ and $R^3$ may represent include (as appropriate):
=O (e.g. in the case of cycloalkyl or, preferably, heterocycloalkyl groups);
—CN;
halo (e.g. fluoro, chloro or bromo);
$C_{1-4}$ alkyl, which alkyl group may be cyclic, part-cyclic, unsaturated or, preferably, linear or branched (e.g. $C_{1-4}$ alkyl (such as ethyl, n-propyl, isopropyl, t-butyl or, preferably, n-butyl or methyl), all of which are optionally substituted with one or more substituents selected from —$OR^{z1}$, —$N(R^{z4})R^{z5}$ (so forming for example a —$CH_2$—$CH_2$—OH or —$CH_2$—$CH_2$—$N(CH_3)_2$ group) and, preferably, halo (e.g. fluoro; so forming, for example, fluoromethyl, difluoromethyl or, preferably, trifluoromethyl);
aryl (e.g. phenyl), if appropriate (e.g. when a substitutent on an alkyl group, thereby forming e.g. a benzyl group);
—$OR^{z1}$;
—$C(O)R^{z2}$;
—$C(O)OR^{z3}$;
—$N(R^{z4})R^{z5}$;
—$S(O)_2R^{z6}$;
—$S(O)_2N(R^{z7})R^{z8}$;
—$N(R^{z9})R^{z10}$;
wherein $R^{z1}$ to $R^{z10}$ independently represent, on each occasion when used herein, H or $C_{1-4}$ alkyl (e.g. ethyl, n-propyl, t-butyl or, preferably, n-butyl, methyl or isopropyl) optionally substituted by one or more substituents selected from halo (e.g. fluoro), —$N(R^{z11})C(O)OR^{z12}$ and —$C(O)N(R^{z13})R^{z14}$, in which $R^{z11}$ to $R^{z14}$ independently represent H or $C_{1-4}$ alkyl (e.g. methyl or t-butyl), or $R^{z13}$ and $R^{z14}$ are linked together to form a 5- or 6-membered ring (optionally containing a further heteroatom, so forming e.g. a morpholinyl group).

Preferred compounds of the invention include those in which:
$R^1$ represents aryl (e.g. phenyl) substituted by one or more substituents selected from $A^1$, or, heteroaryl (e.g. pyridyl, such as 3-pyridyl) optionally substituted by one or more substituents selected from $A^2$;
when $R^1$ represents optionally substituted heteroaryl, then it preferably represents an optionally substituted monocyclic heteroaryl group (e.g. a 5- or, preferably, 6-membered monocyclic heteroaryl group), preferably containing two or, preferably, one heteroatom(s) (preferably selected from oxygen, sulfur or, especially, nitrogen);
$R^2$ represents hydrogen or methyl;
$R^3$ represents aryl (e.g. phenyl) optionally substituted by one or more substituents selected from $A^3$, or, heteroaryl (e.g. pyridyl, such as 3-pyridyl, and pyrimidinyl, such as 5-pyrimidinyl) optionally substituted by one or more substituents selected from $A^4$;
when $R^3$ represents optionally substituted heteroaryl, then it preferably represents an optionally substituted monocyclic heteroaryl group (e.g. a 5- or, preferably, 6-membered monocyclic heteroaryl group), preferably containing one or two heteroatoms (preferably selected from oxygen, sulfur or, especially, nitrogen);
both $R^1$ and $R^3$ preferably represent substituted aromatic (aryl or heteroaryl) groups as defined herein;
when $R^2$ represents hydrogen, then it is preferred that $R^1$ represents optionally substituted heteroaryl as defined herein;
$A^1$, $A^2$, $A^3$ and $A^4$ independently represent $Q^1$;
each $Q^1$, $Q^2$ and $Q^3$ (e.g. $Q^1$) independently represents halo (e.g. fluoro), —CN, —$OR^{10a}$, —$N(R^{10a})R^{11a}$, —$C(=Y)OR^{10a}$ or —$S(O)_2R^{10a}$;
each $R^{10a}$, $R^{11a}$ and $R^{12a}$ (e.g. $R^{10a}$) independently represents hydrogen, $C_{1-3}$ alkyl (e.g. methyl or ethyl), optionally substituted by one or more substituents selected from $E^3$;
each $E^1$, $E^2$, $E^3$, $E^4$ and $E^5$ (e.g. $E^3$) independently represent $Q^4$;
each $Q^4$, $Q^5$ and $Q^6$ (e.g. $Q^4$) independently represents —$N(R^{20})R^{21}$, —$C(=Y)N(R^{20})R^{21}$ or —$N(R^{22})C(=Y)OR^{21}$;
each Y independently represents =S or, preferably, =O;
$R^{20}$, $R^{21}$ and $R^{22}$ (e.g. $R^{20}$ and $R^{21}$) independently represent hydrogen or, preferably, $C_{1-4}$ alkyl (e.g. methyl or t-butyl); or
$R^{20}$ and $R^{21}$, when attached to the same nitrogen atom are linked together to form a 5- or 6-membered ring, optionally containing a further heteroatom (e.g. nitrogen, or, preferably, oxygen) so forming, e.g. a morpholinyl group;
$R^{22}$ represents hydrogen.

Preferred compounds of the invention include those in which:
$R^1$ represents aryl (e.g. phenyl) substituted by one or more substituents selected from $A^1$, or, heteroaryl (e.g. a 5-membered heteroaryl group such as pyrazolyl (e.g. 4-pyrazolyl), a 9- or 10-membered fused bicyclic ring such as indolyl (e.g. 5-indolyl or 2-oxo-1,2-dihydroindolyl) or, preferably a 6-membered heteroaryl group e.g. pyridyl, such as 3-pyridyl) optionally substituted by one or more substituents selected from $A^2$;
when $R^1$ represents bicyclic heteroaryl, then it is linked to the requisite imidazothiadiazole of the compounds of the invention (see formula I above) via an aromatic ring (e.g. a benzene ring);
$R^2$ represents hydrogen or methyl (preferably hydrogen);
$R^3$ represents aryl (e.g. phenyl) optionally substituted by one or more substituents selected from $A^3$, or, heteroaryl (e.g. pyridazinyl or, preferably, pyridyl, such as 3-pyridyl, and pyrimidinyl, such as 5-pyrimidinyl) optionally substituted by one or more substituents selected from $A^4$;
when $R^3$ represents optionally substituted heteroaryl, then it preferably represents an optionally substituted monocyclic heteroaryl group (e.g. a 5- or, preferably, 6-membered monocyclic heteroaryl group), preferably containing one or two heteroatoms (preferably selected from oxygen, sulfur or, especially, nitrogen);
both $R^1$ and $R^3$ preferably represent substituted aromatic (aryl or heteroaryl) groups as defined herein;
when $R^2$ represents hydrogen, then it is preferred that $R^1$ represents optionally substituted heteroaryl as defined herein;
$A^1$, $A^2$, $A^3$ and $A^4$ independently represent $Q^1$ or (e.g. $A^1$, $A^2$ or $A^4$) may alternatively represent $C_{1-6}$ (e.g. $C_{1-3}$) alkyl (e.g. methyl or ethyl) or heterocycloalkyl (e.g. a 6-membered heterocycloalkyl group; which may be linked via a single carbon atom common to the heterocycloalkyl group and the non-aromatic cyclic ring of an aryl or heteroaryl group to which that heterocycloalkyl group is attached), both of which are optionally substituted by one or more $Q^2$ substituents;
each $Q^1$, $Q^2$ and $Q^3$ (e.g. $Q^1$) independently represents $C_{1-6}$ (e.g. $C_{1-3}$) alkyl (optionally substituted by one or more fluoro atoms), a 5- or 6-membered heterocycloalkyl group (optionally substituted by one or more substitutents selected from E¹; which preferably contains one or two heteroatoms), —SR$^{10a}$, —S(O)R$^{10a}$, —NR$^{12a}$S(O)$_2$R$^{10a}$, —C(=Y)—N(R$^{10a}$)R$^{11a}$, —S(O)$_2$N(R$^{10a}$)R$^{11a}$, —N(R$^{12a}$)C(=Y)R$^{11a}$ or, more preferably, halo (e.g. chloro or, preferably, fluoro), —CN, —OR$^{10a}$, —N(R$^{10a}$)R$^{11a}$, —C(=Y)OR$^{10a}$ or —S(O)$_2$R$^{10a}$;

Q² represents halo (e.g. fluoro) or —NR$^{12a}$S(O)$_2$R$^{10a}$ (for instance, when on an alkyl group) or C$_{1-6}$ (e.g. C$_{1-3}$) alkyl (e.g methyl; which alkyl group is optionally substituted by one or more fluoro atoms) or —C(=Y)OR$^{10a}$ (for instance, when on a heteroatom, e.g. of a heterocycloalkyl group);

each R$^{10a}$, R$^{11a}$ and R$^{12a}$ (e.g. R$^{10a}$) independently represents hydrogen, C$_{1-3}$ alkyl (e.g. methyl or ethyl) or heterocycloalkyl (e.g. piperidinyl, such as 4-piperidinyl), which latter two groups are optionally substituted by one or more substituents selected from E³ (preferably each R$^{10a}$, R$^{11a}$ and R$^{12a}$ independently represent hydrogen or C$_{1-3}$ alkyl optionally substituted by one or more substituents selected from E³; in which E³ may be fluoro or another substituent as defined herein such as —N(R$^{20}$)R$^{21}$); or R$^{10a}$ (e.g. as a part of the above-mentioned —NR$^{12a}$S(O)$_2$R$^{10a}$ group) may represent aryl or heteroaryl (preferably aryl, such as phenyl) optionally substituted by one or more substituents selected from E⁴; or R$^{10a}$ and R$^{11a}$ (e.g. in the case of —S(O)$_2$N(R$^{10a}$)R$^{11a}$) may be linked together to form a 5- or preferably 6-membered ring optionally containing one further heteroatom (e.g. nitrogen or, preferably, oxygen), so forming for example a morpholinyl group (which ring may be substituted by one or more E⁵ substituents (but, e.g. in the case of a ring formed by the linkage of a —S(O)$_2$N(R$^{10a}$)R$^{11a}$ group, is preferably unsubstituted);

R$^{12a}$ represents C$_{1-3}$ alkyl or, preferably, hydrogen;

each E¹, E², E³, E⁴ and E⁵ (e.g. E³) independently represent C$_{1-6}$ (e.g. C$_{1-3}$) alkyl, heterocycloalkyl (which latter two groups are optionally substituted by one or more substituents selected from =O and, preferably, Q⁵) or E¹ to E⁵ (e.g. E³) independently (and more preferably) represent Q⁴ (in which E⁴ is preferably halo (e.g. fluoro));

each Q⁴, Q⁵ and Q⁶ (e.g. Q⁴) independently represent halo (e.g. fluoro), —C(=Y)—OR$^{20}$ or, more preferably, —N(R$^{20}$)R$^{21}$, —C(=Y)N(R$^{20}$)R$^{21}$ or —N(R$^{22}$)C(=Y)OR$^{21}$;

each Y independently represents =S or, preferably, =O;

R$^{20}$, R$^{21}$ and R$^{22}$ (e.g. R$^{20}$ and R$^{21}$) independently represent hydrogen or, preferably, C$_{1-4}$ alkyl (e.g. methyl or t-butyl); or R$^{20}$ and R$^{21}$, when attached to the same nitrogen atom are linked together to form a 5- or 6-membered ring, optionally containing a further heteroatom (e.g. nitrogen, or, preferably, oxygen) so forming, e.g. a morpholinyl group;

R$^{22}$ represents hydrogen.

Preferred compounds of the invention that may be mentioned include those in which:

R¹ represents aryl or, preferably, heteroaryl (e.g. 3-pyridyl) substituted (e.g. at the position meta to the point of attachment to the imidazothiadiazole, i.e. in the case of 3-pyridyl, at the 5-position) with —NR$^{12a}$S(O)$_2$R$^{10a}$, and optionally substituted with one or more (e.g. one to three, when R¹ represents pyridyl) further substituents selected from A¹ or A² (as appropriate);

R$^{12a}$ represents C$_{1-3}$ alkyl or, preferably, hydrogen;

R$^{10a}$ (e.g. as a part of the above-mentioned —NR$^{12a}$S(O)$_2$R$^{10a}$ group) represents aryl or heteroaryl (preferably aryl, such as phenyl) optionally substituted by one or more substituents selected from E⁴ (preferably when it represents phenyl, then that group is preferably substituted e.g. with two E⁴ substituents located at the ortho and para position; in which each E⁴ preferably represents fluoro);

when R¹ represents pyridyl (e.g. 3-pyridyl) substituted at the 5-position with —NR$^{12a}$S(O)$_2$R$^{10a}$, then the 2- and 4-positions are preferably unsubstituted and the 6-position is optionally (but preferably) substituted by A²;

when R¹ represents phenyl substituted at the 3-position with —NR$^{12a}$S(O)$_2$R$^{10a}$, then the 2, 5 and 6 positions are preferably unsubstituted and the 4-position is optionally (but preferably) substituted by A¹;

A¹ and A² independently represent Q¹;

Q¹ represents —OR$^{10a}$ (in which R$^{10a}$ is preferably C$_{1-3}$ alkyl optionally substituted by one or more fluoro atoms; preferably R$^{10a}$ in this instance represents unsubstituted methyl);

E⁴ represents Q⁴;

Q⁴ represents halo (especially fluoro);

R² represents hydrogen or C$_{1-3}$ alkyl (e.g. methyl) (preferably hydrogen);

R³ represents a 6-membered monocyclic heteroaryl group (in which there are one or two heteroatoms preferably selected from nitrogen; so forming e.g. a pyridazinyl (e.g. 4-pyridazinyl) group; preferably unsubstituted), which may be substituted with one or more A⁴ substituents, but which is preferably unsubstituted.

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I which process comprises:

(i) reaction of a corresponding compound of formula II, wherein L¹ represents a suitable leaving group, such as iodo, bromo, chloro or a sulfonate group (e.g. —OS(O)$_2$CF$_3$, —OS(O)$_2$CH$_3$ or —OS(O)$_2$PhMe) (most preferably L¹ represents iodo), and R¹ and R² are as hereinbefore defined, with a compound of formula III, $$L^2\text{-}R^3 \qquad \qquad III$$

wherein L² represents a suitable group such as —B(OH)$_2$, —B(OR$^{wx}$)$_2$ or —Sn(R$^{wx}$)$_3$, in which each R$^{wx}$ independently represents a C$_{1-6}$ alkyl group, or, in the case of —B(OR$^{wx}$)$_2$, the respective R$^{wx}$ groups may be linked together to form a 4- to 6-membered cyclic group (such as a 4,4,5,5-tetramethyl-1,3,2-dioxaborolan-2-yl group), and R³ is as hereinbefore defined (most preferably L² represents —B(OR$^{wx}$)$_2$). This reaction may be performed, for example in the presence of a suitable catalyst system, e.g. a metal (or a salt or complex thereof) such as CuI, Pd/C, PdCl$_2$, Pd(OAc)$_2$, Pd(Ph$_3$P)$_2$Cl$_2$, Pd(Ph$_3$P)$_4$ (i.e. palladium tetrakistriphenylphosphine), Pd$_2$(dba)$_3$ or NiCl$_2$ and a ligand such as t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof, together with a suitable base such as, $Na_2CO_3$, $K_3PO_4$, $Cs_2CO_3$, NaOH, KOH, $K_2CO_3$, CsF, $Et_3N$, $(i-Pr)_2NEt$, t-BuONa or t-BuOK (or mixtures thereof) in a suitable solvent such as dioxane, toluene, ethanol, dimethylformamide, ethylene glycol dimethyl ether, water, dimethylsulfoxide, acetonitrile, dimethylacetamide, N-methylpyrrolidinone, tetrahydrofuran, dimethoxyethane (DME) or mixtures thereof (preferably a polar aprotic solvent is employed, e.g. dioxane or DME). The reaction may also be carried out for example at room temperature or above (e.g. at a high temperature such as the reflux temperature of the solvent system). The reaction may also be carried out under microwave irradiation reaction conditions, for example at elevated temperature (e.g. at above 100° C., such as at about 135 to 140° C.). Alternative $L^2$ groups that may be mentioned include alkali metal groups (e.g. lithium) and halo groups, which may be converted to a magnesium halide (i.e. a Grignard reagent), in which the magnesium may undergo a 'trans-metallation' reaction, thereby being exchanged with, for example, zinc;

(ii) reaction of a compound of formula IV,

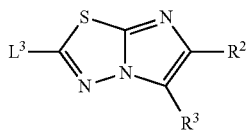

wherein $L^3$ represents a suitable leaving group, such as one hereinbefore defined in respect of $L^1$ (e.g. iodo), and $R^2$ and $R^3$ are as hereinbefore defined, with a compound of formula V, $$R^1\text{-}L^4 \qquad V$$

wherein $L^4$ represents a suitable leaving group, such as one hereinbefore defined in respect of $L^2$ (e.g. a boronic acid), and $R^1$ is as hereinbefore defined, for example under reaction conditions such as those hereinbefore described in respect of process step (i) above. Alternatively, steps (i) and (ii) may be performed in the same pot, i.e. the $L^1$ and $L^3$ moieties may be replaced with $R^3$ and $R^1$ in the same pot;

(iii) for compounds of formula I in which there is a $Q^1$ to $Q^6$ substituent present (i.e. $Q^1$, $Q^2$, $Q^3$, $Q^4$, $Q^5$ and/or $Q^6$ substituent present), in which such groups represent $-OR^{10a}$ or $-OR^{20}$, as appropriate, in which $R^{10a}$ and $R^{20}$ do not represent hydrogen (and most preferably represent optionally substituted alkyl as defined herein, e.g. $C_{1-12}$ or $C_{1-6}$ alkyl optionally substituted as defined herein), reaction of a corresponding compound of formula I in which there is a $Q^1$ to $Q^6$ present, which represents $-OR^{10a}$ and $-OR^{20}$ (as appropriate), in which $R^{10a}$ and $R^{20}$ do represent hydrogen, with a compound of formula VI, $$R^x\text{-}L^5 \qquad VI$$

wherein $L^5$ represents a suitable leaving group, such as one hereinbefore defined in respect of the $L^1$ definition (e.g. chloro or, preferably, bromo), and $R^x$ represents $R^{10a}$ or $R^{20}$ (as appropriate), provided that they do not represent hydrogen (and preferably represent $C_{1-12}$ or $C_{1-6}$ alkyl optionally substituted as defined herein), under reaction conditions known to those skilled in the art, the reaction may be performed at around room temperature or above (e.g. up to 40-180° C.), optionally in the presence of a suitable base (e.g. sodium hydride, sodium bicarbonate, potassium carbonate, pyrrolidinopyridine, pyridine, triethylamine, tributylamine, trimethylamine, dimethylaminopyridine, diisopropylamine, diisopropylethylamine, 1,8-diazabicyclo[5.4.0]undec-7-ene, sodium hydroxide, N-ethyldiisopropylamine, N-(methylpolystyrene)-4-(methylamino)pyridine, potassium bis(trimethylsilyl)-amide, sodium bis(trimethylsilyl)amide, potassium tert-butoxide, lithium diisopropylamide, lithium 2,2,6,6-tetramethylpiperidine or mixtures thereof) and an appropriate solvent (e.g. tetrahydrofuran, pyridine, toluene, dichloromethane, chloroform, acetonitrile, dimethylformamide, trifluoromethylbenzene, dioxane, triethylamine, water or mixtures thereof).

Compounds of formula II in which $L^1$ represents halo, may be prepared by reaction of a compound of formula VII,

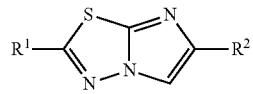

wherein $R^1$ and $R^2$ are as hereinbefore defined, with a source of halide ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride.

Other compounds of formula II may also be prepared under standard conditions, for instance such as those described herein. For example, for synthesis of compounds of formula II in which $L^1$ represents a sulfonate group, reaction of a compound corresponding to a compound of formula II but in which $L^1$ represents $-OH$ with an appropriate sulfonyl halide, under standard reaction conditions, such as in the presence of a base (e.g. as hereinbefore described in respect of preparation of compounds of formula I (process step (iii)).

Compounds of formula VII (e.g. those in which $R^2$ represents hydrogen or methyl) may be prepared by reaction of a compound of formula VII,

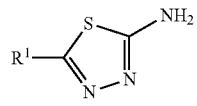

wherein $R^1$ is as hereinbefore defined, with a compound of formula IX, $$Cl\text{—}CH_2\text{—}C(O)\text{—}R^{2a} \qquad IX$$

wherein $R^{2a}$ represents hydrogen or $C_{1-3}$ alkyl optionally substituted by one or more halo (e.g. fluoro) atoms (most preferably $R^{2a}$ represents hydrogen or methyl), under standard conditions known to those skilled in the art. For example, the compound of formula IX may already be present in water, and hence, the reaction may be performed in the presence of water as a solvent, optionally in the presence of a further solvent, such as an alcohol (e.g. n-butanol), for example at room temperature or, preferably, elevated temperature such as at reflux.

Compounds of formula VIII may be prepared by reaction of a corresponding compound of formula X,

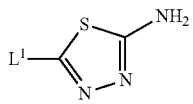

wherein L¹ is as hereinbefore defined, with a compound of formula V as hereinbefore defined, for example under reaction conditions such as those hereinbefore described in respect of preparation of compounds of formula I (process step (ii)).

Compounds of formula X in which L¹ represents halo, may be prepared by reaction of a corresponding compound of formula XI,

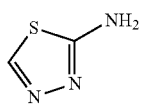

in the presence of a source of halide ions (e.g. in the case of bromide ions, bromine), such as those described hereinbefore in respect of preparation of compounds of formula II, for instance, in the presence of a suitable solvent, such as an alcohol (e.g. methanol) optionally in the presence of a suitable base, such as a weak inorganic base, e.g. sodium bicarbonate.

Compounds of formulae III, V, VI, IX and XI (as well as certain other intermediate compounds) are either commercially available, are known in the literature, or may be obtained either by analogy with the processes described herein, or by conventional synthetic procedures, in accordance with standard techniques, from available starting materials using appropriate reagents and reaction conditions. Further, the skilled person will appreciate that where reactions to introduce the "—R¹" moiety of compounds of formula I is described, similar reactions may be performed to introduce the "—R³" (or "—R²") moiety in compounds of formula I and vice versa. Further, processes to prepare compounds of formula I may be described in the literature, for example in:

Werber, G. et al.; *J. Heterocycl. Chem.*; EN; 14; 1977; 823-827;
Andanappa K. Gadad et al. *Bioorg. Med. Chem.* 2004, 12, 5651-5659;
Paul Heinz et al. *Monatshefte für Chemie*, 1977, 108, 665-680;
M. A. El-Sherbeny et al. *Boll. Chim. Farm.* 1997, 136, 253-256;
Nicolaou, K. C.; Bulger, P. G.; Sarlah, D. *Angew. Chem. Int. Ed.* 2005, 44, 2-49;
Bretonnet et al. *J. Med. Chem.* 2007, 50, 1872;
Asunción Marin et al. *Farmaco* 1992, 47 (1), 63-75;
Severinsen, R. et al. *Tetrahedron* 2005, 61, 5565-5575;
Nicolaou, K. C.; Bulger, P. G.; Sarlah, D. *Angew. Chem. Int. Ed.* 2005, 44, 2-49;
M. Kuwahara et al., *Chem. Pharm Bull.*, 1996, 44, 122;
Wipf, P.; Jung, J.-K. *J. Org. Chem.* 2000, 65(20), 6319-6337;
Shintani, R.; Okamoto, K. *Org. Lett.* 2005, 7 (21), 4757-4759;
Nicolaou, K. C.; Bulger, P. G.; Sarlah, D. *Angew. Chem. Int. Ed.* 2005, 44, 2-49;
J. Kobe et al., *Tetrahedron*, 1968, 24, 239;
P. F. Fabio, A. F. Lanzilotti and S. A. Lang, *Journal of Labelled Compounds and Pharmaceuticals*, 1978, 15, 407;
F. D. Bellamy and K. Ou, *Tetrahedron Lett.*, 1985, 25, 839;
M. Kuwahara et al., *Chem. Pharm Bull.*, 1996, 44, 122;
A. F. Abdel-Magid and C. A Maryanoff. *Synthesis*, 1990, 537;
M. Schlosser et al. *Organometallics in Synthesis. A Manual*, (M. Schlosser, Ed.), Wiley & Sons Ltd: Chichester, UK, 2002, and references cited therein;
L. Wengwei et al., *Tetrahedron Lett.*, 2006, 47, 1941;
M. Plotkin et al. *Tetrahedron Lett.*, 2000, 41, 2269;
Seyden-Penne, J. *Reductions by the Alumino and Borohydrides*, VCH, NY, 1991;
O. C. Dermer, *Chem. Rev.*, 1934, 14, 385;
N. Defacqz, et al., *Tetrahedron Lett.*, 2003, 44, 9111;
S. J. Gregson et al., *J. Med. Chem.*, 2004, 47, 1161;
A. M. Abdel Magib, et al., *J. Org. Chem.*, 1996, 61, 3849;
A. F. Abdel-Magid and C. A Maryanoff. *Synthesis*, 1990, 537;
T. Ikemoto and M. Wakimasu, *Heterocycles*, 2001, 55, 99;
E. Abignente et al., *Il Farmaco*, 1990, 45, 1075;
T. Ikemoto et al., *Tetrahedron*, 2000, 56, 7915;
T. W. Greene and P. G. M. Wuts, *Protective Groups in Organic Synthesis*, Wiley, NY, 1999;
S. Y. Han and Y.-A. Kim. *Tetrahedron*, 2004, 60, 2447;
J. A. H. Lainton et al., *J. Comb. Chem.*, 2003, 5, 400; or
Wiggins, J. M. *Synth. Commun.*, 1988, 18, 741.

Other specific transformation steps (including those that may be employed in order to form compounds of formula I) that may be mentioned include:

(i) reductions, for example of a carboxylic acid (or ester) to either an aldehyde or an alcohol, using appropriate reducing conditions (e.g. —C(O)OH (or an ester thereof), may be converted to a —C(O)H or —CH₂—OH group, using DIBAL and LiAlH₄, respectively (or similar chemoselective reducing agents));

(ii) reductions of an aldehyde (—C(O)H) group to an alcohol group (—CH₂OH), using appropriate reduction conditions such as those mentioned at point (i) above;

(iii) oxidations, for example of a moiety containing an alcohol group (e.g. —CH₂OH) to an aldehyde (e.g. —C(O)H) or of a —S— moiety to a —S(O)— or —S(O)₂— moiety (or the reverse reduction reaction), for example in the presence of a suitable oxidising agent, e.g. MnO₂ or mcpba or the like;

(iv) reductive amination of an aldehyde and an amine, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or MgSO₄ or molecular sieves, etc) followed by a reduction step (e.g. by reaction in the presence of a reducing agent such as a chemoselective one mentioned above or NaBH₄, AlH₄, or the like), for instance the conversion of —NH₂ to —N(H)-isopropyl by condensation in the presence of acetone (H₃C—C(O)—CH₃) followed by reduction in the presence of a reducing agent such as sodium cyanaoborohydride (i.e. overall a reductive amination);

(v) formation of an amide or sulfonamide, for example by reaction of a sulfonyl chloride with an amine or by an amide coupling reaction, i.e. the formation of an amide from a carboxylic acid (or ester thereof), for example —C(O)OH (or an ester thereof), may be converted to —C(O)N(R¹⁰ᵃ)R¹¹ᵃ group (in which R¹⁰ᵃ and R¹¹ᵃ are as hereinbefore defined, and may be linked together, e.g. as defined above), and which reaction may (e.g. for —COOH) be performed in the presence of a suitable coupling reagent (e.g. 1,1'-carbonyldiimidazole, N,N'-dicyclohexylcarbodiimide, or the like) or, in the case of an ester (e.g. —C(O)OCH$_3$ or —C(O)OCH$_2$CH$_3$), be performed in the presence of e.g. trimethylaluminium, or, alternatively the —C(O)OH group may first be activated to the corresponding acyl halide (e.g —C(O)Cl, by treatment with oxalyl chloride, thionyl chloride, phosphorous pentachloride, phosphorous oxychloride, or the like), and, in all cases, the relevant compound is reacted with a compound of formula HN(R$^{10a}$)R$^{11a}$ (in which R$^{10a}$ and R$^{11a}$ are as hereinbefore defined), under standard conditions known to those skilled in the art (e.g. optionally in the presence of a suitable solvent, suitable base and/or in an inert atmosphere);

(vi) conversion of a primary amide to a nitrile functional group, for example under dehydration reaction conditions, e.g. in the presence of POCl$_3$, or the like;

(vii) nucleophilic substitution (e.g. aromatic nucleophilic substitution) reactions, where any nucleophile replaces a leaving group, e.g. an amine may replace a —S(O)CH$_3$ leaving group;

(viii) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);

(ix) alkylation, acylation or sulfonylation reactions, which may be performed in the presence of base and solvent (such as those described hereinbefore);

(x) specific deprotection steps, such as deprotection of an N-Boc protecting group by reaction in the presence of an acid, or, a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF).

The substituents R$^1$, R$^2$ and R$^3$ (or substituents thereon, e.g. defined by A$^1$, A$^2$, A$^3$, A$^4$, or, Q$^1$, Q$^2$, Q$^3$, Q$^4$, Q$^5$, Q$^6$, Q$^7$, Q$^8$ and/or Q$^9$) in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence. For example, in cases in which there is a —CO$_2$H present, the skilled person will appreciate that at any stage during the synthesis (e.g. the final step), the relevant ester group may be hydrolysed to form a carboxylic acid functional group.

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or a mixture thereof; preferably the reaction is carried out with ammonium hydroxide in a methanol/dimethylformamide mixture, at a temperature ranging from about 50° C. to about 100° C. Analogous operative conditions apply in the preparation of N-substituted or. N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", 3$^{rd}$ edition, T.W. Greene & P.G.M. Wutz, Wiley-Interscience (1999).

Medical and Pharmaceutical Uses

Compounds of the invention are indicated as pharmaceuticals. According to a further aspect of the invention there is provided a compound of the invention, for use as a pharmaceutical.

For the avoidance of doubt, although compounds of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the "active" compounds to which they are metabolised) may therefore be described as "prodrugs" of compounds of the invention.

A "prodrug of a compound of the invention" is as hereinbefore defined, including compounds that form a compound of the invention, in an experimentally-detectable amount, within a predetermined time (e.g. about 1 hour), following oral or parenteral administration. All prodrugs of the compounds of the invention are included within the scope of the invention.

Furthermore, certain compounds of the invention may possess no or minimal pharmacological activity as such, but may be administered parenterally or orally, and thereafter be metabolised in the body to form compounds of the invention that possess pharmacological activity as such. Such compounds (which also includes compounds that may possess some pharmacological activity, but that activity is appreciably lower than that of the "active" compounds of the invention to which they are metabolised), may also be described as "prodrugs".

Thus, the compounds of the invention are useful because they possess pharmacological activity, and/or are metabolised in the body following oral or parenteral administration to form compounds which possess pharmacological activity.

Compounds of the invention may inhibit protein or lipid kinases, such as a PI3 kinase (especially a class I PI3K), for example as may be shown in the tests described below (for example, the test for PI3Kα inhibition described below) and/or in tests known to the skilled person. Thus, the compounds of the invention may be useful in the treatment of those disorders in an individual in which the inhibition of such protein or lipid kinases (e.g. PI3K, particularly Class I PI3K) is desired and/or required.

The term "inhibit" may refer to any measurable reduction and/or prevention of catalytic kinase (e.g. PI3K, particularly class I PI3K) activity. The reduction and/or prevention of kinase activity may be measured by comparing the kinase activity in a sample containing a compound of the invention and an equivalent sample of the kinase (e.g. PI3K, particularly class I PI3K) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein or lipid kinase (e.g. PI3K, such as class I PI3K) at a concentration of 100 µM or below (for example at a concentration of below 50 µM, or even below 10 µM, such as below 1 µM), when tested in an assay (or other test), for example as described hereinafter, or otherwise another suitable assay or test known to the skilled person.

Compounds of the invention are thus expected to be useful in the treatment of a disorder in which a protein or lipid kinase (e.g. PI3K, such as class I PI3K) is known to play a role and which are characterised by or associated with an overall elevated activity of that kinase (due to, for example, increased amount of the kinase or increased catalytic activity of the kinase). Hence, compounds of the invention are expected to be useful in the treatment of a disease/disorder arising from abnormal cell growth, function or behaviour associated with the protein or lipid kinase (e.g. PI3K, such class I PI3K). Such conditions/disorders include cancer, immune disorders, cardiovascular diseases, viral infections (or viral disease), inflammation, metabolism/endocrine function disorders and neurological disorders.

The disorders/conditions that the compounds of the invention may be useful in treating hence includes cancer (such as lymphomas, solid tumours or a cancer as described hereinafter), obstructive airways diseases, allergic diseases, inflammatory diseases (such as asthma, allergy and Chrohn's disease), immunosuppression (such as transplantation rejection and autoimmune diseases), disorders commonly connected with organ transplantation, AIDS-related diseases and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, bone disorders, atherosclerosis, vascular smooth cell proliferation associated with atherosclerosis, pulmonary fibrosis, arthritis glomerulonephritis and post-surgical stenosis and restenosis. Other disease states that may be mentioned include cardiovascular disease, stroke, diabetes, hepatomegaly, Alzheimer's disease, cystic fibrosis, hormone-related diseases, immunodeficiency disorders, destructive bone disorders, infectious diseases, conditions associated with cell death, thrombin-induced platelet aggregation, chronic myelogenous leukaemia, liver disease, pathologic immune conditions involving T cell activation and CNS disorders.

As stated above, the compounds of the invention may be useful in the treatment of cancer. More, specifically, the compounds of the invention may therefore be useful in the treatment of a variety of cancer including, but not limited to: carcinoma such as cancer of the bladder, breast, colon, kidney, liver, lung (including non-small cell cancer and small cell lung cancer), esophagus, gall-bladder, ovary, pancreas, stomach, cervix, thyroid, prostate, skin, squamous cell carcinoma, testis, genitourinary tract, larynx, glioblastoma, neuroblastoma, keratoacanthoma, epidermoid carcinoma, large cell carcinoma, non-small cell lung carcinoma, small cell lung carcinoma, lung adenocarcinoma, bone, adenoma, adenocarcinoma, follicular carcinoma, undifferentiated carcinoma, papilliary carcinoma, seminona, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukaemia; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

Further, the protein or lipid kinases (e.g. PI3K, such as class I PI3K) may also be implicated in the multiplication of viruses and parasites. They may also play a major role in the pathogenesis and development of neurodegenerative disorders. Hence, compounds of the invention may also be useful in the treatment of viral conditions, parasitic conditions, as well as neurodegenerative disorders.

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein) which is associated with the inhibition of protein or lipid kinase (e.g. PI3K, such as class I PI3K) is desired and/or required (for example, a method of treatment of a disease/disorder arising from abnormal cell growth, function or behaviour associated with protein or lipid kinases, e.g. PI3K, such as class I PI3K), which method comprises administration of a therapeutically effective amount of a compound of the invention, as hereinbefore defined but without the provisos, to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that are inhibitors of protein kinases (e.g. PI3K, such as class I PI3K) and/or useful in the treatment of a cancer and/or a proliferative disease. Compounds of the invention may also be combined with other therapies.

According to a further aspect of the invention, there is provided a combination product comprising:
   (A) a compound of the invention, as hereinbefore defined but without the provisos; and
   (B) another therapeutic agent that is useful in the treatment of cancer and/or a proliferative disease,
wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined but without the provisos, another therapeutic agent that is useful in the treatment of cancer and/or a proliferative disease, and a pharmaceutically-acceptable adjuvant, diluent or carrier; and
(2) a kit of parts comprising components:
   (a) a pharmaceutical formulation including a compound of the invention, as hereinbefore defined but without the provisos, in admixture with a pharmaceutically-acceptable adjuvant, diluent or carrier; and
   (b) a pharmaceutical formulation including another therapeutic agent that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

The invention further provides a process for the preparation of a combination product as hereinbefore defined, which process comprises bringing into association a compound of the invention, as hereinbefore defined but without the provisos, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein kinases (e.g. PI3K, such as Class I PI3K).

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

EXAMPLES

Biological Tests

PI3K Activity Assay

The kinase activity was measured by using the commercial ADP Hunter™ Plus assay available from DiscoveR$_x$ (#33-016), which is a homogeneous assay to measure the accumulation of ADP, a universal product of kinase activity. The enzyme, PI3K (p110α/p85α was purchased from Carna Biosciences (#07CBS-0402A). The assay was done following the manufacturer recommendations with slight modifications: Mainly the kinase buffer was replace by 50 mM HEPES, pH 7.5, 3 mM MgCl$_2$, 100 mM NaCl, 1 mM EGTA, 0.04% CHAPS, 2 mM TCEP and 0.01 mg/ml BGG. The PI3K was assayed in a titration experiment to determine the optimal protein concentration for the inhibition assay. To calculate the IC$_{50}$ of the ETP-compounds, serial 1:5 dilutions of the compounds were added to the enzyme at a fixed concentration (2.5 μg/mL. The enzyme was preincubated with the inhibitor and 30 μM PIP$_2$ substrate (P9763, Sigma) for 5 min and then ATP was added to a final 50 μM concentration. Reaction was carried out for 1 hour at 25° C. Reagent A and B were sequentially added to the wells and plates were incubated for 30 min at 37° C. Fluorescence counts were read in a Victor instrument (Perkin Elmer) with the recommended settings (544 and 580 nm as excitation and emission wavelengths, respectively). Values were normalized against the control activity included for each enzyme (i.e., 100% PI3 kinase activity, without compound). These values were plot against the inhibitor concentration and were fit to a sigmoid dose-response curve by using the Graphad software.

EXAMPLES

The compounds names given above were generated with MDL ISIS/DRAW 2.5 SP 2, Autonom 2000.

The following Examples illustrate the invention.

General Experimental Conditions 5-(4,4,5,5-tetramethyl-[1,3,2]dioxaborolan-2-yl)-3-trifluoromethyl-pyridin-2-ylamine was synthesized following the procedure described in WO2008/138834.

HPLC-MS analyses were carried out on an Agilent 1100 Series using ESI+ (or API 2000) for ionization and different brands of RP-C$_{18}$ columns for separation. Analysis of final compounds was performed using a Gemini NX C18 column (100×2.0 mm, 5 um) at a flow rate of 0.8 mL/min and a gradient of 5%-100% of B in 8 min (B=ACN+0.1% formic acid; A=H$_2$O+0.1% formic acid) or as reported. The molecular weight calculated is the isotopic average, and the "found mass" refers to the most abundant isotope detected by LC-MS.

$^1$H NMR spectra were recorded on a Bruker Avance II 300 spectrometer (300 MHz) and are internally referenced to residual solvent peaks. Spectral data for $^1$H NMR are reported in the conventional form: chemical shift (δ ppm), multiplicity (s=singlet, d=doublet, t=triplet, q=quartet, hp=heptaplet, m=multiplet, br=broad), coupling constant (Hz), integration.

Abbreviations: Hereinafter, the term "DCM" means dichloromethane, "CHCl$_3$" means chloroform, "MeOH" means methanol, "EtOH" means ethanol, "EtOAc" means ethyl acetate, "THF" means tetrahydrofuran, "ACN" means acetonitrile, "DMF" means dimethylformamide, "DME" means dimethoxyethane, "DMSO" means dimethylsulfoxide, "Et$_2$O" means diethyl ether, "Hex" means hexane, "EtOAc" means ethyl acetate, "BA/BE" means boronic acid/ester, "Pd(Ph$_3$P)$_2$Cl$_2$" means dichlorobis(triphenylphosphine)palladium(II), "Pd(dppf)Cl$_2$.DCM" means 1,1'-bis(diphenylphosphino)ferrocenepalladium(II) dichloride, dichloromethane complex, "NIS" means N-iodosuccinimde, "Na$_2$SO$_4$" means disodium sulphate, "MgSO$_4$" means magnesium sulphate, "K$_2$CO$_3$" means dipotassium carbonate, "Na$_2$CO$_3$" means disodium carbonate, "NaHCO$_3$" means sodium bicarbonate, "sat." means saturated, "aq." means aqueous, "HPLC" means high performance liquid chromatography, "t$_R$" means retention time, "MS" means mass spectrometry, "TLC" means thin layer chromatography, "R$_f$" means retardation factor, "g" means gram(s), "mmol" means millimole(s), "eq" means equivalent(s), "mL" means milliliter(s), "min" means minute(s), "h" means hour(s), "RT" means room temperature.

Intermediate A

2-Bromo-6-methyl-imidazo[2,1-b][1,3,4]thiadiazole 5-bromo-1,3,4-thiadiazol-2-amine (1 g, 5.55 mmol, 1 eq) and chloroacetone (1.327 mL, 16.665 mmol, 3 eq) in water (24 mL) was stirred at reflux temperature overnight. More chloroacetone (1.106 mL, 13.887 mmol, 2.5 eq) was added, and heating was continued over the weekend. The reaction mixture was cooled to RT, poured into NaHCO$_3$ (sat. sol., 43 mL) and extracted with DCM. The organic extracts were dried (MgSO$_4$), filtered and concentrated to give a dark brown residue that was purified by flash chromatography (SiO$_2$, DCM) affording the desired product (white solid, 0.613 g, 50%). HPLC-MS (10-95% B in 4 min at 0.5 mL+2 min 100% B, flow 0.7 mL/min): t$_R$=4.81 min, [M+H]+ m/z 217.9; $^1$H NMR (300 MHz, CDCl$_3$) δ 7.47 (s, 1H), 2.32 (s, 3H).

Intermediate B 2-(3,4-dimethoxyphenyl)-6-methylimidazo[2,1-b][1,3,4]thiadiazole

To a mixture of 2-bromo-6-methyl-imidazo[2,1-b][1,3,4]thiadiazole (0.550 g, 2.522 mmol, 1 eq), 3,4-dimethoxyphenylboronic acid (0.551 g, 3.026 mmol, 1.2 eq) and Pd(dppf)Cl$_2$.DCM (0.209 g. 0.252 mmol, 0.1 eq) in DME (3 mL) was added K$_2$CO$_3$ (1 mL, sat. aq). The mixture was heated in the microwave oven (130° C., 1 h), cooled to RT, diluted with DCM, washed with water, dried (Na$_2$SO$_4$) and concentrated. The residue (yellow solid, 0.720 g) was purified by automated flash chromatography (SiO$_2$, DCM/0-40% MeOH) to give the desired product (yellow solid, 0.347 g, 50%). HPLC-MS (10-95% B in 4 min at 0.5 mL+2 min 100% B, flow 0.8 mL/min, 50° C.): $t_R$=3.77 min, [M+H]+ m/z 276.1.

Intermediate C 2-(3,4-Dimethoxy-phenyl)-5-iodo-6-methyl-imidazo[2,1-b][1,3,4]thiadiazole 2-(3,4-dimethoxyphenyl)-6-methylimidazo[2,1-b][1,3,4]thiadiazole (0.346 g, 1.257 mmol) was dissolved in DCM (4.2 mL), and NIS (0.283 mg, 1.257 mmol) was added. The reaction mixture was stirred at RT overnight, quenched with sat. aq. thiosulfate and extracted with DCM. The organic layers were combined and washed with sat. aq. $NH_4Cl$, dried ($MgSO_4$), filtered and concentrated. The residue was suspended in $Et_2O$, and the solid was filtered off, washed with $Et_2O$ and dried in vacuo affording the desired product (brown solid (0.295 g, 58%). TLC (cyclohexane/EtOAc 1:1) $R_f$0.46; HPLC-MS (10-95% B in 4 min at 0.5 mL+2 min 100% B, flow 0.8 mL/min, 50° C.): $t_R$=4.53 min, [M+H]+ m/z 402.0; $^1$H NMR (300 MHz, $CDCl_3$) δ/ppm 7.37 (s, 1H), 7.32 (d, J=8.3, 1H), 6.86 (d, J=8.3, 1H), 3.91 (d, J=14.3, 6H), 2.31 (s, 3H).

Example 1

2-(3,4-Dimethoxy-phenyl)-5-(3-fluoro-4-methanesulfonyl-phenyl)-6-methyl-imidazo[2,1-b][1,3,4]thiadiazole To a suspension of 2-(3,4-dimethoxy-phenyl)-5-iodo-6-methyl-imidazo[2,1-b][1,3,4]thiadiazole (0.035 g, 0.087 mmol, 1 eq) in dioxane (1.8 mL), 3-fluoro-4-(methylsulfonyl)phenylboronic acid (0.047 g, 0.217 mmol, 2.5 eq), $Pd(Ph_3P)_2Cl_2$ (0.006 g, 0.0087 mmol, 0.1 eq), potassium carbonate (0.06 g, 0.435 mmol, 5 eq) and water (0.8 mL) were added. The reaction mixture was subjected to MW irradiation (120° C., 35 min, 200 W), cooled to RT and concentrated. The residue was purified by silica gel chromatography (0-0.5% MeOH in DCM). Product fractions afforded an oily residue that was further purified by trituration with $Et_2O$ providing a pale yellow solid (0.02 g) and by preparative HPLC to give the pure product (0.010 g, 25%). HPLC-MS: (50-100% B in 8 min, 0.6 mL/min): $t_R$=2.41 min, [M+H]+ m/z 448.1. $^1$H NMR (300 MHz, $CDCl_3$) δ/ppm 8.03 (dd, J=8.3, 7.7, 1H), 7.81-7.70 (m, 2H), 7.39 (dt, J=3.4, 2.0, 2H), 6.94 (d, J=8.2, 1H), 3.96 (s, 3H), 3.94 (s, 3H), 3.26 (s, 3H), 2.59 (s, 3H).

Example 2

5-[2-(3,4-Dimethoxy-phenyl)-6-methyl-imidazo[2,1-b][1,3,4]thiadiazol-5-yl]-pyridine-2-carbonitrile A mixture of 2-(3,4-dimethoxy-phenyl)-5-iodo-6-methyl-imidazo[2,1-b][1,3,4]thiadiazole (0.125 g, 0.312 mmol, 1 eq), 2-cyanopyridine-5-boronic acid pinacol ester (0.095 g, 0.414 mmol, 1.33 eq), $Pd(dppf)Cl_2.DCM$ (0.008 g, 0.009 mmol, 0.03 eq) and cesium carbonate (0.305 g, 0.935 mmol, 3 eq) in DME (4 mL) and water (0.1 mL) was heated in the microwave oven (45 min, 130° C.), cooled to RT, diluted with water, extracted with EtOAc and washed with brine. The organic layers were dried (MgSO4), filtered and concentrated, and the residue was purified by silica gel chromatography (0-100% DCM in hexane, then 0-3% MeOH in DCM). Product fractions were concentrated to give a solid that was further purified by preparative HPLC affording the pure product (0.002 g, 2% yield). HPLC-MS: (5-100% B in 8 min, 0.8 mL/min): $t_R$=5.52 min, [M+H]+ m/z 378.1. $^1$H NMR (300 MHz, $CDCl_3$) δ/ppm 9.16 (d, J=1.5, 1H), 8.18 (dd, J=8.4, 2.2, 1H), 7.82-7.67 (m, 1H), 7.41-7.28 (m, 2H), 6.89 (d, J=8.4, 0H), 3.91 (s, 3 H), 3.89 (s, 3 H), 2.54 (s, 1H).

Example 3

5-[2-(3,4-Dimethoxy-phenyl)-6-methyl-imidazo[2,1-b][1,3,4]thiadiazol-5-yl]-3-trifluoromethyl-pyridin-2-ylamine A mixture of 2-(3,4-dimethoxy-phenyl)-5-iodo-6-methyl-imidazo[2,1-b][1,3,4]thiadiazole (0.125 g, 0.312 mmol, 1 eq), 5-(4,4,5,5-tetramethyl-[1,3,2]dioxaborolan-2-yl)-3-trifluoromethyl-pyridin-2-ylamine (0.119 g, 0.414 mmol, 1.33 eq), $Pd(dppf)Cl_2.DCM$ (0.008 g, 0.009 mmol, 0.03 eq) and cesium carbonate (0.305 g, 0.935 mmol, 3 eq) in DME (4 mL) and water (0.1 mL) was heated in the microwave oven (45 min, 130° C.), cooled to RT, diluted with water, extracted with EtOAc and washed with brine. The organic layers were dried ($MgSO_4$), filtered and concentrated, and the residue was purified by silica gel chromatography (0-100% EtOAc in hexane). Product fractions were concentrated and triturated with $Et_2O$, the solid was filtered off and dried to give the desired product (solid, 0.070 g, 52%). HPLC-MS: (50-100% B in 8 min, 0.8 mL/min): $t_R$=1.11 min, [M+H]+ m/z 436.0. $^1$H NMR (300 MHz, $CDCl_3$) δ/ppm 8.62 (d, J=1.6, 1H), 8.22 (d, J=1.6, 0H), 7.44 (d, J=2.2, 1H), 7.39 (dd, J=8.2, 2.2, 1H), 6.96 (d, J=8.5, 1H), 5.11 (s, 1H), 3.99 (s, 3H), 3.97 (s, 3H), 2.53 (s, 1H).

Example 4

2-(3,4-Dimethoxy-phenyl)-6-methyl-5-pyridin-3-yl-imidazo[2,1-b][1,3,4]thiadiazole A mixture of 2-(3,4-dimethoxy-phenyl)-5-iodo-6-methyl-imidazo[2,1-b][1,3,4]thiadiazole (0.070 g, 0.174 mmol), pyridine-3-boronic acid (0.026 g, 0.209 mmol), $Pd(dppf)Cl_2.DCM$ (0.014 g. 0.017 mmol) and potassium carbonate (0.5 mL, sat. aq) in DME (1.7 mL) was heated in the microwave oven at 150° C. for 2 h. Since the conversion was incomplete, another 1.2 eq of pyridine-3-boronic acid and 0.1 eq of $Pd(dppf)Cl_2.DCM$ were added, and the mixture was subjected to another 7 hours of microwave irradiation at 150° C. The reaction mixture was cooled, diluted with DCM, washed with water, dried ($Na_2SO_4$) and concentrated. A yellow solid (0.055 g) was obtained that was purified by silica gel chromatography (cyclohexane/0-60% EtOAc) to give the desired product (white solid, 0.042 g, 39%). HPLC-MS: (5-100% B in 8 min, 0.8 mL/min, 50° C.): $t_R$=4.09 min, [M+H]+ m/z 353.1. $^1$H NMR (300 MHz, $CDCl_3$) δ/ppm 9.00 (d, J=2.2, 1H), 8.53 (dd, J=4.8, 1.6, 1H), 8.00 (dd, J=8.0, 1.8, 1H), 7.48-7.29 (m, 3H), 6.88 (d, J=9.0, 1H), 3.90 (d, J=5.0, 7H), 2.50 (s, 3H).

Example 5

2-(3,4-Dimethoxy-phenyl)-5-(6-methoxy-pyridin-3-yl)-6-methyl-imidazo[2,1-b][1,3,4]thiadiazole A mixture of 2-(3,4-dimethoxy-phenyl)-5-iodo-6-methyl-imidazo[2,1-b][1,3,4]thiadiazole (0.10 g, 0.249 mmol), 2-methoxy-5-pyridineboronic acid (0.046 g, 0.299 mmol), $Pd(dppf)Cl_2.DCM$ (0.021 g. 0.025 mmol) and potassium carbonate (0.7 mL, sat. aq) in DME (2.5 mL) was heated in a sealed tube at 130° C. for 5 h. The reaction mixture was cooled, diluted with DCM, washed with water, dried (Na$_2$SO$_4$) and concentrated. A yellow solid (0.120 g) was obtained that was purified by silica gel chromatography (DCM/0-40% MeOH) to give a brown solid (0.080 g). A second chromatography (SiO$_2$, cyclohexane/0-60% EtOAc) yielded pure product (white solid, 0.056 g, 59%). TLC (SiO$_2$, cyclohexane/EtOAc 1:2) R$_f$=0.19; HPLC-MS: (5-100% B in 8 min, 0.8 mL/min, 50° C.): t$_R$=5.58 min, [M+H]+ m/z 383.1. $^1$H NMR (300 MHz, CDCl$_3$) δ/ppm 8.48 (d, J=2.1, 1H), 7.88 (dd, J=8.7, 2.4, 1H), 7.39-7.23 (m, 2H), 6.88 (dt, J=17.3, 8.7, 2H), 4.01-3.80 (m, 9H), 2.52-2.31 (m, 3H).

Example 6

2,5-Bis-(3,4-dimethoxy-phenyl)-6-methyl-imidazo [2,1-b][1,3,4]thiadiazole

A mixture of 2-(3,4-dimethoxy-phenyl)-5-iodo-6-methyl-imidazo[2,1-b][1,3,4]thiadiazole (0.070 g, 0.174 mmol), 3,4-dimethoxyphenylboronic acid (0.038 g, 0.209 mmol), Pd(dppf)Cl$_2$.DCM (0.014 g. 0.017 mmol) and potassium carbonate (0.5 mL, sat. aq) in DME (1.7 mL) was heated in the microwave oven at 150° C. for 2 h. The reaction mixture was cooled, diluted with DCM, washed with water, dried (Na$_2$SO$_4$) and concentrated. A yellow solid (0.054 g) was obtained that was purified by silica gel chromatography (cyclohexane/0-60% EtOAc) to give the desired product (white solid, 0.030 g, 42%). TLC (SiO$_2$, cyclohexane/EtOAc 1:2) R$_f$=0.20; HPLC-MS: (5-100% B in 8 min, 0.8 mL/min, 50° C.): t$_R$=5.47 min, [M+H]+ m/z 412.1; $^1$H NMR (300 MHz, CDCl$_3$) δ/ppm 7.32 (dd, J=7.9, 5.6, 3H), 6.91 (dd, J=23.2, 8.3, 2H), 3.94-3.81 (m, 13H), 2.47 (s, 3H).

Example 7

5-[2-(3,4-Dimethoxy-phenyl)-6-methyl-imidazo[2,1-b][1,3,4]thiadiazol-5-yl]-pyrimidin-2-ylamine A mixture of 2-(3,4-dimethoxy-phenyl)-5-iodo-6-methyl-imidazo[2,1-b][1,3,4]thiadiazole (0.041 g, 0.102 mmol, 1 eq), 5-(4,4,5,5-tetramethyl-1,3,2-dioxaborolan-2-yl)pyrimidin-2-amine (0.056 g, 0.255 mmol, 2.5 eq), Pd(Ph$_3$P)$_2$Cl$_2$ (0.007 g, 0.0102 mmol, 0.1 eq) and potassium carbonate (0.07 g, 0.51 mmol, 5 eq) in water (0.3 mL) and dioxane (2.2 mL) was subjected to MW irradiation (120° C., 35 min, 200 W). The solvents were evaporated, and the residue obtained was purified by silica gel chromatography (0-3% MeOH in DCM) and preparative HPLC (RP-C18, ACN/water) to give the desired product (0.012 g). HPLC-MS: (5-100% B in 8 min, 0.8 mL/min, 50° C.): t$_R$=4.08 min, [M+H]+ m/z 369.1

Example 8

5-[2-(3,4-Dimethoxy-phenyl)-6-methyl-imidazo[2,1-b][1,3,4]thiadiazol-5-yl]-pyridin-2-ol A solution of 2-(3,4-dimethoxy-phenyl)-5-(6-methoxy-pyridin-3-yl)-6-methyl-imidazo[2,1-b][1,3,4]thiadiazole (0.028 g, 0.073 mmol, 1 eq) in 25% HCl (0.75 mL) was subjected to microwave irradiation (95° C., 2 h, 200 W). The reaction mixture was cooled to RT, neutralized with NaHCO$_3$ (sat. sol) and extracted with EtOAc and subsequently with CH$_2$Cl$_2$/MeOH (9:1). The organic phase was dried (MgSO$_4$), filtered and concentrated. The crude (0.007 g) was purified by preparative HPLC (RP-C18, ACN/water) affording the desired product (yellowish solid, 0.005 g, 19%). HPLC-MS: (5-100% B in 8 min, 0.8 mL/min, 50° C.): t$_R$=3.94 min, [M+H]+ m/z 369.1; $^1$H NMR (300 MHz, CDCl$_3$) δ/ppm 12.94 (s, 2H), 7.82 (dd, J=9.5, 2.5, 1H), 7.72 (d, J=2.2, 1H), 7.34 (dd, J=8.3, 2.0, 1H), 7.30 (d, J=2.0, 1H), 6.88 (d, J=8.4, 1H), 6.69 (d, J=9.5, 1H), 3.92 (s, 3H), 3.89 (s, 3H), 2.40 (s, 3H).

Intermediate D

2-Methoxy-4-(6-methylimidazo[2,1-b][1,3,4]thiadia-zol-2-yl)phenol

To a solution of 2-bromo-6-methyl-imidazo[2,1-b][1,3,4]thiadiazole (1.53 g, 7.02 mmol, 1 eq) in dioxane (30 mL), 2-methoxy-4-(4,4,5,5-tetramethyl-1,3,2-dioxaborolan-2-yl)phenol (1.76 g, 7.02 mmol, 1 eq) was added followed by 2M aq. Na$_2$CO$_3$ (15 mL, 30 mmol, 4.3 eq). The suspension was degassed (N$_2$, 15 min) and equipped with an argon balloon. Pd(Ph$_3$P)$_2$Cl$_2$ (1.23 g, 1.75 mmol, 0.25 eq) was quickly added, and the reaction flask was placed in a pre-heated bath (115° C.). After stirring at reflux temperature for 2 h the reaction mixture was cooled to RT and concentrated. The residue was taken in water and extracted with DCM; the organic phase was washed with water, dried and concentrated to give 2-methoxy-4-(6-methylimidazo[2,1-b][1,3,4]thiadiazol-2-yl)phenol as a crude product (brown solid, 3 g) that was used in the next step without further purification. HPLC-MS (10-95% B in 4 min +2 min 100% B, flow 0.5 mL/min, 50° C.): t$_R$=3.27 min, [M+H]+ m/z 262.0

Intermediate E 4-(5-iodo-6-methylimidazo[2,1-b][1,3,4]thiadiazol-2-yl)-2-methoxyphenol The crude material from the previous step was dissolved in dry DMF (25 mL), and NIS (1.7 g, 7.7 mmol, 1.1 eq) was added. The reaction mixture was stirred at RT for 15 h and then concentrated. The residue was partitioned between DCM and water containing some aq. sodium thiosulfate. The organic phase was separated, dried (MgSO$_4$) and concentrated yielding a black oil that was triturated with Et$_2$O. The solid was filtered off and dried in vacuo affording the desired product as a light-brown solid (0.73 g). HPLC-MS (10-95% B in 4 min+2 min 100% B, flow 0.5 mL/min, 50° C.): t$_R$=3.99 min (50% purity), [M+H]+ m/z 387.9.

Intermediate F 4-(5-(6-amino-5-(trifluoromethyl)pyridin-3-yl)-6-methylimidazo[2,1-b][1,3,4]thiadiazol-2-yl)-2-methoxyphenol A mixture of 6-(3,4-dimethoxy-phenyl)-3-iodo-2-methyl-imidazo[1,2-b]pyridazine (crude material from previous step, 0.72 g, 1.8 mmol, 1.0 eq), 5-(4,4,5,5-tetramethyl-[1,3,2]di-oxaborolan-2-yl)-3-trifluoromethyl-pyridin-2-ylamine (0.70 g, 2.42 mmol, 1.3 eq), Pd(dppf)Cl$_2$.DCM (0.31 g, 0.37 mmol, 0.20 eq) and Cs$_2$CO$_3$ (1.80 g, 5.59 mmol, 3.0 eq) in DME (20 mL) and water (4 mL) was degassed (Ar), kept under Ar and heated in a two-necked round bottom flask fitted with a reflux condenser (3 h, 115° C.). Once conversion was complete, the reaction mixture was cooled to RT, and the pH was adjusted to 7 by adding an aqueous saturated solution of NH$_4$Cl. The solvents were evaporated, and the residue was taken up in water and extracted with DCM (3×). The combined organic layers were dried (MgSO$_4$), filtered and concentrated in vacuo. The crude (0.9 g) was adsorbed onto silica and purified by column chromatography (SiO$_2$, DCM/MeOH) yielding the desired product (brown solid, 0.143 g, 0.34 mmol, 5% yield, 3 steps). A small amount was further purified by preparative HPLC (RP-C18, ACN/water) and trituration with Et₂O. HPLC-MS: (10-95% B in 4 min, 0.5 mL/min+2 min 100% B, 0.8 mL/min): $t_R$=3.99 min, [M+H]+ m/z 422.1; ¹HNMR (300 MHz, MeOD) δ/ppm ¹H NMR (300 MHz, MeOD) δ 8.42 (s, 1H), 8.09 (s, 1H), 7.73-7.65 (m, 1H), 7.51-7.39 (m, 2H), 4.07-3.93 (m, 4H), 2.40-2.25 (m, 3H).

Example 9 tert-Butyl 2-(4-(5-(6-amino-5-(trifluoromethyl)pyridin-3-yl)-6-methylimidazo-[2,1-b][1,3,4]thiadiazol-2-yl)-2-methoxyphenoxy)ethylcarbamate To a solution of 4-(5-(6-amino-5-(trifluoromethyl)pyridin-3-yl) -6-methylimidazo[2,1-b][1,3,4]thiadiazol-2-yl)-2-methoxyphenol (0.030 g, 0.07 mmol, 1 eq) in dry DMF (0.8 mL), tert-butyl 2-bromoethylcarbamate (0.020 g, 0.09 mmol, 1.25 eq) and K₂CO₃ (0.01 g, 0.09 mmol, 1.25 eq) were added. The mixture was stirred at 105° C. for 2 h and cooled to RT. The solvent was evaporated, and the dry residue was taken up in DCM, washed with water (2×1 mL), dried (MgSO4), filtered and concentrated to dryness. Purification by preparative HPLC (RP-C18, ACN/water) gave the desired product (0.006 g, 15%). HPLC-MS: (50-100% B in 8 min, 0.8 mL/min): $t_R$=1.75 min, [M+H]+ m/z 565; ¹H NMR (300 MHz, CDCl₃) δ/ppm 8.42 (d, J=1.7, 1H), 7.95 (d, J=1.8, 1H), 7.49 (s, 1H), 7.41 (t, J=2.5, 1H), 7.32 (t, J=4.5, 1H), 5.19 (s, 2H), 5.01 (s, 1H), 3.99 (s, 3H), 3.48-3.43 (m, 2H), 2.40-2.32 (m, 3H), 2.19-2.07 (m, 8H), 1.98 (s, 3H).

Example 10

2-(4-(5-(6-amino-5-(trifluoromethyl)pyridin-3-yl)-6-methylimidazo[2,1-b][1,3,4]thiadiazol-2-yl)-2-methoxyphenoxy)-N,N-dimethylacetamide To a solution of 4-(5-(6-amino-5-(trifluoromethyl)pyridin-3-yl) -6-methylimidazo[2,1-b][1,3,4]thiadiazol-2-yl)-2-methoxyphenol (0.042 g, 0.1 mmol, 1 eq) in dry DMF (1 mL), 2-chloro-N,N-dimethylacetamide (0.016 g, 0.13 mmol, 1.25 eq) and K₂CO₃ (0.018 g, 0.13 mmol, 1.25 eq) were added. The mixture was stirred at 105° C. for 1 h and cooled to RT. The solvent was evaporated, and the dry residue was taken up in DCM, washed with water (2×1 mL), dried (MgSO4), filtered and concentrated to dryness. Purification by preparative HPLC (RP-C18, ACN/water) and trituration with Et₂O gave the desired product. HPLC-MS: (5-100% B in 8 min, 0.8 mL/min): $t_R$=4.68 min, [M+H]+ m/z 507.1; ¹H NMR (300 MHz, CDCl₃) δ 8.41 (d, J=1.7, 1H), 7.95 (d, J=1.8, 1H), 7.49 (s, 1H), 7.42 (d, J=2.1, 1H), 7.29 (d, J=2.1, 1H), 5.12-5.01 (m, 2H), 4.57 (d, J=9.2, 2H), 4.03-3.90 (m, 3H), 3.47 (s, 2H), 2.92 (s, 3H), 2.82 (s, 3H), 2.37 (d, J=0.6, 3H).

Example 11

5-(2-(4-(2-morpholinoethoxy)-3-methoxyphenyl)-6-methylimidazo[2,1-b][1,3,4]thiadiazol-5-yl)-3-(trifluoromethyl)pyridin-2-amine To a solution of 4-(5-(6-amino-5-(trifluoromethyl)pyridin-3-yl) -6-methylimidazo[2,1-b][1,3,4]thiadiazol-2-yl)-2-methoxyphenol (0.042 g, 0.1 mmol, 1 eq) in dry DMF (1 mL), 4-(2-chloroethyl)morpholine hydrochloride (0.024 g, 0.13 mmol, 1.25 eq), iPr₂EtN (0.021 mL, 0.13 mmol, 1.3 eq) and K₂CO₃ (0.018 g, 0.13 mmol, 1.25 eq) were added. The mixture was stirred at 105° C. for 1 h and cooled to RT. The solvent was evaporated, and the dry residue was taken up in DCM, washed with water (2×1 mL), dried (MgSO4), filtered and concentrated to dryness. Purification by reversed-phase chromatography (RP-C18, ACN/water) using a pre-packed cartridge and, subsequently, preparative HPLC gave the desired product. HPLC-MS: (5-100% B in 8 min, 0.6 mL/min): $t_R$=3.3 min, [M+H]+ m/z 534.1; ¹H NMR (300 MHz, CDCl₃) δ/ppm 8.44 (d, J=1.7, 1H), 7.98 (d, J=1.8, 1H), 7.49 (d, J=0.8, 1H), 7.41 (d, J=2.0, 1H), 7.31 (d, J=2.1, 1H), 5.07 (s, 2H), 4.01-3.89 (m, 6H), 3.69-3.59 (m, 4H), 3.47 (s, 3H), 2.62-2.51 (m, 3H), 2.38 (dd, J=9.0, 2.7, 7H).

Intermediate G

2-Bromoimidazo[2,1-b][1,3,4]thiadiazole

To a suspension of 5-bromo-1,3,4-thiadiazol-2-amine (60 g, 0.33 mol) in H₂O (1.5 L), a solution of chloroacetaldehyde (50% wt in water, 64.5 mL, 0.50 mol) was added, and the mixture was stirred at reflux temperature for 5 h. A second portion of chloroacetaldehyde (20.6 mL, 0.5 eq) was added, and stirring was continued overnight. The starting material had been consumed completely, and the reaction mixture was cooled to RT. The solid was removed by filtration and washed with water. The mother liquor was neutralized with a sat. aq. solution of NaHCO₃ and extracted with DCM (2×1 L). The organic layers were washed with brine (2×600 mL), dried and evaporated in vacuo. The brown residue obtained was triturated with a mixture of MeOH and MTBE (1:1, 70 mL) to afford the desired product as a pale yellow solid. The mother liquors were purified by chromatography (SiO₂, DCM) to yield some more product. Combined yield: 9.4 g (14%). MS (ESI⁺): m/z=204 [M+H]⁺; ¹H-NMR(CDCl₃): 7.36 (d, 1H); 7.56 (d, 1H).

Intermediate H 2-bromo-5-iodoimidazo[2,1-b][1,3,4]thiadiazole

NIS (3.83 g, 16.2 mmol, 1.1 eq) was added to a solution of 2-bromo-imidazo[2,1-b][1,3,4]thiadiazole (3.0 g, 14.7 mmol, 1 eq) in dry DMF (50 mL). The mixture was stirred at RT for 4 h and then poured into aq. Na₂S₂O₃ (10%) and diluted with EtOAc. The organic phase was washed with water, dried and concentrated to give the desired product (pale brown solid; 4.34 g, yield 89%). ¹H (300 MHz, CDCl₃): δ/ppm 7.29 (1H, s).

Intermediate I

4-[2-Methoxy-4-(4,4,5,5-tetramethyl-[1,3,2]dioxaborolan-2-yl)-phenoxy]-piperidine-1-carboxylic acid tert-butyl ester To a solution of 2-methoxy-4-(4,4,5,5-tetramethyl-1,3,2-dioxaborolan-2-yl)phenol (0.8 g, 3.2 mmol, 1 eq), 1-boc-4-hydroxypiperidine (0.97 g, 4.8 mmol, 1.5 eq) and triphenylphosphine (1.26 g, 4.8 mmol, 1.5 eq) in anhydrous THF (8 mL) was added DIAD (0.94 mL, 4.8 mmol, 1.5 eq) dropwise at 0° C. The solution was stirred at RT for 45 h. The solvent was removed, and the resulting light orange oily residue was treated with 20% AcOEt/c-hexane to give white crystals (PPh₃O) which were filtered off and washed with the same mixture. The filtrate was evaporated to give an oily residue which was treated with c-hexane and a few drops of AcOEt to give a white precipitate that was removed by filtration and an oily residue that solidified upon standing. The crude product (1.93 g containing some c-hexane) was used as it was in the subsequent step. The remainder was purified by column chromatography (Isolute Flash Si II column, 25 g silica gel, 0-8% AcOEt in c-hexane) to give the pure desired product (0.991 g). HPLC-MS (10-95% B in 4 min at 0.5 mL+2 min 100% B, flow 0.8 mL/min, 50° C.): $t_R$=5.10 min, [M+H]+ m/z 334.3.

Intermediate J

4-[4-(5-Iodo-imidazo[2,1-b][1,3,4]thiadiazol-2-yl)-2-methoxy-phenoxy]-piperidine-1-carboxylic acid tert-butyl ester To a suspension of 2-bromo-5-iodoimidazo[2,1-b][1,3,4]thiadiazole (0.262 g, 0.794 mmol, 1 eq) in 1,4-dioxane (13 mL), 4-[2-Methoxy-4-(4,4,5,5-tetramethyl-[1,3,2]dioxaborolan-2-yl)-phenoxy]-piperidine-1-carboxylic acid tert-butyl ester (0.413 g, 0.953 mmol, 1.2 eq), $Cs_2CO_3$ (0.517 g, 1.588 mmol, 2 eq), dichlorobis(triphenylphosphine)palladium(II) (0.056 g, 0.079 mmol, 0.1 eq) and water (6 ml) were added. The resulting mixture was heated at 115° C. overnight. Solvents were removed and the crude was purified in an (solute Flash Si II column (25 g silica gel, 10%-21% EtOAc in c-hexane) to give the desired product (0.21 g). HPLC-MS (10-95% B in 4 min at 0.5 mL+2 min 100% B, flow 0.8 mL/min, 50° C.): $t_R$=4.98 min, [M+H]+ m/z 557.1.

Intermediate K

4-{4-[5-(6-Amino-5-trifluoromethyl-pyridin-3-yl)-imidazo[2,1-b][1,3,4]thiadiazol-2-yl]-2-methoxy-phenoxy}-piperidine-1-carboxylic acid tert-butyl ester A mixture of 4-[4-(5-iodo-imidazo[2,1-b][1,3,4]thiadiazol-2-yl)-2-methoxy-phenoxy]-piperidine-1-carboxylic acid tert-butyl ester (94 mg, 0.169 mmol, 1 eq), 5-(4,4,5,5-tetramethyl-[1,3,2]dioxaborolan-2-yl)-3-trifluoromethyl-pyridin-2-ylamine (73 mg, 0.253 mmol, 1.5 eq), 1,4-dioxane (5 ml), $K_2CO_3$ (70 mg, 0.507 mmol, 3 eq), $H_2O$ (2 ml) and $Pd(PPh_3)_2Cl_2$ (12 mg, 0.0169 mmol, 0.1 eq) was heated under microwave irradiation (120° C., 30 min). Solvents were removed and the residue was partitioned between $H_2O$ and EtOAc. The organic layer was dried, filtered and evaporated. The residue was purified in an Isolute Flash Si II column (10-25% EtOAc in c-hexane and 20% MeOH in DCM) and by HPLC-prep to give the desired product (7 mg) as a yellow solid. The aqueous phase was further extracted with MeOH/DCM 1:9, the organic layers were dried, filtered and evaporated. The residue was triturated with MeOH/DMSO, filtered and washed with $CH_3CN$ to give the desired product (18 mg, overall yield: 25%). HPLC-MS (5-100% B in 8 min at 0.8 mL): $t_R$=2.95 min, [M+H]+ m/z 591.2; $^1$H NMR (300 MHz, DMSO) δ 8.86 (d, J=1.8 Hz, 1H), 8.43 (d, J=2.1 Hz, 1H), 7.77 (s, 1H), 7.49 (m, 2H), 7.27 (d, J=9.2 Hz, 1H), 6.73 (s, 2H), 4.67 (m, 1H), 3.89 (s, 3H), 3.68 (m, 2H), 3.21 (m, 2H), 1.92 (m, 2H), 1.57 (m, 2H), 1.41 (s, 9H).

Example 12

5-{2-[3-Methoxy-4-(piperidin-4-yloxy)-phenyl]-imidazo[2,1-b][1,3,4]thiadiazol-5-yl}-3-trifluoromethyl-pyridin-2-ylamine 4-{4-[5-(6-Amino-5-trifluoromethyl-pyridin-3-yl)-imidazo[2,1-b][1,3,4]thiadiazol-2-yl]-2-methoxy-phenoxy}-piperidine-1-carboxylic acid tert-butyl ester (23 mg; 0.039 mmol; 1 eq) was suspended in anhydrous DCM (3 ml) and 4M HCl in 1,4-dioxane (0.097 ml, 0.39 mmol, 10 eq) was added. The reaction mixture was stirred at RT overnight. The solvents were removed and the residue was co-evaporated with DCM (×3). The residue was triturated in $CH_3CN$ and filtered to give the desired product as HCl salt (19 mg, 92%). HPLC-MS (5-100% B in 8 min at 0.8 mL): $t_R$=3.25 min, [M+H]+ m/z 491.2; $^1$H NMR (300 MHz, DMSO) δ 9.10 (s, 2H), 8.88 (s, 1H), 8.49 (d, J=1.6 Hz, 1H), 7.87 (s, 1H), 7.53 (m, 2H), 7.31 (d, J=9.1 Hz, 1H), 4.76 (s, 1H), 3.91 (s, 3H), 3.17 (m, 2H), 3.09 (m, 2H), 2.12 (m, 2H), 1.90 (m, 2H).

Intermediate L

4-{2-Methoxy-4-[5-(6-methoxy-pyridin-3-yl)-imidazo[2,1-b][1,3,4]thiadiazol-2-yl]-phenoxy}-piperidine-1-carboxylic acid tert-butyl ester A mixture of 4-[4-(5-iodo-imidazo[2,1-b][1,3,4]thiadiazol-2-yl)-2-methoxy-phenoxy]-piperidine-1-carboxylic acid tert-butyl ester (94 mg, 0.169 mmol, 1 eq), 2-methoxy-5-pyridineboronic acid (39 mg, 0.253 mmol, 1.5 eq), EtOH (5 ml), $Et_3N$ (0.070 ml, 0.507 mmol, 3 eq) and $Pd(PPh_3)_2Cl_2$ (12 mg, 0.0169 mmol, 0.1 eq) was heated under microwave irradiation (120° C., 30 min). The solvents were removed under reduced pressure and the residue was treated with $Et_2O$. The filtrate was evaporated and the residue was purified by HPLC to give the desired product (12 mg; 13%) as a colourless oil. HPLC-MS (5-100% B in 8 min at 0.8 mL): $t_R$=3.30 min, [M+H]+ m/z 538.3; $^1$H NMR (300 MHz, $CD_3COCD_3$) δ 8.87 (m, 1H), 8.28 (dd, J=8.7, 2.5 Hz, 1H), 7.64 (s, 1H), 7.59 (d, J=2.1 Hz, 1H), 7.54 (dd, J=8.4, 2.2 Hz, 1H), 7.24 (d, J=8.4 Hz, 1H), 6.89 (dd, J=8.7, 0.7 Hz, 1H), 4.71 (m, 1H), 3.96 (s, 3H), 3.93 (s, 3H), 3.75 (m, 2H), 3.32 (m, 2H), 1.98 (m, 2H), 1.70 (m, 2H), 1.45 (s, 9H).

Example 13

2-[3-Methoxy-4-(piperidin-4-yloxy)-phenyl]-5-(6-methoxy-pyridin-3-yl)-imidazo[2,1-b][1,3,4]thiadiazole 4-{2-Methoxy-4-[5-(6-methoxy-pyridin-3-yl)-imidazo[2,1-b][1,3,4]thiadiazol-2-yl]-phenoxy}-piperidine-1-carboxylic acid tert-butyl ester (11 mg; 0.0204 mmol; 1 eq) was dissolved in anhydrous DCM (1 ml) and 4M HCl (0.051 ml, 0.204 mmol, 10 eq) was added. The reaction mixture was stirred at RT for 2 h. The excess of acid was co-evaporated with DCM (×3) to give the desired product (9 mg, 100%) as a white solid. HPLC-MS (5-100% B in 8 min at 0.8 mL): $t_R$=3.24 min, [M+H]+ m/z 438.2; $^1$H NMR (300 MHz, MeOD) δ 8.98 (s, 1H), 8.54 (m, 1H), 8.25 (m, 1H), 7.66 (m, 2H), 7.28 (m, 2H), 4.76 (m, 1H), 4.10 (s, 3H), 3.94 (s, 3H), 3.45 (m, 2H), 3.21 (m, 2H), 2.17 (m, 4H).

Example 14

4-{4-[5-(2-Amino-pyrimidin-5-yl)-imidazo[2,1-b][1,3,4]thiadiazol-2-yl]-2-methoxy-phenoxy}-piperidine-1-carboxylic acid tert-butyl ester A mixture of 4-[4-(5-iodo-imidazo[2,1-b][1,3,4]thiadiazol-2-yl)-2-methoxy-phenoxy]-piperidine-1-carboxylic acid tert-butyl ester (82 mg, 0.147 mmol, 1 eq), 2-aminopyrimidine-5-boronic acid pinacol ester (48 mg, 0.22 mmol, 1.5 eq), 1,4-dioxane (4 mL), $K_2CO_3$ (61 mg, 0.441 mmol, 3 eq), $H_2O$ (1.6 ml) and Pd(PPh$_3$)$_2$Cl$_2$ (10 mg, 0.0147 mmol, 0.1 eq) was heated under microwave irradiation (120° C., 30 min). Solvents were removed and the residue was purified in an Isolute Flash Si II column (0-3% MeOH in DCM). The product obtained was triturated with EtOAc and filtered. The filtrate was evaporated and the residue was triturated with acetone. The filtrate was evaporated. The residue was purified by column chromatography (EtOAc) to give the desired product (11 mg, 14%). HPLC-MS (5-100% B in 8 min at 0.8 mL): $t_R$=5.90 min, [M+H]+ m/z 524.2; $^1$H NMR (300 MHz, CDCl$_3$) δ 8.86 (s, 2H), 7.43 (m, 2H), 7.36 (dd, J=8.3, 2.1 Hz, 1H), 6.96 (d, J=8.4 Hz, 1H), 5.26 (s, 2H), 4.53 (m, 1H), 3.93 (s, 3H), 3.75 (m, 2H), 3.29 (m, 2H), 1.93 (m, 2H), 1.81 (m, 2H), 1.45 (s, 9H).

Example 15

5-{2-[3-Methoxy-4-(piperidin-4-yloxy)-phenyl]-imidazo[2,1-b][1,3,4]thiadiazol-5-yl}-pyrimidin-2-ylamine 4-{4-[5-(2-Amino-pyrimidin-5-yl)-imidazo[2,1-b][1,3,4]thiadiazol-2-yl]-2-methoxy-phenoxy}-piperidine-1-carboxylic acid tert-butyl ester (9 mg; 0.017 mmol; 1 eq) was dissolved in anhydrous DCM (1 mL) and 4M HCl in 1,4-dioxane (0.042 ml, 0.17 mmol, 10 eq) was added. The reaction mixture was stirred at RT overnight. The solvent was evaporated and the residue was co-evaporated with DCM (×3). The residue was triturated in CH$_3$CN and filtered. The oily-solid obtained was dissolved in MeOH and evaporated to give the desired product as HCl salt (6 mg, 77%). HPLC-MS (5-100% B in 8 min at 0.8 mL): $t_R$=3.29 min, [M+H]+ m/z 424.1; $^1$H NMR (300 MHz, DMSO) δ 8.93 (s, 3H), 7.77 (s, 1H), 7.55 (m, 2H), 7.29 (d, J=8.9 Hz, 1H), 4.76 (m, 1H), 3.92 (s, 3H), 3.23 (m, 2H), 3.09 (m, 2H), 2.11 (m, 2H), 1.90 (m, 2H).

Intermediate M 2-(3,4-Dimethoxy-phenyl)-imidazo[2,1-b][1,3,4]thiadiazole

A solution of 2-bromo-imidazo[2,1-b][1,3,4]thiadiazole (0.5 g, 2.5 mmol, 1 eq), 3,4-dimethoxyphenylboronic acid (0.683 g, 3.7 mmol, 1.5 eq), dioxane (12.5 mL) and Na$_2$CO$_3$ (2M aq. solution, 3.8 mL) was degassed for 20 minutes at room temperature. Pd(Ph$_3$P)$_2$Cl$_2$ was added and the reaction heated at 110° C. for 2 h in an argon atmosphere. The reaction mixture was diluted with EtOAc and washed with water. The combined organic layers were dried (Na$_2$SO$_4$), filtered and concentrated, and the residue was purified by column chromatography (SiO$_2$, cyclohexane/20-100% ethylacetate). The product was further purified by triturating with Et$_2$O, filtered off and dried affording the desired product (0.080 g). $^1$H NMR (300 MHz, DMSO) δ/ppm 8.18 (d, J=1.4, 1H), 7.47 (m, 2H), 7.33 (d, J=1.4, 1H), 7.15 (d, J=8.3, 1H), 3.86 (s, 3H), 3.75 (s, 3H). The filtrate was concentrated, redissolved in DCM and purified by flash-chromatography (SiO$_2$, DCM/1% MeOH) to afford the desired product (0.65 g, containing some Ph$_3$PO) that was used as such in the next step.

Intermediate N 2-(3,4-Dimethoxy-phenyl)-5-iodo-imidazo[2,1-b][1,3,4]thiadiazole 2-(3,4-Dimethoxy-phenyl)-imidazo[2,1-b][1,3,4]thiadiazole (from the previous step, 0.65 g, 2.50 mmol, 1 eq) was dissolved in DMF (9 mL), and NIS (0.41 g, 1.75 mmol, 0.7 eq) was added. The mixture was stirred at RT in an argon atmosphere. After 2 hours HPLC-MS analysis indicated incomplete conversion; 0.1 g of NIS was added, and the reaction mixture was stirred at RT overnight. Another 0.08 g of NIS was added, and after another 2 h of stirring at RT the reaction mixture was poured into 20 mL of aq. sodium thiosulfate (10%) and extracted with EtOAc. The combined organic layers were washed with water, dried (Na$_2$SO$_4$) and concentrated, and the residue (0.888 g) was purified by column chromatography (SiO$_2$, cyclohexane/20-100% EtOAc) to afford the desired product (white solid, 0.336 g, 36% yield, 2 steps). HPLC-MS: (10-95% B in 4 min, 0.5 mL/min+2 min 100% B, 0.7 mL/min): $t_R$=4.42 min, [M+H]+ m/z 387.9; $^1$H NMR (300 MHz, DMSO) δ/ppm 7.50 (dd, J=2.2, 8.4, 1H), 7.42 (d, J=2.1, 1H), 7.37 (s, 1H), 7.16 (d, J=8.5, 1H), 3.89 (s, 3H), 3.86 (s, 3H).

Example 16

2,5-Bis-(3,4-dimethoxy-phenyl)-imidazo[2,1-b][1,3,4]thiadiazole

A mixture of 2-(3,4-dimethoxy-phenyl)-5-iodo-imidazo[2,1-b][1,3,4]thiadiazole (0.10 g, 0.3 mmol, 1 eq), dioxane (5 mL), 3,4-dimethoxyphenylboronic acid (0.12 g, 0.6 mmol, 2.5 eq), Pd(Ph$_3$P)$_2$Cl$_2$ (0.018 g, 0.1 eq), K$_2$CO$_3$ (0.178 g, 1.3 mmol, 5 eq) and water (2 mL) was heated in the microwave oven (120° C., 30 min). The reaction mixture was concentrated, and the residue was purified by column chromatography (SiO$_2$, cyclohexane/5-100% EtOAc). The obtained product was triturated with MeOH/Et$_2$O to give the desired product (yellow solid, 0.026 g, 26%). HPLC-MS: (5-100% B in 10 min, 0.6 mL/min, 50° C.): $t_R$=7.24 min, [M+H]+ m/z 398.1; $^1$H NMR (300 MHz, DMSO) δ/ppm 7.74 (s, 1H), 7.70 (d, J=2.0, 1H), 7.61 (dd, J=2.0, 8.4, 1H), 7.57-7.50 (m, 2H), 7.17 (d, J=8.2, 1H), 7.09 (d, J=8.5, 1H), 3.88 (s, 6H), 3.86 (s, 3H), 3.81 (s, 3H).

Example 17

5-[2-(3,4-Dimethoxy-phenyl)-imidazo[2,1-b][1,3,4]thiadiazol-5-yl]-pyridine-2-carbonitrile A mixture of 2-(3,4-dimethoxy-phenyl)-5-iodo-imidazo[2,1-b][1,3,4]thiadiazole (0.10 g, 0.3 mmol, 1 eq), dioxane (5 mL), 2-cyanopyridine-5-boronic acid pinacol ester (0.155 g, 0.64 mmol, 2.5 eq), Pd(Ph$_3$P)$_2$Cl$_2$ (0.018 g, 0.1 eq), potassium carbonate (0.178 g, 1.3 mmol, 5 eq), and water (2 mL) was heated in the microwave oven (120° C., 30 min) and was left to cool to RT. A precipitate formed that was filtered off (0.048 g) and washed with a mixture of Et$_2$O and little MeOH to afford the desired product (white solid, 0.029 g, 31%). HPLC-MS: (5-100% B in 8 min, 0.8 mL/min, 50° C.): $t_R$=5.37 min, [M+H]+ m/z 364.1; $^1$H NMR (300 MHz, DMSO) d 9.47-9.39 (m, 1H), 8.68 (dd, J=8.3, 2.3, 1H), 8.23-8.10 (m, 2H), 7.60 (dd, J=8.3, 2.3, 1H), 7.51 (d, J=2.1, 1H), 7.17 (d, J=8.5, 1H), 3.91 (s, 3H), 3.87 (s, 3H);

Example 18

2-Amino-5-[2-(3,4-dimethoxy-phenyl)-imidazo[2,1-b][1,3,4]thiadiazol-5-yl]-nicotinonitrile A mixture of 2-(3,4-dimethoxy-phenyl)-5-iodo-imidazo[2,1-b][1,3,4]thiadiazole (0.1 g, 0.258 mmol, 1 eq), 2-amino-5-(4,4,5,5-tetramethyl-[1,3,2]dioxaborolan-2-yl)-nicotinonitrile (0.11 g, 0.449 mmol, 1.74 eq), PdCl$_2$(Ph$_3$P)$_2$ (36 mg, 0.052 mmol, 0.2 eq) and Na$_2$CO$_3$ (2 M aqueous solution, 0.5 mL) in dioxane was heated at 110° C. for 2.5 h. The reaction was cooled down to it and solvents were removed under reduced pressure. The residue was treated with water, sonicated and then filtered. The solid was washed with water, Et$_2$O, Et$_2$O/MeOH (9:1), and dried. The residue was purified on silica gel (isolute flash Si II, DCM/MeOH 5 to 10% MeOH and biotage, MeOH/DCM, 0% to 10%) to give the desired product (21 mg, 22%). HPLC-MS: (5-100% B in 8 min, 0.8 mL/min, 50° C.): t$_R$=4.68 min, [M+H]+ m/z 379.1; $^1$H NMR (300 MHz, DMSO) δ 8.91 (d, J=2.4 Hz, 1H), 8.45 (d, J=2.4 Hz, 1H), 7.72 (s, 2H), 7.56 (dd, J=8.4, 2.1 Hz, 1H), 7.48 (d, J=2.1 Hz, 1H), 7.17 (m, 3H), 3.89 (s, 3H), 3.86 (s, 3H).

Example 19

4-{5-[2-(3,4-Dimethoxy-phenyl)-imidazo[2,1-b][1,3,4]thiadiazol-5-yl]-pyrimidin-2-yl}-piperazine-1-carboxylic acid tert-butyl ester A mixture of 2-(3,4-dimethoxy-phenyl)-5-iodo-imidazo[2,1-b][1,3,4]thiadiazole (0.3 g, 0.775 mmol, 1 eq), PdCl$_2$(Ph$_3$P)$_2$ (0.11 g, 0.155 mmol, 0.2 eq), 2-(4-boc-piperazin-1-yl)pyrimidine-5-boronic acid pinacol ester (0.454 g, 1.16 mmol, 1.5 eq) and Na$_2$CO$_3$ (2M aqueous solution, 1.5 mL) in dioxane (4.5 mL) was heated at 110° C. for 2.5 h. The reaction was cooled down to it and solvents were removed under reduced pressure. The residue was treated with water, sonicated and filtered. The solid was washed with water, Et$_2$O and dried to give the desired product (416 mg, 100%). HPLC-MS: (5-100% B in 8 min, 0.8 mL/min, 50° C.): t$_R$=6.48 min, [M+H]+ m/z 524.2; $^1$H NMR (300 MHz, DMSO) δ 8.99 (s, 2H), 7.70 (s, 1H), 7.55 (d, J=8.4 Hz, 1H), 7.47 (s, 1H), 7.15 (d, J=8.4 Hz, 1H), 3.88 (s, 3H), 3.86 (s, 3H), 3.80 (m, 4H), 3.43 (m, 4H), 1.43 (s, 9H).

Example 20

2-(3,4-Dimethoxy-phenyl)-5-(2-piperazin-1-yl-pyrimidin-5-yl)-imidazo[2,1-b][1,3,4]thiadiazole To a suspension of 4-{5-[2-(3,4-Dimethoxy-phenyl)-imidazo[2,1-b][1,3,4]thiadiazol-5-yl]-pyrimidin-2-yl}-piperazine-1-carboxylic acid tert-butyl ester (0.105 g, 0.201 mmol, 1 eq) in dioxane (1.5 mL) was added 4M HCl in dioxane (0.5 mL, 0.2 mmol, 10 eq) at 0° C. The reaction was allowed to warm to it and it was stirred overnight. After 18 h additional HCl (0.5 mL) was added and the reaction was stirred for 7 h. Solvents were removed under reduced pressure and the residue was treated with CH$_3$CN. Solids were filtered off and washed with CH$_3$CN to give the desired product as HCl salt (72 mg, 77%). HPLC-MS: (5-40% B in 8 min, 0.8 mL/min, 50° C.): t$_R$=4.68 min, [M+H]+ m/z 424.2; $^1$H NMR (300 MHz, DMSO) δ 8.97 (s, 2H), 7.69 (s, 1H), 7.56 (d, J=8.3 Hz, 1H), 7.49 (s, 1H), 7.16 (d, J=8.5 Hz, 1H), 3.89 (s, 3H), 3.86 (s, 3H), 3.75 (m, 4H), 2.79 (m, 4H).

Example 21

2-(3,4-Dimethoxy-phenyl)-5-[2-(4-methyl-piperazin-1-yl)-pyrimidin-5-yl]-imidazo[2,1-b][1,3,4]thiadiazole To a mixture of 2-(3,4-Dimethoxy-phenyl)-5-(2-piperazin-1-yl-pyrimidin-5-yl)-imidazo[2,1-b][1,3,4]thiadiazole (52 mg, 0.113 mmol, 1 eq), Et$_3$N (0.032 mL, 0.226 mmol, 2 eq), formaldehyde (0.102 mL, 1.36 mmol, 12 eq) and acetic acid (0.02 mL, 0.136 mmol, 1.2 eq) in MeOH (2 mL) was added Sodium cyanoborohydride (0.1 g, 1.58 mmol, 14 eq). The reaction mixture was stirred at rt for 2 h. Solvents were evaporated to dryness and the residue was dissolved in sat NaHCO$_3$/EtOAc. Layers were separated and the aqueous layer was extracted once with EtOAc. The combined organic layers were dried, filtered and evaporated. The residue was purified by HPLC to give the desired product (6 mg, 12%). HPLC-MS: (5-40% B in 8 min, 0.8 mL/min, 50° C.): t$_R$=4.64 min, [M+H]+ m/z 438.2; $^1$H NMR (300 MHz, DMSO) δ 8.98 (s, 2H), 7.70 (s, 1H), 7.56 (dd, J=8.4, 2.0 Hz, 1H), 7.49 (d, J=2.0 Hz, 1H), 7.16 (d, J=8.5 Hz, 1H), 3.90 (s, 3H), 3.86 (s, 3H), 3.80 (m, 4H), 2.38 (m, 4H), 2.22 (s, 3H).

Intermediate O

4-{5-[2-(3,4-Dimethoxy-phenyl)-imidazo[2,1-b][1,3,4]thiadiazol-5-yl]-3-trifluoromethyl-pyridin-2-yl}-piperazine-1-carboxylic acid tert-butyl ester A mixture of 2-(3,4-dimethoxy-phenyl)-5-iodo-imidazo[2,1-b][1,3,4]thiadiazole (0.2 g, 0.517 mmol, 1 eq), PdCl$_2$(Ph$_3$P)$_2$ (73 mg, 0.103 mmol, 0.2 eq), 4-[5-(4,4,5,5-tetramethyl-[1,3,2]dioxaborolan-2-yl)-3-trifluoromethyl-pyridin-2-yl]-piperazine-1-carboxylic acid tert-butyl ester (0.354 g, 0.775 mmol, 1.5 eq) and Na$_2$CO$_3$ (2M aqueous solution, 1 mL) in dioxane (4 mL) was heated at 110° C. for 2.5 h. The reaction was cooled down to rt and solvents were removed under reduced pressure. The residue was treated with water, sonicated and filtered. The solid was washed with water and purified by column chromatography (Biotage, cHex/EtOac 10 to 100%) to afford the desired product (170 mg, 56%): HPLC-MS: (5-100% B in 8 min, 0.8 mL/min, 50° C.): t$_R$=7.36 min, [M+H]+ m/z 591.2; $^1$H NMR (300 MHz, CDCl$_3$) δ 8.98 (d, J=2.0 Hz, 1H), 8.56 (d, J=2.2 Hz, 1H), 7.62 (s, 1H), 7.42 (m, 2H), 6.95 (m, 1H), 3.98 (s, 3H), 3.96 (s, 3H), 3.57 (m, 4H), 3.31 (m, 4H), 1.50 (s, 9H).

Example 22

2-(3,4-Dimethoxy-phenyl)-5-(6-piperazin-1-yl-5-trifluoromethyl-pyridin-3-yl)-imidazo[2,1-b][1,3,4]thiadiazole To a solution of 4-{5-[2-(3,4-Dimethoxy-phenyl)-imidazo[2,1-b][1,3,4]thiadiazol-5-yl]-3-trifluoromethyl-pyridin-2-yl}-piperazine-1-carboxylic acid tert-butyl ester (0.15 g, 0.254 mmol, 1 eq) in dioxane (4 mL) was added an excess of 4M HCl in dioxane (20 eq) at 0° C. The reaction was allowed to warm to rt and it was stirred for 6.5 h. Solvents were removed under reduced pressure to afford the desired product as HCl salt (146 mg, 100%). HPLC-MS: (5-40% B in 8 min, 0.8 mL/min, 50° C.): t$_R$=5.65 min and 5.96 min, [M+H]+ m/z 491.2; $^1$H NMR (300 MHz, DMSO) δ 9.24 (d, J=1.9 Hz, 1H), 8.77 (d, J=2.1 Hz, 1H), 8.03 (s, 1H), 7.56 (dd, J=8.4, 1.9 Hz, 1H), 7.50 (d, J=1.9 Hz, 1H), 7.19 (d, J=8.5 Hz, 1H), 3.88 (s, 3H), 3.85 (s, 3H), 3.45 (m, 4H), 3.24 (m, 4H).

Example 23

2-(3,4-Dimethoxy-phenyl)-5-[6-(4-methyl-piperazin-1-yl)-5-trifluoromethyl-pyridin-3-yl]-imidazo[2,1-b][1,3,4]thiadiazole To a mixture of 2-(3,4-Dimethoxy-phenyl)-5-(6-piperazin-1-yl-5-trifluoromethyl-pyridin-3-yl)-imidazo[2,1-b][1, 3,4]thiadiazole (105 mg, 0.199 mmol, 1 eq), Et$_3$N (0.056 mL, 0.399 mmol, 2 eq), formaldehyde (0.180 mL, 2.39 mmol, 12 eq) and acetic acid (0.02 mL, 0.239 mmol, 1.2 eq) in MeOH (4 mL) was added Sodium cyanoborohydride (0.175 g, 2.79 mmol, 14 eq). The reaction mixture was stirred at rt for 2 h. Solvents were evaporated to dryness and the residue was dissolved in sat NaHCO$_3$/EtOAc. Layers were separated and the aqueous layer was extracted once with EtOAc. The combined organic layers were dried, filtered and evaporated. The residue was purified on silica gel (isolute flash Si II, 10 g, 96:4 DCM/7N NH$_3$ in MeOH) to give the desired product (50 mg, 50%). HPLC-MS: (5-100% B in 8 min, 0.8 mL/min, 50° C.): $t_R$=3.47 min, [M+H]+ m/z 505.3; $^1$H NMR (300 MHz, CDCl$_3$) δ 8.92 (s, 1H), 8.49 (d, J=1.9 Hz, 1H), 7.52 (s, 1H), 7.42 (d, J=1.7 Hz, 1H), 7.36 (dd, J=8.3, 2.0 Hz, 1H), 6.90 (d, J=8.4 Hz, 1H), 3.94 (s, 3H), 3.88 (s, 3H), 3.41 (m, 4H), 2.57 (m, 4H), 2.34 (s, 3H).

Example 24

2-(3,4-Dimethoxy-phenyl)-5-(2-methylsulfanyl-pyrimidin-5-yl)-imidazo[2,1-b][1,3,4]thiadiazole A mixture of 2-(3,4-dimethoxy-phenyl)-5-iodo-imidazo [2,1-b][1,3,4]thiadiazole (0.25 g, 0.646 mmol, 1 eq), 2-(methylthio)pyrimidine-5-boronic acid pinacol ester (0.244 g, 0.968 mmol, 1.5 eq) and K$_2$CO$_3$ (0.357 g, 2.584 mmol, 4 eq) in 1,2-DME/H$_2$O (9/1, 5 mL) was stirred at RT for 10 min. Then, PdCl$_2$(dppf) (0.053 g, 0.0646 mmol, 0.1 eq) was added and the reaction mixture was heated at 85° C. for 4 h. Solvents were evaporated and water was added to the residue. The suspension was extracted with EtOAc (×3) and the combined organics were dried, filtered and evaporated. The residue was purified in an Isolute Si II cartridge using MeOH in DCM (0% to 1%) to give the desired product (47 mg). The aqueous phase was evaporated to dryness and the residue was redissolved in DCM and filtered. The filtrate was evaporated and purified as described before to give additional desired product (136 mg). Total amount obtained: 183 mg. Overall yield: 73%. HPLC-MS: (5-100% B in 8 min, 0.8 mL/min, 50° C.): $t_R$=5.46 min, [M+H]+ m/z 386.2; $^1$H NMR (300 MHz, CDCl$_3$) δ 9.15 (d, J=5.8 Hz, 2H), 7.64 (s, 1H), 7.45 (m, 2H), 6.97 (m, 1H), 3.99 (s, 3H), 3.98 (s, 3H), 2.64 (s, 3H).

Example 25

2-(3,4-Dimethoxy-phenyl)-5-(2-mthanesulfinyl-pyrimidin-5-yl)-imidazo[2,1-b][1,3,4]thiadiazole MCPBA (0.043 g, 0.249 mmol, 1.2 eq) was added to a solution of 2-(3,4-dimethoxy-phenyl)-5-(2-methylsulfanyl-pyrimidin-5-yl)-imidazo[2,1-b][1,3,4]thiadiazole (0.08 g, 0.207 mmol, 1 eq) in anhydrous DCM (min. volume) at 0° C. under Ar. The reaction mixture was allowed to reach RT and was stirred for 2 h. More DCM was added, and the organic phase was washed with 2N aq. Na$_2$CO$_3$ (2×), dried (MgSO$_4$), filtered, concentrated and dried affording the desired product as a pale yellow solid (72 mg, 87%). HPLC-MS: (5-100% B in 8 min, 0.8 mL/min, 50° C.): $t_R$=3.98 min, [M+H]+ m/z 402.1; $^1$H NMR (300 MHz, CDCl$_3$) δ 9.48 (s, 2H), 7.80 (s, 1H), 7.46-7.39 (m, 2H), 6.96 (d, J=8.1 Hz, 1H), 3.97 (d, J=9.9 Hz, 7H), 2.99 (s, 3H) ppm.

Example 26

N'-{5-[2-(3,4-Dimethoxy-phenyl)-imidazo[2,1-b][1, 3,4]thiadiazol-5-yl]-pyrimidin-2-yl}-N,N-dimethyl-ethane-1,2-diamine 2-(3,4-Dimethoxy-phenyl)-5-(2-methanesulfinyl-pyrimidin-5-yl)-imidazo[2,1-b][1,3,4]thiadiazole (66 mg, 0.164 mmol, 1 eq) was dissolved in 1,4-dioxane (min. volume) at 75° C. N,N-dimethylethylenediamine (0.053 ml, 0.493 mmol, 3 eq) was added, and the solution was heated at 85° C. for 4 h. The solvent was removed, and the residue was triturated in Et$_2$O, filtered and washed with more solvent to give the desired product as a pale yellow solid (46 mg, 66%). HPLC-MS: (5-100% B in 8 min, 0.8 mL/min, 50° C.): $t_R$=2.87 min, [M+H]+ m/z 426.3; $^1$H NMR (300 MHz, CDCl$_3$) δ 8.84 (s, 2H), 7.43-7.38 (m, 3H), 6.93 (d, J=9.0 Hz, 1H), 5.86 (s, 1H), 3.95 (d, J=9.0 Hz, 7H), 3.52 (dd, J=11.4, 5.7 Hz, 2H), 2.56 (t, J=6.0 Hz, 2H), 2.28 (s, 7H) ppm.

Example 27

2-(3,4-dimethoxyphenyl)-5-(5-methoxypyridin-3-yl) imidazo[2,1-b][1,3,4]thiadiazole 2-bromo-5-iodoimidazo[2,1-b][1,3,4]thiadiazole (0.20 g, 0.606 mmol, 1 eq) was dissolved in dioxane (4 mL), and 3,4-dimethoxyphenylboronic acid was added (0.121 g, 0.667 mmol, 1.1 eq) followed by a saturated solution of K$_2$CO$_3$ (1 mL). The suspension was degassed (N$_2$, 10 min), and Pd(dppf)Cl$_2$.DCM (0.085 g, 0.121 mmol, 0.2 eq) was added. The mixture was heated in a nitrogen atmosphere at 110° C. for 2 h, when complete conversion was observed by LC-MS. 3-methoxypyridine-5-boronic acid pinacol ester was added (0.284 g, 1.21 mmol, 2 eq) followed by Pd(dppf)Cl$_2$.DCM (0.085 g, 0.121 mmol, 0.2 eq) and a saturated solution of K$_2$CO$_3$ (1 mL). The mixture was stirred in a microwave oven (120° C., 30 min), cooled to RT and concentrated. The residue was taken up in AcOEt and n-BuOH and washed with water. The organic phase was separated, dried (Na$_2$SO$_4$), filtered and concentrated, and the crude was purified by flash chromatography (SiO$_2$, DCM/EtOAc) and, subsequently, by preparative HPLC (RP-C18, ACN/water) to give the desired product. HPLC-MS (10-95% B in 4 min at 0.5 mL+2 min 100% B, flow 0.8 mL/min, 50° C.): $t_R$=4.09 min, [M+H]+ m/z 369.1; $^1$H-NMR (DMSO-d$_6$): δ=8.82 (1H, d, J=1.5 Hz), 8.21 (1H, d, J=2.7 Hz), 7.99 (1H, dd, J=2.7, 1.5 Hz), 7.94 (1H, s), 7.52 (1H, dd, J=8.4, 2.1 Hz), 7.46 (1H, d, J=2.1 Hz), 7.12 (1H, d, J=8.4 Hz), 3.88 (3H, s), 3.83 (3H, s), 3.81 (3H, s) ppm.

Example 28

5-[2-(3-Methoxy-phenyl)-imidazo[2,1-b][1,3,4]thiadiazol-5-yl]-3-trifluoromethyl-pyridin-2-ylamine To a reaction mixture of 2-bromo-5-iodoimidazo[2,1-b][1, 3,4]thiadiazole (0.150 g, 0.455 mmol), 3-methoxyphenylboronic acid (0.477 mmol) and PdCl$_2$(Ph$_3$P)$_2$ (0.064 g) in dioxane (3 ml), a sat. aq. solution of K$_2$CO$_3$ (1 mL) was added. The mixture was heated at 110° C. for 24 h in a sealed tube. The solvent was evaporated, the residue precipitated with water, and after drying the resulting gum was washed with Et$_2$O. The residue was suspended in dioxane (3 mL), and 5-(4,4,5,5-tetramethyl-[1,3,2]dioxaborolan-2-yl)-3-trifluoromethyl-pyridin-2-ylamine (1.2 eq), PdCl$_2$(Ph$_3$P)$_2$ (0.2 eq) and a sat. solution of K$_2$CO$_3$ (1 mL) were added and heated at 100° C. for 16 h. The solvent was evaporated to dryness, and the residue was purified by automated chromatography in DCM/ MeOH, 100:0 to 95:5) and then by preparative HPLC affording 5 mg of a light-yellow solid that was washed with MeOH and Et$_2$O to obtain 2 mg of the desired product. HPLC-MS: (5-100% B in 8 min, 0.8 mL/min, 50° C.): $t_R$=5.63 min, [M+H]+ m/z 392.1; $^1$H NMR (300 MHz, DMSO-d$_6$) δ 8.86

(s, 1H), 8.41 (s, 1H), 7.80 (s, 1H), 7.53 (t, J=11.5 Hz, 3H), 7.24 (s, 1H), 6.74 (s, 2H), 3.88 (s, 3H), 3.85 (s, 1H).

Example 29

3-[5-(6-Amino-5-trifluoromethyl-pyridin-3-yl)-imidazo[2,1-b][1,3,4]thiadiazol-2-yl]-benzonitrile To a mixture of 2-bromo-5-iodoimidazo[2,1-b][1,3,4]thiadiazole (0.150 g, 0.455 mmol), 3-cyanophenylboronic acid (0.477 mmol) and PdCl$_2$(Ph$_3$P)$_2$ (0.064 g) in dioxane (3 mL), an aq. solution of Na$_2$CO$_3$(2 M, 0.9 mL) was added. The reaction mixture was heated at 110° C. for 24 h in a sealed tube. The solvent was evaporated, the residue precipitated with water, and after drying the resulting gum was washed with Et$_2$O. The residue was suspended in dioxane (3 mL), and 5-(4,4,5,5-tetramethyl-[1,3,2]dioxaborolan-2-yl)-3-trifluoromethyl-pyridin-2-ylamine (1.05 eq), PdCl$_2$(Ph$_3$P)$_2$ (0.2 eq) and a sat. aq. solution of K$_2$CO$_3$ (0.9 mL) were added. The reaction mixture was heated at 100° C. for 16 h and then concentrated to dryness. The residue was washed with water, followed by ethyl ether. The resulting solid was washed with DCM followed by MeOH. The DCM filtrate was evaporated and purified by HPLC to yield the desired product (0.10 g). HPLC-MS: (5-100% B in 8 min, 0.8 mL/min, 50° C.): t$_R$=5.15 min, [M+H]+ m/z 387.1; $^1$H NMR (300 MHz, DMSO-d$_6$) δ 8.90 (s, 1H), 8.49 (s, 1H), 8.38-8.25 (m, 2H), 8.12 (d, J=7.9 Hz, 1H), 7.92-7.74 (m, 2H), 6.75 (s, 2H) ppm.

Example 30

5-[2-(4-Methoxy-phenyl)-imidazo[2,1-b][1,3,4]thiadiazol-5-yl]-3-trifluoromethyl-pyridin-2-ylamine To a mixture of 2-bromo-5-iodoimidazo[2,1-b][1,3,4]thiadiazole (0.150 g, 0.455 mmol), 3-cyanophenylboronic acid (0.477 mmol) and PdCl$_2$(Ph$_3$P)$_2$ (0.064 g) in dioxane (3 mL), an aq. solution of Na$_2$CO$_3$(2 M, 0.9 mL) was added. The reaction mixture was heated at 110° C. for 24 h in a sealed tube. The solvent was evaporated, the residue precipitated with water, and after drying the resulting gum was washed with Et$_2$O. The residue was suspended in dioxane (3 mL), and 5-(4,4,5,5-tetramethyl-[1,3,2]dioxaborolan-2-yl)-3-trifluoromethyl-pyridin-2-ylamine (1.05 eq), PdCl$_2$(Ph$_3$P)$_2$ (0.2 eq) and a sat. solution of K$_2$CO$_3$ (0.9 mL) were added and heated at 100° C. for 16 h. The solvent was evaporated to dryness. The residue was washed with water, followed by ethyl ether. The resulting precipitate was washed with DCM followed by MeOH and purified by preparative HPLC to afford the desired product (0.010 g). HPLC-MS: (5-100% B in 8 min, 0.8 mL/min, 50° C.): t$_R$=5.57 min, [M+H]+ m/z 392.1; $^1$H NMR (300 MHz, DMSO-d$_6$) δ=8.85 (d, J=1.6 Hz, 1H), 8.36 (d, J=1.9 Hz, 1H), 7.91 (d, J=8.8 Hz, 2H), 7.75 (s, 1H), 7.16 (d, J=8.9 Hz, 2H), 6.72 (s, 2H), 3.86 (s, 3H) ppm.

Example 31

N-{3-[5-(6-Amino-5-trifluoromethyl-pyridin-3-yl)-imidazo[2,1-b][1,3,4]thiadiazol-2-yl]-phenyl}-methanesulfonamide A mixture of 2-bromo-5-iodoimidazo[2,1-b][1,3,4]thiadiazole (150 mg, 0.455 mmol, 1 eq), 3-(methylsulfonylamino)phenylboronic acid (127 mg, 0.591 mmol, 1.3 eq), PdCl$_2$(PPh$_3$)$_2$ (64 mg, 0.091 mmol, 0.2 eq) and 2M aq Na$_2$CO$_3$ (1 mL) in dioxane (3 mL) was refluxed for 2 h. Dioxane was evaporated, water added and the mixture was extracted with DCM. The organic layers were dried, filtered and evaporated. The residue (130 mg) was used as such for the second coupling which was done under the same conditions (using 170 mg of 5-(4,4,5,5-tetramethyl-[1,3,2]dioxaborolan-2-yl)-3-trifluoromethyl-pyridin-2-ylamine and 70 mg of PdCl$_2$(PPh$_3$)$_2$). The solvents were removed under reduced pressure, water was added and the solid was filtered and washed with water. Upon standing, a solid appeared in the aqueous filtrate. It was filtered and washed with ether to give the desired product (43 mg, 21%). HPLC-MS (5-100% B in 8 min at 0.8 mL): t$_R$=5.57 min, [M+H]+ m/z 458.1; $^1$H NMR (700 MHz, CDCl$_3$) δ 7.24 (s, 3H), 7.11 (s, 2H), 3.95 (s, 6H), 3.93 (s, 6H), 3.92 (s, 3H), 3.89 (s, 3H).

Example 32

5-(2-Pyridin-3-yl-imidazo[2,1-b][1,3,4]thiadiazol-5-yl)-3-trifluoromethyl-pyridin-2-ylamine A mixture of 2-bromo-5-iodoimidazo[2,1-b][1,3,4]thiadiazole (150 mg, 0.455 mmol, 1 eq), pyridine-3-boronic acid (67 mg, 0.546 mmol, 1.1 eq), PdCl$_2$(PPh$_3$)$_2$ (80 mg, 0.114 mmol, 0.25 eq) and 2M aq Na$_2$CO$_3$ (1 mL) in dioxane (3 mL) was refluxed for 2 h. The solvent was evaporated, water was added and the mixture was extracted with Et$_2$O. The organic layer was -discarded and the aqueous phase was re-extracted with CHCl$_3$/$^i$PrOH 1:1. The organics were dried, filtered and evaporated. The residue was precipitated in ether with some DCM and MeOH and filtered to give the desired intermediate (77 mg, 50%). This intermediate was used for the second coupling which was done under the same conditions (using 110 mg of 5-(4,4,5,5-tetramethyl-[1,3,2]dioxaborolan-2-yl)-3-trifluoromethyl-pyridin-2-ylamine and 70 mg of PdCl$_2$(PPh$_3$)$_2$). The solvent was removed under vacuum, water was added and the mixture was extracted with CHCl$_3$/$^i$PrOH 1:1. The organics were dried, filtered and evaporated. The residue was precipitated in ether with some DCM and MeOH and filtered. The residue was purified by column chromatography (DCM/MeOH, 10:0 to 9:1 to 95:5 with 1% TEA) and by HPLC to afford the desired product (2 mg, 1%). HPLC-MS (5-100% B in 8 min at 0.8 mL): t$_R$=4.28 min, [M+H]+ m/z 363.1; $^1$H NMR (300 MHz, DMSO) δ 9.17 (d, J=1.9 Hz, 1H), 8.88 (d, J=1.8 Hz, 1H), 8.81 (dd, J=4.8, 1.5 Hz, 1H), 8.38 (m, 2H), 7.82 (s, 1H), 7.67 (dd, J=7.9, 5.0 Hz, 1H), 6.76 (s, 2H).

Example 33

4-[5-(6-Amino-5-trifluoromethyl-pyridin-3-yl)-imidazo[2,1-b][1,3,4]thiadiazol-2-yl]-benzonitrile A mixture of 2-bromo-5-iodoimidazo[2,1-b][1,3,4]thiadiazole (150 mg, 0.455 mmol), 4-cianophenylboronic acid (70 mg, 0.477 mmol), PdCl$_2$(Ph$_3$P)$_2$ (64 mg, 0.091 mmol) in dioxane (3 mL) and sat K$_2$CO$_3$ (1 mL) was heated at 110° C. for 24 h. The solvent was evaporated to dryness, water was added and the slurry precipitate was filtered off and washed with Et$_2$O and MeOH to give the desired intermediate (50 mg). This product was suspended in dioxane, then 5-(4,4,5,5-tetramethyl-[1,3,2]dioxaborolan-2-yl)-3-trifluoromethyl-pyridin-2-ylamine (1.2 eq), PdCl$_2$(Ph$_3$P)$_2$ and a sat. K$_2$CO$_3$ (1 mL) were added. The reaction mixture was heated at 100° C. for 16 h. The solvent was evaporated to dryness and the residue was purified by automated chromatography (DCM/MeOH-NH$_3$, 100 to 95:5) to obtain a brown solid which was repurified by HPLC to yield the desired product (5 mg, 3%) as a light yellow solid. HPLC-MS (5-100% B in 8 min at 0.8 mL): t$_R$=5.24 min, [M+H]+ m/z 387.0; $^1$H NMR (300 MHz, DMSO) δ 8.87 (s, 1H), 8.34 (s, 1H), 8.17 (d, J=8.4, 2H), 8.09 (d, J=8.4, 2H), 7.83 (s, 1H), 6.75 (s, 2H).

Intermediate P

N-[3-(5-Iodo-imidazo[2,1-b][1,3,4]thiadiazol-2-yl) -benzyl]-methanesulfonamide

A mixture of 2-bromo-5-iodoimidazo[2,1-b][1,3,4]thiadiazole (0.25 g, 0.757 mmol, 1 eq), (3-methanesulfonylaminomethylphenyl)boronic acid (0.208 g, 0.908 mmol, 1.2 eq), cesium carbonate (0.493 g, 1.514 mmol, 2 eq), Pd(PPh$_3$)$_2$Cl$_2$ (0.053 g, 0.075 mmol, 0.1 eq), 1,4-dioxane (6 mL) and water (6 mL) was heated in a pressure tube at 115° C. for 4 h. Solvents were removed and the slurry obtained was partitioned between water and 10% MeOH in DCM. The organic layer was dried, filtered and evaporated. The residue was purified in an Isolute Flash Si II column (EtOAc) to give the desired product (77 mg, 23%). HPLC-MS (10-95% B in 4 min at 0.5 mL+2 min 100% B, flow 0.8 mL/min, 50° C.): t$_R$=4.04 min, [M+H]+ m/z 435.0.

Example 34

N-{3-[5-(6-Amino-5-trifluoromethyl-pyridin-3-yl)-imidazo[2,1-b][1,3,4]thiadiazol-2-yl]-benzyl}-methanesulfonamide N-[3-(5-Iodo-imidazo[2,1-b][1,3,4]thiadiazol-2-yl) -benzyl]-methanesulfonamide (77 mg, 0.177 mmol, 1 eq) was dissolved in 1,4-dioxane (3 mL) and 5-(4,4,5,5-tetramethyl-[1,3,2]dioxaborolan-2-yl)-3-trifluoromethyl-pyridin-2-ylamine (76 mg, 0.265 mmol, 1.5 eq), K$_2$CO$_3$ (73 mg, 0.531 mmol, 3 eq), H$_2$O (2 mL) and dichlorobis(triphenylphosphine)palladium(II)(12 mg, 0.0177 mmol, 0.1 eq) were added. The reaction mixture was heated in a pressure tube at 105° C. overnight. Solvents were removed and the residue obtained was suspended in water and extracted twice with EtOAc. The organic layers were dried, filtered end evaporated. The residue was triturated with CH$_3$CN and filtered. The solid was purified in an Isolute Si II cartridge (DCM/MeOH, 0%-5%). The product obtained was precipitated in CH$_3$CN and filtered to give the desired product (5 mg, 6%). HPLC-MS (5-100% B in 8 min at 0.8 mL): t$_R$=4.70 min, [M+H]+ m/z 469.1; $^1$H NMR (300 MHz, DMSO) δ 8.88 (s, 1H), 8.35 (s, 1H), 7.95 (s, 1H), 7.90 (m, 1H), 7.80 (s, 1H), 7.73 (t, J=6.3 Hz, 1H), 7.62 (d, J=4.7 Hz, 2H), 6.74 (s, 2H), 4.29 (d, J=6.3 Hz, 2H), 2.93 (s, 3H).

Intermediate Q 3-(5-Iodo-imidazo[2,1-b][1,3,4]thiadiazol-2-yl) -benzamide

A mixture of 2-bromo-5-iodoimidazo[2,1-b][1,3,4]thiadiazole (150 mg, 0.45 mmol), 3-aminocarbonylphenylboronic acid (85 mg, 0.50 mmol), PdCl$_2$(PPh$_3$)$_2$ (32 mg, 0.045 mmol) and Na$_2$CO$_3$ (145 mg, 1.4 mmol) in dioxane (1.5 mL) and water (0.3 mL) was heated at 90° C. for 2 h. The reaction mixture was cooled and diluted with DCM (35 mL) and sat NaHCO$_3$ (20 mL). The organic layer was washed with sat. NaHCO$_3$ (3×20 mL) and brine (30 mL), dried over Na$_2$SO$_4$, filtered and concentrated in vacuo. The residue was triturated with diethylether and filtered to give the desired product (73 mg, 42%). HPLC-MS (10-95% B in 4 min at 0.5 mL+2 min 100% B, flow 0.8 mL/min, 50° C.): t$_R$=3.59 min, [M+H]+ m/z 371.1.

Example 35

3-[5-(6-Amino-5-trifluoromethyl-pyridin-3-yl)-imidazo[2,1-b][1,3,4]thiadiazol-2-yl]-benzamide A mixture of 3-(5-Iodo-imidazo[2,1-b][1,3,4]thiadiazol-2-yl)-benzamide (70 mg, 0.18 mmol), 5-(4,4,5,5-tetramethyl-[1,3,2]dioxaborolan-2-yl)-3-trifluoromethyl-pyridin-2-ylamine (75 mg, 0.24 mmol), PdCl$_2$(PPh$_3$)$_2$ (20 mg) and Na$_2$CO$_3$ (60 mg, 0.567 mmol) in dioxane (2 mL) and water (0.5 mL) was heated at 100° C. in a sealed tube for 2 h. The mixture was diluted with DCM (20 mL), washed with sat aq NaHCO$_3$ (2×20 mL) and brine (30 mL), dried over Na$_2$SO$_4$, filtered and concentrated. The residue was purified by column chromatography and by HPLC to give the desired product (2 mg, 3%). HPLC-MS (5-100% B in 8 min at 0.8 mL): t$_R$=4.26 min, [M+H]+ m/z 405.2; $^1$H NMR (300 MHz, DMSO) δ 8.84 (s, 1H), 8.34 (s, 1H), 8.30 (s, 1H), 8.22 (s, 1H), 8.06 (t, J=8.6 Hz, 2H), 7.75 (s, 1H), 7.66 (t, J=7.8 Hz, 1H), 7.55 (s, 1H), 6.67 (s, 2H).

Intermediate R 2-(1-Ethyl-1H-pyrazol-4-yl)-5-iodo-imidazo[2,1-b] [1,3,4]thiadiazole A mixture of 2-bromo-5-iodoimidazo[2,1-b][1,3,4]thiadiazole (0.18 g, 0.546 mmol, 1 eq), 1-ethyl-1H-pyrazole-4-boronic acid, pinacol ester (0.145 g, 0.655 mmol, 1.2 eq), Pd(PPh$_3$)$_2$Cl$_2$ (0.077 g, 0.109 mmol, 0.2 eq) and 2M aq Na2CO3 (1 mL) in dioxane (3 mL) was refluxed for 2 h. The solvent was evaporated and the residue was treated with water. The suspension was filtered off (avoid taking the heavier reddish solid) and washed with water. The solid (110 mg) was used in the next step of the synthesis with no further treatment. HPLC-MS (10-95% B in 4 min at 0.5 mL+2 min 100% B, flow 0.8 mL/min, 50° C.): t$_R$=3.98 min, [M+H]+ m/z 345.9.

Example 36

5-[2-(1-Ethyl-1H-pyrazol-4-yl)-imidazo[2,1-b][1,3,4]thiadiazol-5-yl]-3-trifluoromethyl-pyridin-2-ylamine A mixture of 2-(1-Ethyl-1H-pyrazol-4-yl)-5-iodo-imidazo [2,1-b][1,3,4]thiadiazole (110 mg, 0.319 mmol, 1 eq), 5-(4, 4,5,5-tetramethyl-[1,3,2]dioxaborolan-2-yl)-3-trifluoromethyl-pyridin-2-ylamine (119 mg, 0.414 mmol, 1.3 eq), Pd(PPh$_3$)$_2$Cl$_2$ (45 mg, 0.064 mmol, 0.2 eq) and 2M aq Na$_2$CO$_3$ (1 mL) in dioxane (3 mL) was refluxed for 2 h. The solvent was evaporated and the residue was treated with water. The suspension was filtered off and washed with Et$_2$O. The solid was purified by column chromatography (DCM/MeOH 9:1) to afford the desired product (16 mg, 13%). HPLC-MS (5-100% B in 8 min at 0.8 mL): t$_R$=4.62 min, [M+H]+ m/z 380.1; $^1$H NMR (300 MHz, DMSO) δ 8.84 (s, 1H), 8.61 (s, 1H), 8.29 (d, J=2.0 Hz, 1H), 8.08 (s, 1H), 7.74 (s, 1H), 6.72 (s, 2H), 4.24 (q, J=7.3 Hz, 2H), 1.43 (t, J=7.3 Hz, 3H).

Intermediate S

5-Iodo-2-(4-methyl-pyridin-3-yl)-imidazo[2,1-b][1, 3,4]thiadiazole

A mixture of 2-bromo-5-iodoimidazo[2,1-b][1,3,4]thiadiazole (50 mg, 0.152 mmol), 4-methylpyridine-3-boronic acid (23 mg, 0.167 mmol), PdCl$_2$(dppf) (25 mg, 0.03 mmol) and sat. aq. K$_2$CO$_3$ (0.25 ml) in dioxane (0.5 mL) was heated at 110° C. overnight. The reaction mixture was cooled, diluted with DCM and washed with water. The organic layer was dried (Na$_2$SO$_4$), filtered and evaporated. The residue was purified by column chromatography (MeOH/DCM, 0% to 40%) to give the desired product (50 mg, 96%). HPLC-MS (10-95% B in 4 min at 0.5 mL+2 min 100% B, flow 0.8 mL/min, 50° C.): t$_R$=3.75 min, [M+H]+ m/z 343.1.

Example 37

5-[2-(4-Methyl-pyridin-3-yl)-imidazo[2,1-b][1,3,4] thiadiazol-5-yl]-3-trifluoromethyl-pyridin-2-ylamine A mixture of 5-Iodo-2-(4-methyl-pyridin-3-yl)-imidazo [2,1-b][1,3,4]thiadiazole (18 mg, 0.053 mmol, 1 eq), 5-(4,4,5,5-tetramethyl-[1,3,2]dioxaborolan-2-yl)-3-trifluoromethyl-pyridin-2-ylamine (20 mg, 0.068 mmol, 1.3 eq), Pd(PPh$_3$)$_2$Cl$_2$ (9 mg, 0.011 mmol, 0.2 eq) and sat aq K$_2$CO$_3$ (0.22 mL) in DME (0.5 mL) was heated under microwave irradiation at 120° C. for 30 min. On cooling, DCM was added and the mixture was washed with water. The organic layer was dried (Na$_2$SO$_4$), filtered and evaporated. The residue was purified by column chromatography (DCM/MeOH 95:5) to afford the desired product (8 mg, 40%). HPLC-MS (5-100% B in 8 min at 0.8 mL): t$_R$=4.32 min, [M+H]+ m/z 377.1; $^1$H NMR (300 MHz, CDCl$_3$) δ 8.80 (s, 1H), 8.70 (s, 1H), 8.55 (d, J=5.0 Hz, 1H), 8.31 (s, 1H), 7.56 (s, 1H), 7.28 (d, J=5.0 Hz, 1H), 5.39 (s, 2H), 2.63 (s, 3H).

Intermediate T

5-Iodo-2-(1'-(tert-butoxycarbonyl)-2-oxo-1,2-dihydrospiro[indole-3,4'-piperidine]-5-yl)-imidazo[2,1-b] [1,3,4]thiadiazole A mixture of 2-bromo-5-iodo-imidazo[2,1-b][1,3,4]thiadiazole (100 mg, 0.303 mmol), 1'-(tert-butoxycarbonyl)-2-oxo-1,2-dihydrospiro[indole-3,4'-piperidine]-5-boric acid (115 mg, 0.333 mmol), PdCl$_2$(dppf) (50 mg, 0.061 mmol) and a saturated K$_2$CO$_3$ solution (0.37 mL) in DME (1 mL) was heated at 90° C. for 20 h. The reaction mixture was diluted with DCM and washed with H$_2$O. The organic layer was dried (Na$_2$SO$_4$), filtered and concentrated. The residue was purified by column chromatography (0% to 10% MeOH in DCM) to give the desired product (46 mg, 28%) as a yellow solid. HPLC-MS (10-95% B in 4 min at 0.5 mL+2 min 100% B, flow 0.8 mL/min, 50° C.): t$_R$=4.72 min, [M+H]+ m/z 552.2. $^1$H NMR (300 MHz, CDCl$_3$) δ 8.67 (s, 1H), 7.81 (s, 1H), 7.75 (d, J=8.0 Hz, 1H), 7.05 (d, J=8.1 Hz, 1H), 3.90 (m, 4H), 1.93 (m, 4H), 1.53 (s, 9H).

Example 38

5-[2-(1'-(tert-butoxycarbonyl)-2-oxo-1,2-dihydrospiro[indole-3,4'-piperidine]-5-yl)-imidazo[2,1-b] [1,3,4]thiadiazol-5-yl]-3-trifluoromethyl-pyridin-2-ylamine A mixture of 5-Iodo-2-(1'-(tert-butoxycarbonyl)-2-oxo-1,2-dihydrospiro[indole-3,4'-piperidine]-5-yl)-imidazo[2,1-b] [1,3,4]thiadiazole (46 mg, 0.082 mmol), 5-(4,4,5,5-tetramethyl-[1,3,2]dioxaborolan-2-yl)-3-trifluoromethyl-pyridin-2-ylamine (31 mg, 0.106 mmol), PdCl$_2$(dppf) (13 mg, 0.016 mmol) and sat Na$_2$CO$_3$ (0.41 mL) in DME (0.82 mL) was heated under microwave irradiation at 120° C. for 30 min. The reaction mixture was diluted with DCM and washed with H$_2$O. The organic layer was dried (Na$_2$SO$_4$), filtered and concentrated. The residue was purified by column chromatography (Isolute/Flash, Sill, 0% to 5% MeOH in DCM) to give the desired product (19.5 mg, 41%) as a yellow solid. HPLC-MS (5-100% B in 8 min at 0.8 mL): t$_R$=5.77 min, [M+H]+ m/z 586.2; $^1$H NMR (300 MHz, DMSO) δ 10.90 (s, 1H), 8.87 (d, J=1.8 Hz, 1H), 8.43 (d, J=2.0 Hz, 1H), 8.01 (d, J=1.6 Hz, 1H), 7.83 (dd, J=8.1, 1.7 Hz, 1H), 7.77 (s, 1H), 7.07 (d, J=8.2 Hz, 1H), 6.72 (s, 2H), 3.71 (s, 4H), 1.77 (m, 4H), 1.46 (s, 9H).

Example 39

5-[2-(2-oxo-1,2-dihydrospiro[indole-3,4'-piperidine]-5-yl)-imidazo[2,1-b][1,3,4]thiadiazol-5-yl]-3-trifluoromethyl-pyridin-2-ylamine A mixture of 5-[2-(1'-(tert-butoxycarbonyl)-2-oxo-1,2-dihydrospiro[indole-3,4'-piperidine]-5-yl)-imidazo[2,1-b][1,3,4]thiadiazol-5-yl]-3-trifluoromethyl-pyridin-2-ylamine (6.4 mg, 0.011 mmol) and HCl (4N in dioxane, 0.03 mL, 0.11 mmol) in MeOH (0.2 mL) was stirred at room temperature for 16 h. The solvent was evaporated under vacuum and the residue was triturated from Et$_2$O to give the desired product as HCl salt (5 mg, 86%). HPLC-MS (5-100% B in 8 min at 0.8 mL): t$_R$=3.01 min, [M+H]+ m/z 486.1; $^1$H NMR (300 MHz, D$_2$O) δ 8.19 (m, 1H), 8.04 (m, 1H), 7.31 (m, 3H), 6.56 (m, 1H), 3.49 (m, 2H), 3.21 (m, 2H), 3.10 (m, 2H), 1.92 (m, 2H), 1.72 (m, 2H).

Intermediate U 5-(5-Iodo-imidazo[2,1-b][1,3,4]thiadiazol-2-yl)-1H-indole

A mixture of 2-bromo-5-iodoimidazo[2,1-b][1,3,4]thiadiazole (0.150 g, 0.455 mmol, 1 eq) and 5-indolylboronic acid (0.088 g, 0.546 mmol, 1.2 eq), 2M aq Na$_2$CO$_3$ (1 mL) and PdCl$_2$(PPh$_3$)$_2$ (0.064 g, 0.091 mmol, 0.2 eq) in dioxane (5 mL) was heated at 110° C. for 2 h. The solvent was removed in vacuo, redissolved in DCM/water (150 mL) and extracted with DCM (2×80 mL). The combined organic layers were dried (MgSO$_4$), filtered and evaporated. The residue was purified by column chromatography (20-70% EtOAc in cyclohexane) to afford the desired product (91 mg, 54%) as a yellow solid. HPLC-MS (10-95% B in 4 min at 0.5 mL+2 min 100% B, flow 0.8 mL/min, 50° C.): t$_R$=4.53 min, [M+H]+ m/z 367.0.

Example 40

5-[2-(1H-Indol-5-yl)-imidazo[2,1-b][1,3,4]thiadiazol-5-yl]-3-trifluoromethyl-pyridin-2-ylamine A mixture of 5-(5-Iodo-imidazo[2,1-b][1,3,4]thiadiazol-2-yl)-1H-indole (0.091 g, 0.247 mmol, 1 eq), 5-(4,4,5,5-tetramethyl[-1,3,2]dioxaborolan-2-yl)-3-trifluoromethyl-pyridin-2-ylamine (0.107 g, 0.371 mmol, 1.5 eq), 2M aq Na$_2$CO$_3$ (1 mL) and PdCl$_2$(PPh$_3$)$_2$ (0.035 g, 0.049 mmol, 0.2 eq) in dioxane (5 mL) was heated at 110° C. for 24 h. The solvent was removed in vacuo, redissolved in DCM/water (150 mL) and extacted with DCM (2×80 mL). The organic layer was dried (MgSO$_4$), filtered and evaporated. The residue was purified by column chromatography (0-10% MeOH in DCM and a second column 0-5% MeOH in DCM) to afford the desired product (12 mg, 12%) as a yellow solid. HPLC-MS (5-100% B in 8 min at 0.8 mL): $t_R$=5.08 min, [M+H]+ m/z 401.0; $^1$H NMR (300 MHz, DMSO) δ 11.57 (s, 1H), 8.90 (d, J=1.8 Hz, 1H), 8.39 (d, J=2.1 Hz, 1H), 8.20 (d, J=1.6 Hz, 1H), 7.75 (s, 1H), 7.73 (dd, J=9.2, 2.4 Hz, 1H), 7.61 (d, J=8.6 Hz, 1H), 7.52 (m, 1H), 6.73 (s, 2H), 6.64 (s, 1H).

Intermediate V

5-Iodo-2-(3-methanesulfonyl-phenyl)-imidazo[2,1-b][1,3,4]thiadiazole

A mixture of 2-bromo-5-iodoimidazo[2,1-b][1,3,4]thiadiazole (0.20 g, 0.606 mmol, 1 eq), 3-(methylsulfonyl)phenylboronic acid (0.182 g, 0.909 mmol, 1.5 eq), PdCl$_2$(PPh$_3$)$_2$ (0.085 g, 0.121 mmol, 0.2 eq) and 2M Na$_2$CO$_3$ (1.0 mL) in dioxane (5 mL) was heated at 110° C. for 24 h. More PdCl$_2$(PPh$_3$)$_2$ (0.1 eq) was added and the reaction mixture was heated at 110° C. for 4 h. The solvent was removed, water was added and the mixture was extracted with DCM. The organic layer was dried (MgSO$_4$), filtered and evaporated. The residue was triturated from MeOH and filtered to give the desired product (91 mg, 37%) as an orange solid. It was used in the next step of the synthesis with no further treatment. HPLC-MS (10-95% B in 4 min at 0.5 mL+2 min 100% B, flow 0.8 mL/min, 50° C.): $t_R$=3.98 min, [M+H]+ m/z 405.9.

Example 41

5-[2-(3-Methanesulfonyl-phenyl)-imidazo[2,1-b][1,3,4]thiadiazol-5-yl]-3-trifluoromethyl-pyridin-2-ylamine A mixture of 5-Iodo-2-(3-methanesulfonyl-phenyl)-imidazo[2,1-b][1,3,4]thiadiazole (0.091 g, 0.225 mmol, 1 eq), and 5-(4,4,5,5-tetramethyl-[1,3,2]dioxaborolan-2-yl)-3-trifluoromethyl-pyridin-2-ylamine (0.097 g, 0.337 mmol, 1.5 eq), PdCl$_2$(PPh$_3$)$_2$ (32 mg, 0.045 mmol, 0.2 eq) and 2M Na$_2$CO$_3$ (1 mL) and dioxane (5 mL). The reaction mixture was heated at 110° C. for 24 h. The solvent was evaporated, the residue was redissolved in DCM/water (150 mL) and extacted with DCM (2×80 mL). The organic layer was dried (MgSO$_4$), filtered and evaporated. The residue was triturated from MeOH and filtered off. The solid was purified by column chromatography (0-5% MeOH in DCM) to give the desired product (20 mg, 20%) as a yellow solid. HPLC-MS (5-100% B in 8 min at 0.8 mL): $t_R$=5.25 min, [M+H]+ m/z 440.0; $^1$H NMR (300 MHz, DMSO) δ 8.90 (d, J=1.8 Hz, 1H), 8.44 (d, J=1.6 Hz, 1H), 8.37 (d, J=2.0 Hz, 1H), 8.33 (d, J=7.9 Hz, 1H), 8.19 (d, J=8.1 Hz, 1H), 7.92 (t, J=7.9 Hz, 1H), 7.84 (s, 1H), 6.74 (s, 2H), 3.32 (s, 3H).

Intermediate W

[3-(5-Iodo-imidazo[2,1-b][1,3,4]thiadiazol-2-yl)-phenyl]-dimethyl-amine

A mixture of 2-bromo-5-iodoimidazo[2,1-b][1,3,4]thiadiazole (0.150 g, 0.455 mmol, 1 eq), 3-(N,N-dimethylamino)phenylboronic acid (0.113 g, 0.682 mmol, 1.5 eq), Cs$_2$CO$_3$ (0.296 g, 0.909 mmol, 2 eq) and Pd(PPh$_3$)$_4$ (0.032 g, 0.027 mmol, 0.06 eq) were dissolved in Dioxane (8 mL) and water (2 mL). The reaction mixture was heated at 95° C. for 24 h. Additional amounts of 3-(N,N-dimethylamino)phenylboronic acid (1.5 eq) and Pd(PPh$_3$)$_4$ (0.06 eq) were added and the reaction mixture was heated at 95° C. for 3 days. The solvent was removed in vacuo, redissolved in DCM/water (150 mL) and extracted with DCM (2×80 mL). The combined organic layers were dried (MgSO$_4$), filtered and evaporated. The residue was purified by column chromatography (20-70% EtOAc in cyclohexane) to afford the desired product (36 mg, 21%) as a yellow solid. HPLC-MS (10-95% B in 4 min at 0.5 mL+2 min 100% B, flow 0.8 mL/min, 50° C.): $t_R$=4.73 min, [M+H]+ m/z 371.1.

Example 42

5-[2-(3-Dimethylamino-phenyl)-imidazo[2,1-b][1,3,4]thiadiazol-5-yl]-3-trifluoromethyl-pyridin-2-ylamine A mixture of [3-(5-Iodo-imidazo[2,1-b][1,3,4]thiadiazol-2-yl)-phenyl]-dimethyl-amine (0.084 g, 0.226 mmol, 1 eq), 5-(4,4,5,5-tetramethyl-[1,3,2]dioxaborolan-2-yl)-3-trifluoromethyl-pyridin-2-ylamine (0.098 g, 0.339 mmol, 1.5 eq), 2M aq Na$_2$CO$_3$ (1 mL) and PdCl$_2$(PPh$_3$)$_2$ (0.032 g, 0.045 mmol, 0.2 eq) was heated at 110° C. for 24 h. The solvent was removed in vacuo and the residue was redissolved in DCM/water (150 mL) and extracted with DCM (2×80 mL). The organic layer was dried (MgSO$_4$), filtered and evaporated. The residue was triturated from MeOH and filtered off. The solid was purified by column chromatography (0-5% MeOH in DCM) to give the desired product (15 mg, 16%) as a yellow solid. HPLC-MS (5-100% B in 8 min at 0.8 mL): $t_R$=5.97 min, [M+H]+ m/z 405.1; $^1$H NMR (300 MHz, DMSO) δ 8.86 (d, J=1.8 Hz, 1H), 8.45 (d, J=2.0 Hz, 1H), 7.80 (s, 1H), 7.40 (t, J=8.1 Hz, 1H), 7.20 (m, 2H), 6.99 (dd, J=9.1, 2.0 Hz, 1H), 6.75 (s, 2H), 3.00 (s, 6H).

Intermediate X

5-Iodo-2-(6-methyl-pyridin-3-yl)-imidazo[2,1-b][1,3,4]thiadiazole

A mixture of 2-bromo-5-iodoimidazo[2,1-b][1,3,4]thiadiazole (169 mg, 0.512 mmol, 1 eq), 2-picoline-5-boronic acid pinacol ester (137 mg, 0.614 mmol, 1.2 eq), PdCl$_2$(PPh$_3$)$_2$ (73 mg, 0.102 mmol, 0.2 eq) and 2M aq Na$_2$CO$_3$ (1.5 mL) in dioxane (7 mL) was heated at 110° C. for 2 h. The solvent was removed under reduced pressure, redissolved in dichloromethane and washed with water. The organic layer was dried over Na$_2$SO$_4$ and concentrated. The residue (226. mg) was used in the next step of the synthesis without further purification. HPLC-MS (10-95% B in 4 min at 0.5 mL+2 min 100% B, flow 0.8 mUrnin, 50° C.): $t_R$=3.79 min, [M+H]+ m/z 342.9.

Example 43

5-[2-(6-Methyl-pyridin-3-yl)-imidazo[2,1-b][1,3,4]thiadiazol-5-yl]-3-trifluoromethyl-pyridin-2-ylamine A mixture of 5-Iodo-2-(6-methyl-pyridin-3-yl)-imidazo[2,1-b][1,3,4]thiadiazole (226 mg, 0.661 mmol, 1 eq), 5-(4,4,5,5-tetramethyl-[1,3,2]dioxaborolan-2-yl)-3-trifluoromethyl-pyridin-2-ylamine (228 mg, 0.793 mmol, 1.2 eq), PdCl$_2$(PPh$_3$)$_2$ (95 mg, 0.132 mmol, 0.2 eq) and 2M aq Na$_2$CO$_3$ (1.6 mL) in dioxane (7 mL) was heated at 110° C. for 90 min. The solvent was removed under reduced pressure and the residue was suspended in water and filtered. The solid was washed with diethylether, methanol and acetone. The residue was purified by HPLC to afford the desired product (4.7 mg, 2%). HPLC-MS (5-100% B in 8 min at 0.8 mL): $t_R$=5.23 min, [M+H]+ m/z 377.0; $^1$H NMR (300 MHz, DMSO) δ 9.02 (s, 1H), 8.87 (s, 1H), 8.36 (s, 1H), 8.25 (dd, J=8.1, 2.2 Hz, 1H), 7.81 (s, 1H), 7.52 (d, J=8.2 Hz, 1H), 6.75 (s, 2H), 2.59 (s, 3H).

Intermediate Y

5-Iodo-2-[4-(morpholine-4-sulfonyl)-phenyl]-imidazo[2,1-b][1,3,4]thiadiazole

A mixture of 2-bromo-5-iodoimidazo[2,1-b][1,3,4]thiadiazole (200 mg, 0.44 mmol), 4-(4-morpholinylsulfonyl)phenylboronic acid (144 mg, 0.52 mmol), $PdCl_2(PPh_3)_2$ (60 mg, 0.088 mmol) and 2M aq $Na_2CO_3$ (1.2 mL) in dioxane (8 mL) was heated at 90° C. for 18 h. The solvent was removed in vacuo and the residue was triturated from EtOAc and filtered. The filtrate was evaporated and the residue was recrystallyzed from MeOH to give the desired product (89 mg, 31%) as a brown solid.

Example 44

5-{2-[4-(Morpholine-4-sulfonyl)-phenyl]-imidazo[2,1-b][1,3,4]thiadiazol-5-yl}-3-trifluoromethyl-pyridin-2-ylamine A mixture of 5-Iodo-2-[4-(morpholine-4-sulfonyl)-phenyl]-imidazo[2,1-b][1,3,4]thiadiazole (85 mg, 0.18 mmol), 5-(4,4,5,5-tetramethyl-[1,3,2]dioxaborolan-2-yl)-3-trifluoromethyl-pyridin-2-ylamine (60 mg, 0.27 mmol), $PdCl_2(PPh_3)_2$ (26 mg, 0.037 mmol) and 2M aq $Na_2CO_3$ (0.5 mL) in dioxane (4 mL) was heated at 90° C. for 18 h. On cooling, the solvents were removed in vacuo and the residue was triturated from EtOAc and filtered off. The filtrate was evaporated and the residue was recrystallyzed from MeOH, filtered and washed with water. The solid was purified by column chromatography (DCM/MeOH) to afford the desired product (31 mg, 34%) as a yellow solid. HPLC-MS (5-100% B in 8 min at 0.8 mL): $t_R$=5.12 min, [M+H]+ m/z 511.2; $^1H$ NMR (300 MHz, DMSO) δ 8.89 (s, 1H), 8.36 (s, 1H), 8.26 (d, J=8.3 Hz, 2H), 7.97 (d, J=8.3 Hz, 2H), 7.84 (s, 1H), 6.77 (s, 2H), 3.65 (s, 4H), 2.95 (s, 4H).

Intermediate Z

5-Iodo-2-[3-(morpholine-4-sulfonyl)-phenyl]-imidazo[2,1-b][1,3,4]thiadiazole

A mixture of 2-bromo-5-iodoimidazo[2,1-b][1,3,4]thiadiazole (0.05 g, 0.152 mmol), 4-methylpyridine-3-boronic acid (0.023 g, 0.167 mmol), $PdCl_2(dppf)$ (0.025 g, 0.03 mmol) and sat $K_2CO_3$ (0.25 ml) in dioxane (1.5 mL) was added heated at 110° C. overnight. The reaction mixture was cooled, diluted with DCM and washed with water. The organic layer was dried ($Na_2SO_4$), filtered and evaporated. The residue was purified by column chromatography (DCM/MeOH, 0 to 40%) to give the desired product (31 mg, 22%). HPLC-MS (10-95% B in 4 min at 0.5 mL+2 min 100% B, flow 0.8 mL/min, 50° C.): $t_R$=4.36 min, [M+H]+ m/z 477.1.

Example 45

5-{2-[3-(Morpholine-4-sulfonyl)-phenyl]-imidazo[2,1-b][1,3,4]thiadiazol-5-yl}-3-trifluoromethyl-pyridin-2-ylamine A mixture of 5-Iodo-2-[3-(morpholine-4-sulfonyl)-phenyl]-imidazo[2,1-b][1,3,4]thiadiazole (18 mg, 0.053 mmol), 5-(4,4,5,5-tetramethyl-[1,3,2]dioxaborolan-2-yl)-3-trifluoromethyl-pyridin-2-ylamine (20 mg, 0.068 mmol), $PdCl_2$ (dppf) (9 mg, 0.011 mmol) and sat $K_2CO_3$ (0.22 mL) in DME (0.5 mL) was heated under microwave irradiation at 120° C. for 30 min. The reaction mixture was cooled, diluted with DCM and washed with water. The organic layer was dried ($Na_2SO_4$), filtered and evaporated. The residue was purified by column chromatography (5% MeOH in DCM) to give the desired product (6.2 mg, 19%). HPLC-MS (5-100% B in 8 min at 0.8 mL): $t_R$=5.13 min, [M+H]+ m/z 511.1; $^1H$ NMR (300 MHz, DMSO) δ 8.75 (s, 1H), 8.29 (s, 1H), 8.20 (d, J=7.6 Hz, 1H), 8.10 (s, 1H), 7.83 (m, 2H), 7.72 (s, 1H), 6.65 (s, 2H), 3.53 (m, 4H), 2.84 (m, 4H).

Intermediate AA

N-[3-(5-Iodo-imidazo[2,1-b][1,3,4]thiadiazol-2-yl)-phenyl]-acetamide

A mixture of 2-bromo-5-iodoimidazo[2,1-b][1,3,4]thiadiazole (0.127 g, 0.4 mmol, 1 eq), 3-acetamidobenzeneboronic acid (0.091 g, 1.3 equiv, 1.3 eq), dichlorobis(triphenylphosphine)palladium(II) (0.055 g, 02 eq) and 2M aq $Na_2CO_3$ (1.1 ml) in dioxane (5 mL) was heated at 110° C. for 3 h. The solvent was removed under reduced pressure, redissolved in ethylacetate and washed with water. The organic layer was dried over $Na_2SO_4$, filtered and concentrated. The residue (0.167 g) was used in the next step of the synthesis without further purification. HPLC-MS (10-95% B in 4 min at 0.5 mL+2 min 100% B, flow 0.8 mL/min, 50° C.): $t_R$=4.03 min, [M+H]+ m/z 385.1.

Example 46

N-{3-[5-(6-Amino-5-trifluoromethyl-pyridin-3-yl)-imidazo[2,1-b][1,3,4]thiadiazol-2-yl]-phenyl}-acetamide A mixture of N-[3-(5-Iodo-imidazo[2,1-b][1,3,4]thiadiazol-2-yl)-phenyl]-acetamide (0.16 g, 0.416 mmol, 1 eq), 5-(4,4,5,5-tetramethyl-[1,3,2]dioxaborolan-2-yl)-3-trifluoromethyl-pyridin-2-ylamine (0.12 g, 0.416 mmol, 1 eq), 2M aq $Na_2CO_3$ (0.9 mL) and $PdCl_2(PPh_3)_2$ (60 mg, 0.083 mmol, 0.2 eq) in dioxane (5 mL) was heated at 110° C. for 90 min. The solvent was removed under reduced pressure and the residue was redissolved in DCM and washed with water. The organic layer was dried over $Na_2SO_4$, filtered and evaporated. The residue was purified by flash-chromatography (DCM:MeOH, 5 to 15%) and by HPLC to afford the desired product (7 mg, 4%). HPLC-MS (5-100% B in 8 min at 0.8 mL): $t_R$=4.74 min, [M+H]+ m/z 419.1; $^1H$ NMR (300 MHz, DMSO) δ 10.30 (s, 1H), 8.89 (s, 1H), 8.32 (m, 2H), 7.81 (m, 2H), 7.62 (d, J=7.8 Hz, 1H), 7.54 (t, J=7.9 Hz, 1H), 6.75 (s, 2H), 2.09 (s, 3H).

Intermediate AB

5-Iodo-2-(5-methoxy-pyridin-3-yl)-imidazo[2,1-b][1,3,4]thiadiazole

A mixture of 2-bromo-5-iodoimidazo[2,1-b][1,3,4]thiadiazole (100 mg, 0.303 mmol, 1 eq), 3-methoxypyridine-5-boronic acid pinacol ester (78 mg, 0.333 mmol, 1 eq), $PdCl_2$ (dppf) (25 mg, 0.030 mmol, 0.1) and sat $K_2CO_3$ (0.6 mL) in dioxane (4 mL) was heated at 110° C. for 2 days. Additional amount of catalyst (0.05 eq) was added and the reaction mixture was heated under microwave irradiation at 130° C. for 2 h. The solvent was removed, the residue was diluted with EtOAc, sonicated and flushed through a plug of Celite. The filtrate was concentrated and the residue was purified by column chromatography (MeOH in DCM, 0 to 10%) to give the desired product (26 mg, 24%). HPLC-MS (10-95% B in 4 min at 0.5 mL+2 min 100% B, flow 0.8 mL/min, 50° C.): $t_R$=3.97 min, [M+H]+ m/z 359.0.

Example 47

5-[2-(5-Methoxy-pyridin-3-yl)-imidazo[2,1-b][1,3,4]thiadiazol-5-yl]-3-trifluoromethyl-pyridin-2-ylamine A mixture of 5-Iodo-2-(5-methoxy-pyridin-3-yl)-imidazo[2,1-b][1,3,4]thiadiazole (26 mg, 0.073 mmol, 1.0 eq), 5-(4,4,5,5-tetramethyl-[1,3,2]dioxaborolan-2-yl) -3-trifluoromethyl-pyridin-2-ylamine (27 mg, 0.096 mmol, 1.3 eq), PdCl$_2$(dppf) (12 mg, 0.015 mmol, 0.2 eq), sat. K$_2$CO$_3$ (0.5 mL) in DME (4 mL) was heated under microwave irradiation at 120° C. for 30 min. The solvent was removed and the residue was diluted with DCM and washed with H$_2$O and brine. The organic layer was dried over Na$_2$SO$_4$, filtered and evaporated. The residue was purified by column chromatography (Isolute Si II; MeOH in DCM, 0 to 3%) to give the desired product (12 mg, 42%). HPLC-MS (5-100% B in 8 min at 0.8 mL): $t_R$=4.76 min, [M+H]+ m/z 393.0; $^1$H NMR (300 MHz, DMSO) δ 8.87 (d, J=1.8 Hz, 1H), 8.75 (d, J=1.7 Hz, 1H), 8.53 (d, J=2.8 Hz, 1H), 8.38 (d, J=2.0 Hz, 1H), 7.85 (m, 2H), 6.76 (s, 2H), 3.96 (s, 3H).

Intermediate AC 5-(5-iodoimidazo[2,1-b][1,3,4]thiadiazol-2-yl)-2-methoxypyridin-3-amine Dioxane (5 mL) and 2M aq Na$_2$CO$_3$ (1.5 mL) were added to 2-bromo-5-iodoimidazo[2,1-b][1,3,4]thiadiazole (200 mg) and (5-amino-6-methoxypyridin-3-yl)boronic acid pinacol ester (200 mg), and the suspension was degassed under vacuum and filled with argon (3×). PdCl$_2$(PPh$_3$)$_2$ (90 mg) was quickly added, and the reaction mixture was stirred at reflux for 2 h. Water was added, and a precipitate formed that was filtered off and washed with water followed by ether and ether/MeOH 10:1 and dried to give the desired product (150 mg) that was used without further purification in the subsequent step. HPLC-MS (10-95% B in 4 min at 0.5 mL+2 min 100% B, flow 0.8 mL/min, 50° C.): $t_R$=4.12 min, [M+H]+ m/z 373.9.

Intermediate AD 2,4-Difluoro-N-[2-methoxy-5-(5-iodoimidazo[2,1-b][1,3,4]thiadiazol-2-yl)-pyridin-3-yl]-benzenesulfonamide Sulfonyl chloride (0.06 mL) was added at RT to a solution of 5-(5-iodoimidazo[2,1-b][1,3,4]thiadiazol-2-yl)-2-methoxypyridin-3-amine in pyridine (1 mL). The mixture was stirred under Ar overnight and additional 5 h after addition of further 0.05 mL of sulfonyl chloride. Water (10 mL) was added, and the mixture was extracted with CHCl$_3$/iPrOH 1:1. The organic phase was separated, dried (MgSO$_4$) and concentrated affording a crude product that was treated with DCM, MeOH and ether. The precipitate that formed was separated by filtration, and the filtrate was purified by silica gel chromatography to afford the desired product (102 mg).

HPLC-MS (10-95% B in 4 min at 0.5 mL+2 min 100% B, flow 0.8 mL/min, 50° C.): $t_R$=4.59 min, [M+H]+ m/z 550.0.

Example 48

2,4-Difluoro-N-[2-methoxy-5-(5-pyridazin-4-yl-imidazo[2,1-b][1,3,4]thiadiazol-2-yl)-pyridin-3-yl]-benzenesulfonamide Dioxane (2 mL) and 2M aq Na$_2$CO$_3$ (0.5 mL) were added to 2,4-difluoro-N-[2-methoxy-5-(5-iodoimidazo[2,1-b][1,3,4]thiadiazol-2-yl)-pyridin-3-yl]-benzenesulfon-amide (100 mg) and pyridazin-4-boronic acid pinacol ester (80 mg), and the suspension was degassed under vacuum and filled with argon (2×). The catalyst (30 mg) was quickly added, and the reaction mixture was stirred at reflux for 2 h. Further boronate (50 mg) was added, and the mixture was degassed again, then more catalyst was added (25 mg) and stirring was continued at reflux for 4 h. The solvents were evaporated, and the residue was stirred in water for 36 h. The precipitate that had formed was removed by filtration, and the filtrate was concentrated and taken up in aq. NH$_4$Cl. A precipitate formed overnight and was filtered off, washed with water followed by ether and dried. The solid was purified by flash chromatography (DCM/MeOH 98:2 to 9:1, affording 24 mg of crude product) and subsequently by preparative HPLC to give the desired product (5 mg). HPLC-MS (5-100% B in 8 min at 0.8 mL): $t_R$=4.57 min, [M+H]+ m/z 502.1; $^1$H NMR (300 MHz, DMSO) δ=10.56 (s, 1H), 9.82 (s, 1H), 9.25 (d, J=5.5 Hz, 1H), 8.57 (s, 1H), 8.35-8.16 (m, 2H), 8.06 (s, 1H), 7.79 (dd, J=15.0, 8.6 Hz, 1H), 7.50 (s, 1H), 7.20 (t, J=8.3 Hz, 1H), 3.70 (s, 3H) ppm.

Intermediate AE 3-(trifluoromethyl)-5-(imidazo[2,1-b][1,3,4]thiadiazol-2-yl)pyridin-2-amine A solution of 2-bromo-imidazo[2,1-b][1,3,4]thiadiazole (0.469 g, 2.3 mmol, 1 eq), 3-(trifluoromethyl)-5-(4,4,5,5-tetramethyl-1,3,2-dioxaborolan-2-yl)pyridin-2-amine (1.7 g, 3.5 mmol, 1.5 eq), dioxane (8 mL) and a sat. aq. solution of K$_2$CO$_3$ (1 mL) was degassed (N$_2$, 5 min) at RT. Pd(Ph$_3$P)$_2$Cl$_2$ (0.404 g, 0.250 mmol, 1 eq) was added, and the reaction mixture was heated at 110° C. under N$_2$ for 2 h. The solvent was evaporated, and the residue was taken up in AcOEt and n-BuOH and washed with water. The organic phase was separated, dried (Na$_2$SO$_4$), filtered and concentrated. The residue was treated with MeOH, filtered off and dried to give the desired product (0.244 g, 37%). HPLC-MS (10-95% B in 4 min at 0.5 mL+2 min 100% B, flow 0.8 mL/min, 50° C.): $t_R$=3.61 min, [M+H]+ m/z 286.0.

Intermediate AF 3-(trifluoromethyl)-5-(5-iodoimidazo[2,1-b][1,3,4]thiadiazol-2-yl)pyridin-2-amine 3-(trifluoromethyl)-5-(imidazo[2,1-b][1,3,4]thiadiazol-2-yl)pyridin-2-amine (0.244 g, 0.855 mmol, 1 eq) was dissolved in DMF (5 mL), and NIS (0.212 g, 0.941 mmol, 1.1 eq) was added. The reaction mixture was stirred at RT under N$_2$ for 18 h and then poured into an aqueous solution of sodium thiosulfate (10%) and extracted with AcOEt. The organic phase was separated, washed with ice-water and ammonium chloride, dried (Na$_2$SO$_4$), filtered and evaporated to dryness. The residue was treated with Et$_2$O, filtered off and dried affording the desired product (0.240 g, 68%). HPLC-MS (10-95% B in 4 min at 0.5 mL+2 min 100% B, flow 0.8 mL/min, 50° C.): $t_R$=4.27 min, [M+H]+ m/z 411.9.

Example 49

5-[5-(4-Methanesulfonyl-phenyl)-imidazo[2,1-b][1,3,4]thiadiazol-2-yl]-3-trifluoromethyl-pyridin-2-ylamine 3-(trifluoromethyl)-5-(5-iodoimidazo[2,1-b][1,3,4]thiadiazol-2-yl)pyridin-2-amine (0.100 g, 0.243 mmol, 1 eq) was dissolved in dioxane (1.5 mL), then 4-(methylsulfonyl)phenylboronic acid (0.078 g, 0.389 mmol, 1.6 eq) was added followed by 2M aq. $Na_2CO_3$ (0.5 mL, 4 eq). The suspension was degassed ($N_2$, 15 min) and equipped with an argon balloon. $Pd(Ph_3P)_2Cl_2$ (0.043 g, 0.061 mmol, 0.25 eq) was quickly added, and the reaction flask was placed in a pre-heated bath (115° C.). After stirring at reflux temperature for 3 h the mixture was cooled to RT and concentrated. The residue was taken up in water, and the solid obtained was filtered off, washed with $Et_2O$ and dried. The crude product was suspended in $CH_3CN$ at 50° C., filtered off and dried in vacuo to afford the desired product (0.061 g, 57%). HPLC-MS (10-95% B in 4 min at 0.5 mL+2 min 100% B, flow 0.8 mL/min, 50° C.): $t_R$=4.04 min, [M+H]+ m/z 440.0; $^1$H-NMR (DMSO-$d_6$+TFA): δ=8.88 (1H, s), 8.36 (2H, d, J=8.4 Hz), 8.28 (1H, s), 8.17 (1H, s), 8.06 (2H, d, J=8.4 Hz), 3.24 (3H, s) ppm.

Example 50

5-[5-(6-Fluoro-pyridin-3-yl)-imidazo[2,1-b][1,3,4]thiadiazol-2-yl]-3-trifluoromethyl-pyridin-2-ylamine 3-(trifluoromethyl)-5-(5-iodoimidazo[2,1-b][1,3,4]thiadiazol-2-yl)pyridin-2-amine (0.100 g, 0.243 mmol, 1 eq) was dissolved in dioxane (1.5 mL), then 2-fluoropyridine-5-boronic acid (0.055 g, 0.389 mmol, 1.6 eq) was added followed by 2M aq. $Na_2CO_3$ (0.5 mL, 4 eq). The suspension was degassed ($N_2$, 15 min) and equipped with an argon balloon. $Pd(Ph_3P)_2Cl_2$ (0.043 g, 0.061 mmol, 0.25 eq) was quickly added, and the reaction flask was placed in a pre-heated bath (115° C.). After stirring at reflux temperature for 3 h the mixture was cooled to RT and concentrated. The residue was suspended in EtOAc and water, and the clear water phase was removed. The remainder was concentrated to dryness and triturated with $Et_2O$, filtered off, washed with $Et_2O$ and dried in vacuo to afford the desired product (0.049 g, 53%). HPLC-MS (5-100% B in 8 min at 0.8 mL): $t_R$=5.14 min, [M+H]+ m/z 381.0; $^1$H-NMR (DMSO-$d_6$): δ=8.93 (1H, bs), 8.84 (1H, bs), 8.67-8.58 (1H, m), 8.24 (1H, bs), 7.92 (1H, s), 7.42-7.34 (3H, m) ppm Example 51

4-[2-(6-Amino-5-trifluoromethyl-pyridin-3-yl)-imidazo[2,1-b][1,3,4]thiadiazol-5-yl]-2-methoxy-benzoic acid methyl ester To a suspension of 3-(trifluoromethyl)-5-(5-iodoimidazo[2,1-b][1,3,4]thiadiazol-2-yl)pyridin-2-amine (0.500 g, 1.216 mmol, 1 eq), 3-methoxy-4-methoxycarbonylphenylboronic acid (0.306 g, 1.459 mmol, 1.2 eq), Pd(dppf)$Cl_2$.DCM (0.105 g, 0.126 mmol, 0.1 eq) in DME was added a sat. aq. solution of $Na_2CO_3$ (2 mL). The reaction mixture was heated in a sealed tube at 90° C. over the weekend. The solid was filtered off, washed with MeOH and treated with a mixture of DCM and MeOH. The solid was removed by filtration, and the filtrate was evaporated to dryness to give the desired product (0.005 g). HPLC-MS (5-100% B in 8 min at 0.8 mL): $t_R$=5.50 min, [M+H]+ m/z 450.1; $^1$H NMR (300 MHz, DMSO) δ=8.82 (d, J=1.8, 1H), 8.24 (s, 1H), 8.01 (s, 1H), 7.87 (s, 1H), 7.80 (d, J=8.1, 1H), 7.71 (d, J=8.2, 1H), 7.42 (br s, 2H), 3.95 (s, 3H), 3.80 (s, 3H) ppm.

Example 52

Compounds of the examples were assayed for their PI3K binding activity. Compounds of the examples displayed a range of PI3K binding activities of less than 10 nM to about 10 μM (for example, as demonstrated by representative examples in Table 1 below). For example, compounds of the examples/invention had PI3K binding activity with $IC_{50}$ values of less than 50 nM.

TABLE 1

Inhibition (%) of PI3Kα activity of representative examples at 10 μM compound concentration.

| Example | Inh (%) at 10 μM |
|---|---|
| 1 | 68 |
| 2 | 100 |
| 3 | 97 |
| 4 | 81 |
| 5 | 70 |
| 6 | 85 |
| 7 | 100 |
| 9 | 77 |
| 11 | 83 |
| 16 | 97 |
| 17 | 95 |
| 27 | 99 |
| 50 | 97 |

For example, certain exemplary compounds of the invention had PI3K binding activity with $IC_{50}$ values of less than 50 nM. The following table shows $IC_{50}$ values for representative examples.

TABLE 2

Inhibition of PI3Kα activity expressed as $IC_{50}$ values [μM] for representative examples.

| Example | $IC_{50}$ [μM] PI3Kα |
|---|---|
| 5 | 2.88 |
| 15 | 0.115 |
| 17 | 0.063 |
| 18 | 0.033 |
| 23 | 0.447 |
| 30 | 0.454 |
| 31 | 0.028 |
| 36 | 0.095 |
| 40 | 0.676 |
| 41 | 0.050 |
| 43 | 0.062 |
| 45 | 0.437 |
| 47 | 0.021 |
| 51 | 0.018 |

Biological activity in PI3Kα for certain examples is represented in the following table by semi-quantitative results: <0.1 μM (*), 0.1-1 μM () and 1-50 μM (*).

| Structure | Example | Activity |
|---|---|---|
| 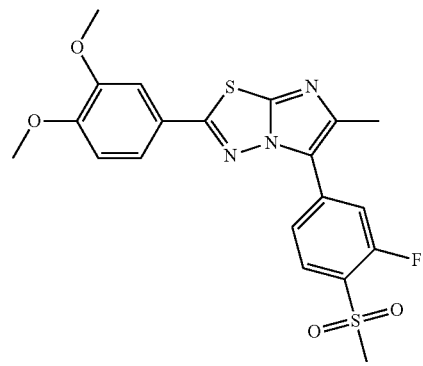 [SMILES: COc1ccc(-c2nn3c(-c4ccc(S(C)(=O)=O)c(F)c4)c(C)nc3s2)cc1OC] | 1 | ** |
| 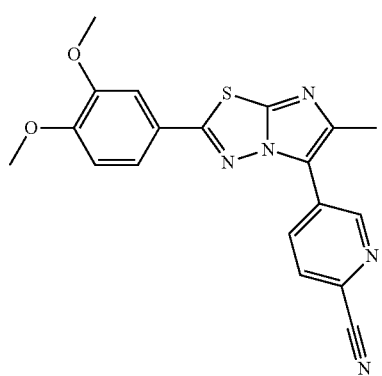 | 2 | ** |
| 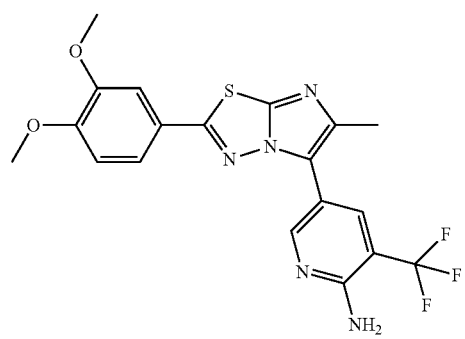 [SMILES: COc1ccc(-c2nn3c(-c4cnc(N)c(C(F)(F)F)c4)c(C)nc3s2)cc1OC] | 3 | *** |
| 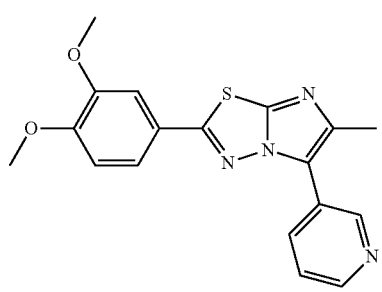 | 4 | * |

-continued

| Structure | Example | Activity |
|---|---|---|
| (structure) | 5 | * |
| (structure) | 6 | ** |
| (structure) | 7 | ** |
| (structure) | 8 | * |

-continued
| Structure | Example | Activity |
|---|---|---|
| 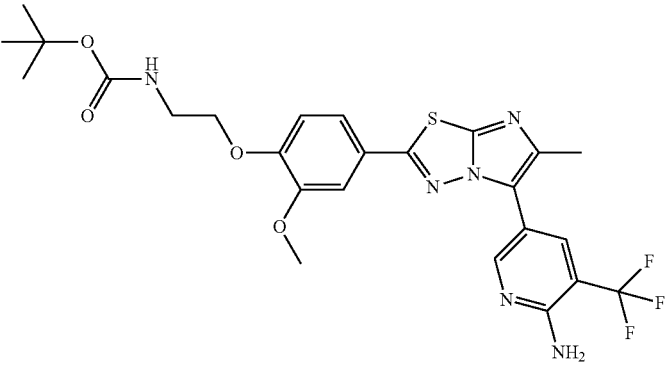 [SMILES: COc1cc(-c2nn3c(-c4cnc(N)c(C(F)(F)F)c4)c(C)nc3s2)ccc1OCCNC(=O)OC(C)(C)C] | 9 | * |
| 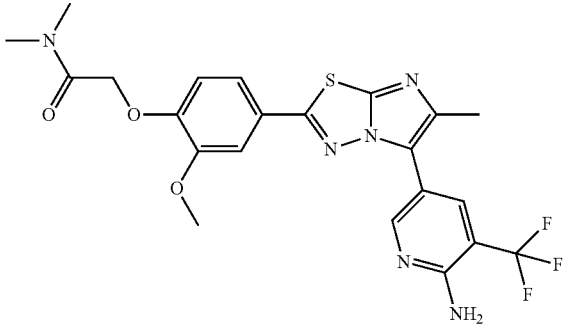 [SMILES: COc1cc(-c2nn3c(-c4cnc(N)c(C(F)(F)F)c4)c(C)nc3s2)ccc1OCC(=O)N(C)C] | 10 | * |
| 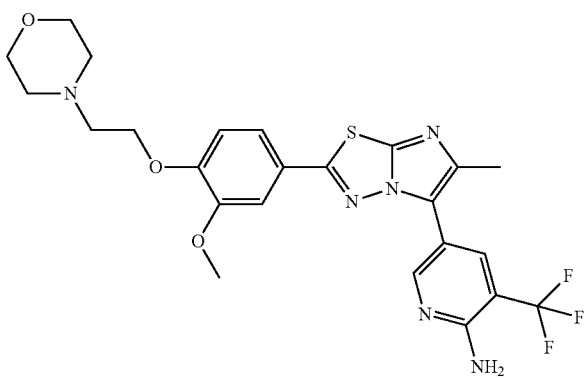 [SMILES: COc1cc(-c2nn3c(-c4cnc(N)c(C(F)(F)F)c4)c(C)nc3s2)ccc1OCCN1CCOCC1] | 11 | * |
| 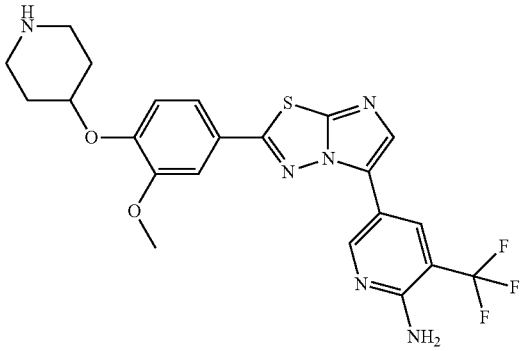 [SMILES: COc1cc(-c2nn3c(-c4cnc(N)c(C(F)(F)F)c4)cnc3s2)ccc1OC1CCNCC1] | 12 | *** |

-continued

| Structure | Example | Activity |
|---|---|---|
| (structure) | 13 | * |
| (structure) | 14 | * |
| (structure) | 15 | ** |
| (structure) | 16 | *** |

-continued
| Structure | Example | Activity |
|---|---|---|
| 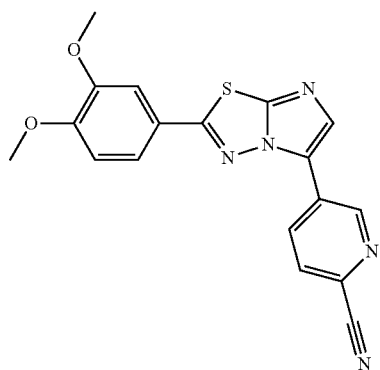 [SMILES: COc1ccc(-c2nn3c(-c4ccc(C#N)nc4)cnc3s2)cc1OC] | 17 | *** |
| 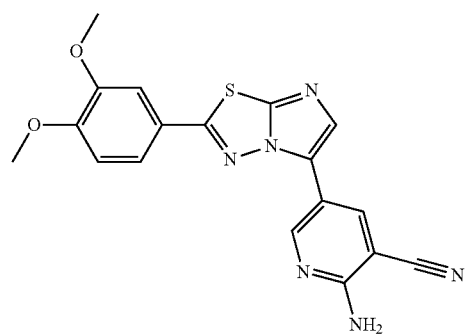 [SMILES: COc1ccc(-c2nn3c(-c4cnc(N)c(C#N)c4)cnc3s2)cc1OC] | 18 | *** |
| 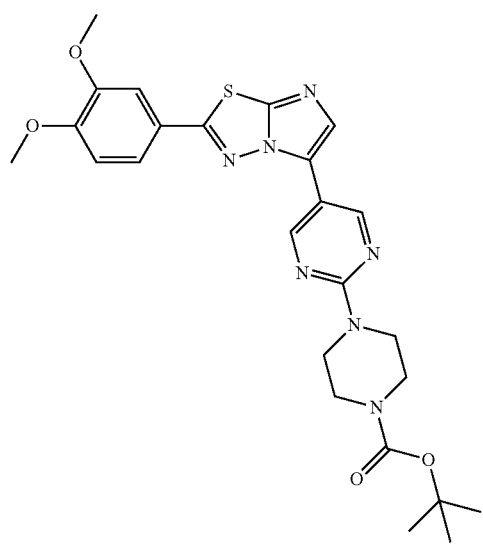 [SMILES: COc1ccc(-c2nn3c(-c4cnc(N5CCN(C(=O)OC(C)(C)C)CC5)nc4)cnc3s2)cc1OC] | 19 | * |

-continued
| Structure | Example | Activity |
|---|---|---|
| 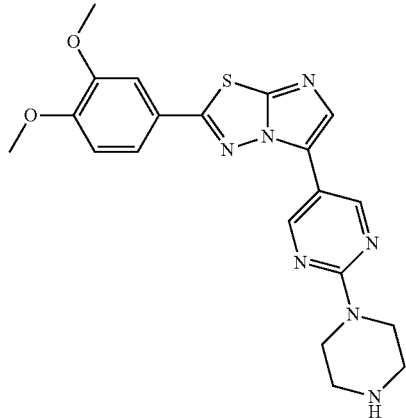 [SMILES: COc1ccc(-c2nn3c(-c4cnc(N5CCNCC5)nc4)cnc3s2)cc1OC] | 20 | ** |
| 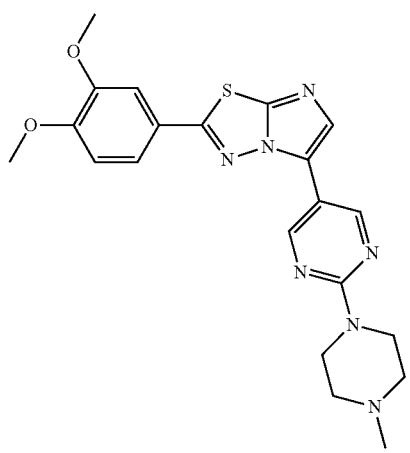 [SMILES: COc1ccc(-c2nn3c(-c4cnc(N5CCN(C)CC5)nc4)cnc3s2)cc1OC] | 21 | ** |
| 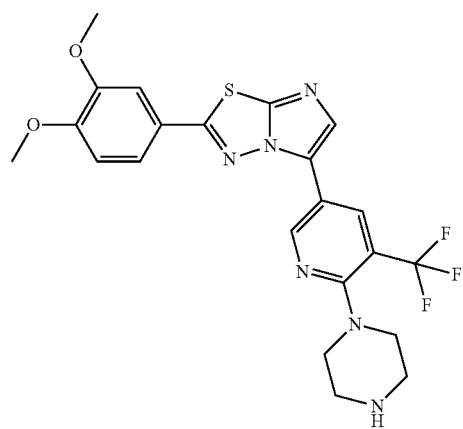 [SMILES: COc1ccc(-c2nn3c(-c4cnc(N5CCNCC5)c(C(F)(F)F)c4)cnc3s2)cc1OC] | 22 | ** |

-continued

| Structure | Example | Activity |
|---|---|---|
| 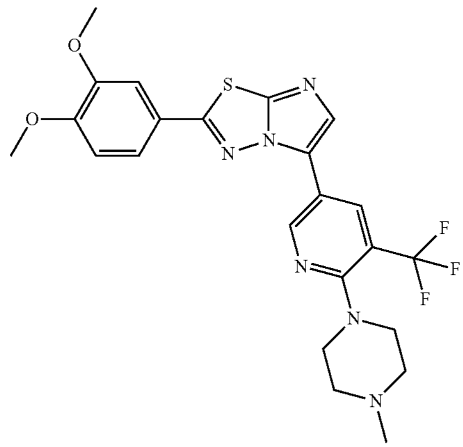 [SMILES: COc1ccc(-c2nn3c(-c4cnc(N5CCN(C)CC5)c(C(F)(F)F)c4)cnc3s2)cc1OC] | 23 | ** |
| 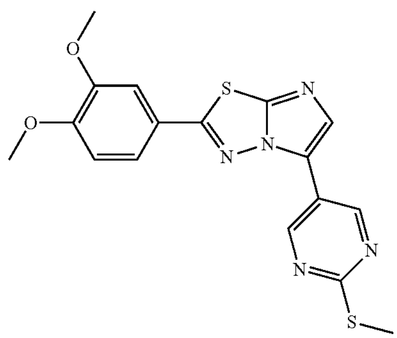 | 24 | ** |
| 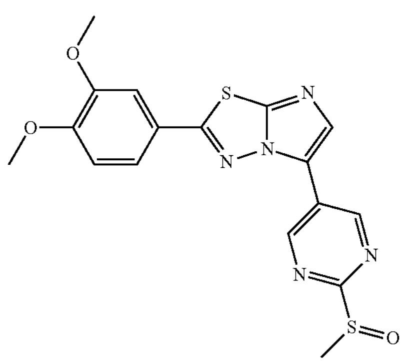 [SMILES: COc1ccc(-c2nn3c(-c4cnc(S(C)=O)nc4)cnc3s2)cc1OC] | 25 | ** |
| 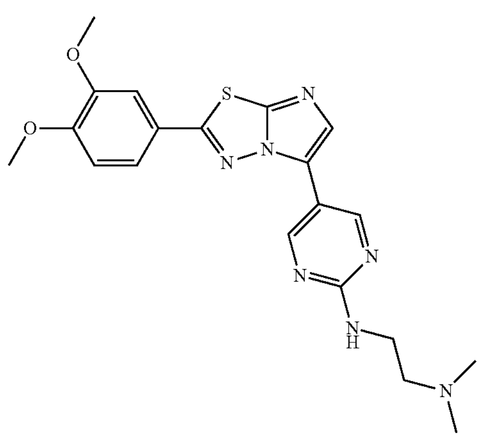 | 26 | ** |

-continued

| Structure | Example | Activity |
|---|---|---|
| (structure) | 27 | *** |
| (structure) | 28 | ** |
| (structure) | 29 | *** |
| (structure) | 30 | ** |
| (structure) | 31 | *** |

-continued
| Structure | Example | Activity |
|---|---|---|
| 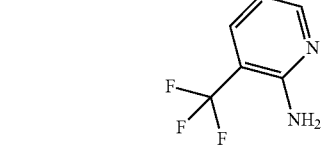 | 32 | *** |
| 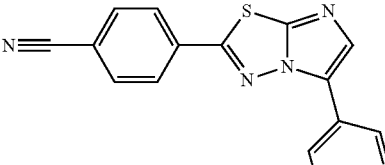 | 33 | ** |
| 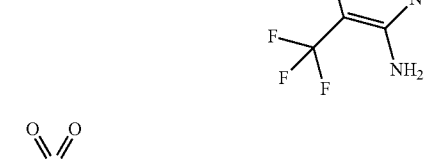 | 34 | *** |
| 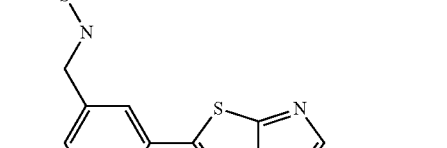 | 35 | *** |
| 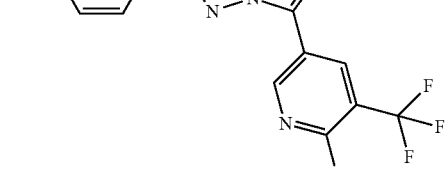 | 36 | *** |

-continued
| Structure | Example | Activity |
|---|---|---|
| 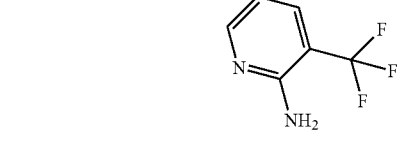 | 37 | *** |
| 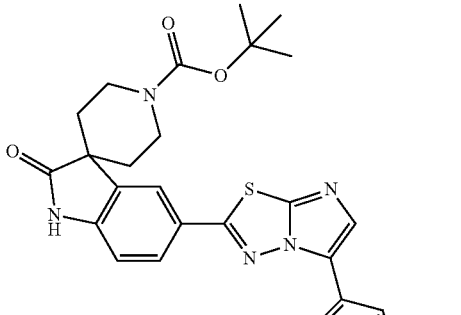 | 38 | * |
| 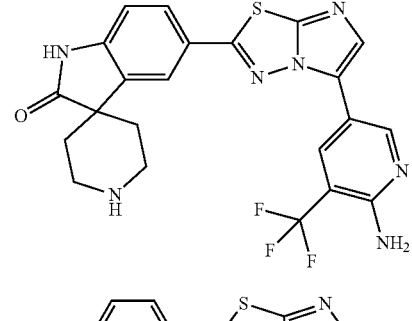 | 39 | *** |
| 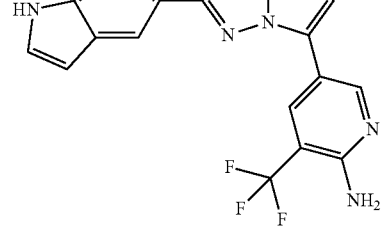 | 40 | ** |
| 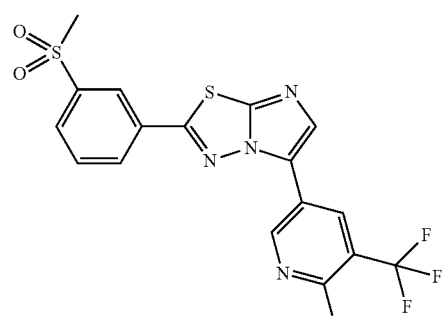 | 41 | *** |

-continued

| Structure | Example | Activity |
|---|---|---|
| (structure) | 42 | ** |
| (structure) | 43 | *** |
| (structure) | 44 | ** |
| (structure) | 45 | ** |
| (structure) | 46 | *** |

-continued
| Structure | Example | Activity |
|---|---|---|
| 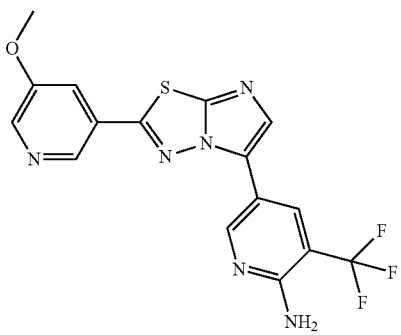 [SMILES: COc1cncc(-c2nn3c(-c4cnc(N)c(C(F)(F)F)c4)cnc3s2)c1] | 47 | *** |
| 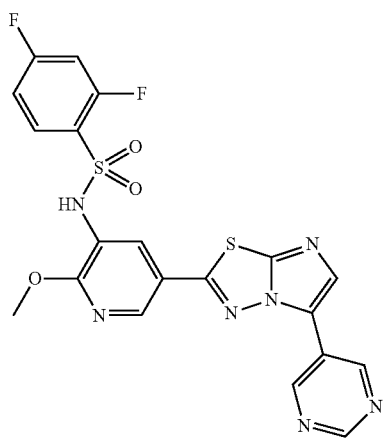 [SMILES: COc1ncc(-c2nn3c(-c4cncnc4)cnc3s2)cc1NS(=O)(=O)c1ccc(F)cc1F] | 48 | *** |
| 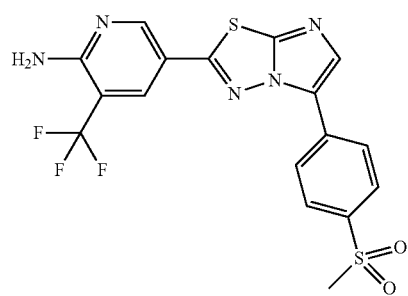 [SMILES: CS(=O)(=O)c1ccc(-c2cnc3sc(-c4cnc(N)c(C(F)(F)F)c4)nn23)cc1] | 49 | *** |
| 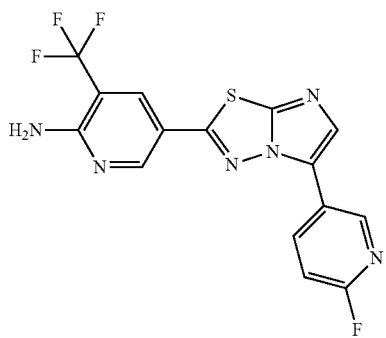 [SMILES: Nc1ncc(-c2nn3c(-c4ccc(F)nc4)cnc3s2)cc1C(F)(F)F] | 50 | ** |

| Structure | Example | Activity |
|---|---|---|
| (structure shown) | 51 | *** |

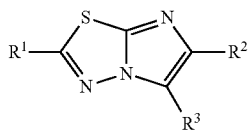

The invention claimed is:

1. A compound of formula I, $$\text{(structure I)}$$

wherein:

$R^1$ represents:
  (i) aryl substituted with one or more substituents selected from $A^1$; or
  (ii) heteroaryl optionally substituted with one or more substituents selected from $A^2$;

$R^2$ represents hydrogen or $C_{1-3}$ alkyl optionally substituted by one or more fluoro atoms;

$R^3$ represents heteroaryl, which is optionally substituted by one or more substituents selected from $A^4$;

each $A^1$, $A^2$ and $A^4$ independently represents, on each occasion when used herein:
  (i) $Q^1$;
  (ii) $C_{1-12}$ alkyl or heterocycloalkyl, both of which are optionally substituted by one or more substituents selected from =O, =S, =N($R^{10a}$) and $Q^2$; or
  (iii) aryl or heteroaryl, both of which are optionally substituted by one or more substituents selected from $Q^3$;

each $Q^1$, $Q^2$ and $Q^3$ independently represents, on each occasion when used herein:
  halogen, —CN, —NO$_2$, —N($R^{10a}$)$R^{11a}$, —OR$^{10a}$, —C(=Y)—R$^{10a}$, —C(=Y)—OR$^{10a}$, —C(=Y)N($R^{10a}$)$R^{11a}$, —OC(=Y)—R$^{10a}$, —OC(=Y)—OR$^{10a}$, —OC(=Y)N($R^{10a}$)$R^{11a}$, —OS(O)$_2$OR$^{10a}$, —OP(=Y)(OR$^{10a}$)(OR$^{11a}$), —OP(OR$^{10a}$)(OR$^{11a}$), —N($R^{12a}$)C(=Y)$R^{11a}$, —N($R^{12a}$)C(=Y)OR$^{11a}$, —N($R^{12a}$)C(=Y)N($R^{10a}$)$R^{11a}$, —NR$^{12a}$S(O)$_2$R$^{10a}$, —NR$^{12a}$S(O)$_2$N($R^{10a}$)$R^{11a}$, —S(O)$_2$N($R^{10a}$)$R^{11a}$, —SC(=Y)R$^{10a}$, —SC(=Y)OR$^{10a}$, —SC(=Y)N($R^{10a}$)$R^{11a}$, —S(O)$_2$R$^{10a}$, —SR$^{10a}$, —S(O)R$^{10a}$, —S(O)$_2$OR$^{10a}$, $C_{1-12}$ alkyl, heterocycloalkyl, which latter two groups are optionally substituted by one or more substituents selected from =O, =S, =N($R^{20}$) and $E^1$, aryl or heteroaryl, which latter two groups are optionally substituted by one or more substituents selected from $E^2$;

each $R^{10a}$, $R^{11a}$, and $R^{12a}$ independently represents, on each occasion when used herein,
  hydrogen, $C_{1-12}$ alkyl, heterocycloalkyl, which latter two groups are optionally substituted by one or more substituents selected from =O, =S, =N($R^{20}$) and $E^3$, aryl or heteroaryl, which latter two groups are optionally substituted by one or more substituents selected from $E^4$; or
  any relevant pair of $R^{10a}$, $R^{11a}$ and $R^{12a}$, may be linked together to form a 4- to 20-membered ring, optionally containing one or more heteroatoms, optionally containing one or more unsaturations, and which ring is optionally substituted by one or more substituents selected from =O, =S, =N($R^{20}$) and $E^5$;

each $E^1$, $E^2$, $E^3$, $E^4$ and $E^5$ independently represents, on each occasion when used herein:
  (i) $Q^4$;
  (ii) $C_{1-12}$ alkyl or heterocycloalkyl, both of which are optionally substituted by one or more substituents selected from =O and $Q^5$; or
  (iii) aryl or heteroaryl, both of which are optionally substituted by one or more substituents selected from $Q^6$;

each $Q^4$, $Q^5$ and $Q^6$ independently represents, on each occasion when used herein:
  halogen, —CN, —NO$_2$, —N($R^{20}$)$R^{21}$, —OR$^{20}$, —C(=Y)—R$^{20}$, —C(=Y)—OR$^{20}$, —C(=Y)N($R^{20}$)$R^{21}$, —OC(=Y)—R$^{20}$, —OC(=Y)—OR$^{20}$, —OC(=Y)N($R^{20}$)$R^{21}$, —OS(O)$_2$OR$^{20}$, —OP(=Y)(OR$^{20}$)(OR$^{21}$), —OP(OR$^{20}$)(OR$^{21}$), —N($R^{22}$)C(=Y)$R^{21}$, —N($R^{22}$)C(=Y)OR$^{21}$, —N($R^{22}$)C(=Y)N($R^{20}$)$R^{21}$, —NR$^{22}$S(O)$_2$R$^{20}$, —NR$^{22}$S(O)$_2$N($R^{20}$)$R^{21}$, —S(O)$_2$N($R^{20}$)$R^{21}$, —SC(=Y)R$^{20}$, —SC(=Y)OR$^{20}$, —SC(=Y)N($R^{20}$)$R^{21}$, —S(O)$_2$R$^{20}$, —SR$^{20}$, —S(O)R$^{20}$, —S(O)$_2$OR$^{20}$, $C_{1-12}$ alkyl, heterocycloalkyl, which latter two groups are optionally substituted by one or more substituents selected from =O and $J^1$, aryl or heteroaryl, which latter two groups are optionally substituted by one or more substituents selected from $J^2$;

each Y independently represents, on each occasion when used herein, =O, =S or =NR$^{23}$;

each $R^{20}$, $R^{21}$, $R^{22}$ and $R^{23}$ independently represents, on each occasion when used herein,
  hydrogen, $C_{1-6}$ alkyl, heterocycloalkyl, which latter two groups are optionally substituted by one or more substituents selected from $J^3$ and =O, aryl or heteroaryl, which latter two groups are optionally substituted by one or more substituents selected from $J^4$; or any relevant pair of $R^{20}$, $R^{21}$ and $R^{22}$, may be linked together to form a 4- to 20-membered ring, optionally containing one or more heteroatoms, optionally containing one or more unsaturations, and which ring is optionally substituted by one or more substituents selected from $J^5$ and =O;

each $J^1$, $J^2$, $J^3$, $J^4$ and $J^5$ independently represents, on each occasion when used herein:
(i) $Q^7$;
(ii) $C_{1-6}$ alkyl or heterocycloalkyl, both of which are optionally substituted by one or more substituents selected from =O and $Q^8$; or
(iii) aryl or heteroaryl, both of which are optionally substituted by one or more substituents selected from $Q^9$;

each $Q^7$, $Q^8$ and $Q^9$ independently represents, on each occasion when used herein:
halogen, —CN, —N($R^{50}$)$R^{51}$, —O$R^{50}$, —C(=$Y^a$)—$R^{50}$, —C(=$Y^a$)—O$R^{50}$, —C(=$Y^a$)N($R^{50}$)$R^{51}$, —N($R^{52}$)C(=$Y^a$)$R^{51}$, —N$R^{52}$S(O)$_2R^{50}$, —S(O)$_2$$R^{50}$, —S$R^{50}$, —S(O)$R^{50}$ or $C_{1-6}$ alkyl optionally substituted by one or more fluoro atoms;

each $Y^a$ independently represents, on each occasion when used herein, =O, =S, =N$R^{53}$;

each $R^{50}$, $R^{51}$, $R^{52}$ and $R^{53}$ independently represents, on each occasion when used herein,
hydrogen or
$C_{1-6}$ alkyl optionally substituted by one or more substituents selected from fluoro, —O$R^{60}$ and —N($R^{61}$)$R^{62}$; or any relevant pair of $R^{50}$, $R^{51}$ and $R^{52}$ may be linked together to form, a 3- to 8-membered ring, optionally containing one or more heteroatoms, optionally containing one or more unsaturations, and which ring is optionally substituted by one or more substituents selected from =O and $C_{1-3}$ alkyl;

$R^{60}$, $R^{61}$ and $R^{62}$ independently represent hydrogen or $C_{1-6}$ alkyl optionally substituted by one or more fluoro atoms;

or a pharmaceutically acceptable ester, amide, solvate or salt thereof.

2. A compound as claimed in claim 1, wherein, $R^1$ represents phenyl substituted with one or more substituents selected from $A^1$; or $R^1$ represents heteroaryl optionally substituted with one or more substituents selected from $A^2$.

3. A compound as claimed in claim 1, wherein the aromatic groups defined by $R^1$ and/or $R^3$ are substituted.

4. A compound as claimed in claim 1, wherein $R^1$ and/or $R^3$ are substituted with one or two substituents located at the para and/or meta position.

5. A compound as claimed in claim 1, wherein:
$A^1$, $A^2$ and $A^4$ independently represent $Q^1$ or may alternatively represent $C_{1-6}$ alkyl or heterocycloalkyl, both of which are optionally substituted by one or more $Q^2$ substituents;

each $Q^1$, $Q^2$ and $Q^3$ independently represents
$C_{1-6}$ alkyl, optionally substituted by one or more fluoro atoms, a 5- or 6-membered heterocycloalkyl group, optionally substituted by one or more substitutents selected from $E^1$, —S$R^{10a}$, —S(O)$R^{10a}$, —N$R^{12a}$S(O)$_2R^{10a}$, —C(=Y)—N($R^{10a}$)$R^{11a}$, —S(O)$_2$N($R^{10a}$)$R^{11a}$, —N($R^{12a}$)C(=Y)$R^{11a}$, halogen, —CN, —O$R^{10a}$, —N($R^{10a}$)$R^{11a}$, —C(=Y)O$R^{10a}$ or —S(O)$_2R^{10a}$, —CN, —O$R^{10a}$, —N($R^{10a}$)$R^{11a}$, —C(=Y)O$R^{10a}$ or —S(O)$_2R^{10a}$);

$Q^2$ represents halo, —N$R^{12a}$S(O)$_2R^{10a}$, $C_{1-6}$ alkyl, optionally substituted by one or more fluoro atoms, or —C(=Y)O$R^{10a}$;

each $R^{10a}$, $R^{11a}$ and $R^{12a}$ independently represents
hydrogen, $C_{1-3}$ alkyl or heterocycloalkyl, which latter two groups are optionally substituted by one or more substituents selected from $E^3$; or
$R^{10a}$ may represent aryl or heteroaryl; or
$R^{10a}$ and $R^{11a}$ may be linked together to form a 5- or 6-membered ring optionally containing one further heteroatom, which ring may be substituted by one or more $E^5$ substituents; or
$R^{12a}$ represents $C_{1-3}$ alkyl or hydrogen;

each $E^1$, $E^2$, $E^3$, $E^4$ and $E^5$ independently represent
$C_{1-6}$ alkyl, heterocycloalkyl, which latter two groups are optionally substituted by one or more substituents selected from =O and $Q^5$;

each $Q^4$, $Q^5$ and $Q^6$ independently represent
halogen, —C(=Y)—O$R^{20}$, —N($R^{20}$)$R^{21}$, —C(=Y)N($R^{20}$)$R^{21}$ or —N($R^{22}$)C(=Y)O$R^{21}$;

each Y independently represents =O;

$R^{20}$ and $R^{21}$ independently represent
hydrogen or $C_{1-4}$ alkyl; or
$R^{20}$ and $R^{21}$, when attached to the same nitrogen atom are linked together to form a 5- or 6-membered ring, optionally containing a further heteroatom; and/or
$R^{22}$ represents hydrogen.

6. A pharmaceutical formulation comprising a compound of claim 1, or a pharmaceutically acceptable ester, amide, solvate or salt thereof, in admixture with a pharmaceutically acceptable adjuvant, diluent or carrier.

7. A method of treatment of a cancer in which inhibition of a PI3-Kα is desired and/or required, which method comprises administration of a therapeutically effective amount of a compound according to claim 1, or a pharmaceutically-acceptable ester, amide, solvate or salt thereof, to a patient suffering from, or susceptible to, such a condition.

8. A combination product comprising:
(A) a compound according to claim 1, or a pharmaceutically-acceptable ester, amide, solvate or salt thereof; and
(B) another therapeutic agent that is useful in the treatment of cancer and/or a proliferative disease,
wherein each of components (A) and (B) is formulated in admixture with a pharmaceutically-acceptable adjuvant, diluent or carrier.

9. A process for the preparation of a compound of formula I as defined in claim 1, which process comprises:
reaction of a corresponding compound of formula II,

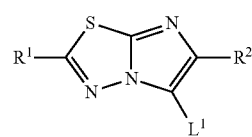

II wherein $L^1$ represents a suitable leaving group, and $R^1$ and $R^2$ are as defined in claim 1, with a compound of formula III, $L^2$—$R^3$                III wherein $L^2$ represents a suitable group, and $R^3$ is as defined in claim 1.

10. A process for the preparation of a pharmaceutical formulation comprising a compound of claim 1, or a pharmaceutically acceptable ester, amide, solvate or salt thereof, in admixture with a pharmaceutically acceptable adjuvant, diluent or carrier, which process comprises bringing into association a compound of claim 1, or a pharmaceutically acceptable ester, amide, solvate or salt thereof with a pharmaceutically-acceptable adjuvant, diluent or carrier.

11. A process for the preparation of a combination product comprising:
   (A) a compound according to claim 1, or a pharmaceutically-acceptable ester, amide, solvate or salt thereof; and
   (B) another therapeutic agent that is useful in the treatment of in the treatment of cancer and/or a proliferative disease,
   wherein each of components (A) and (B) is formulated in admixture with a pharmaceutically-acceptable adjuvant, diluent or carrier
   which process comprises bringing into association a compound according to claim 1, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

12. A compound as claimed in claim 1, selected from the group consisting of:

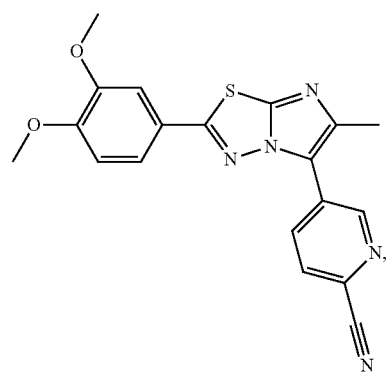

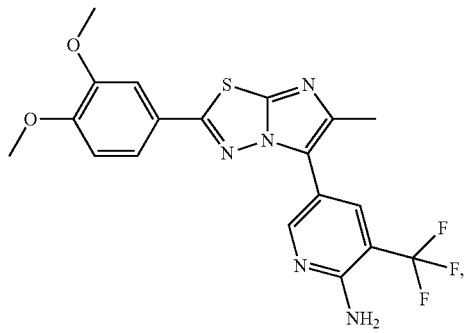

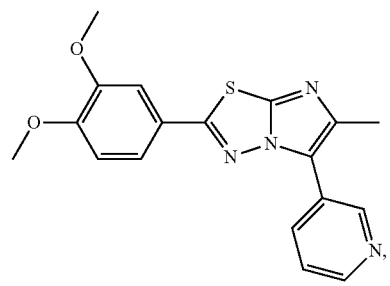

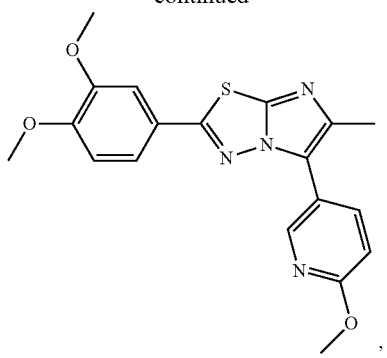

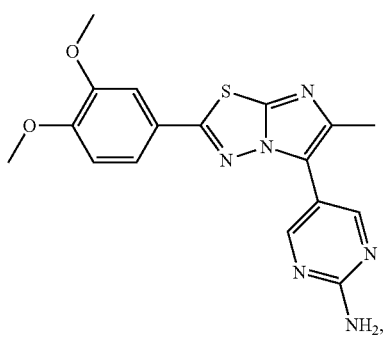

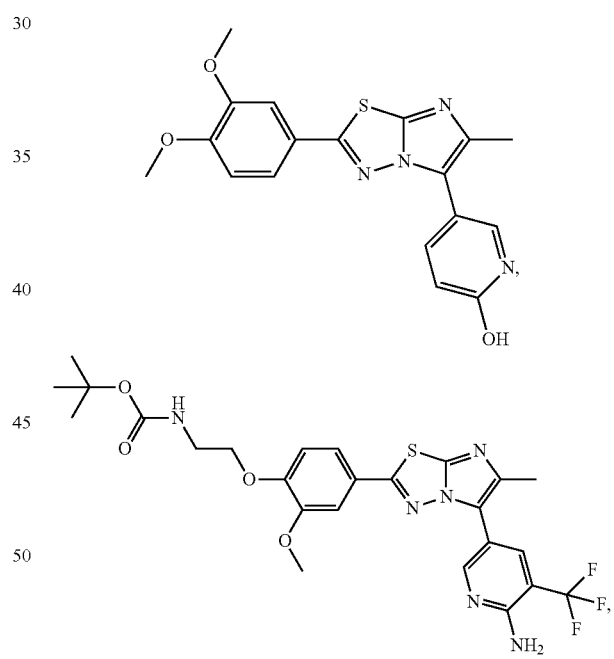

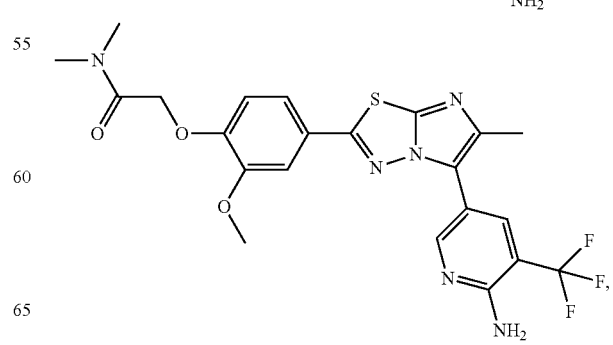

87
-continued
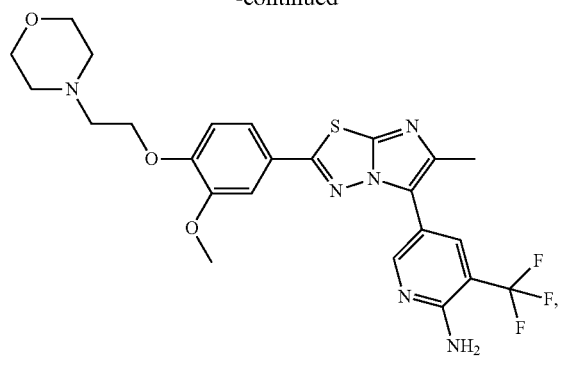
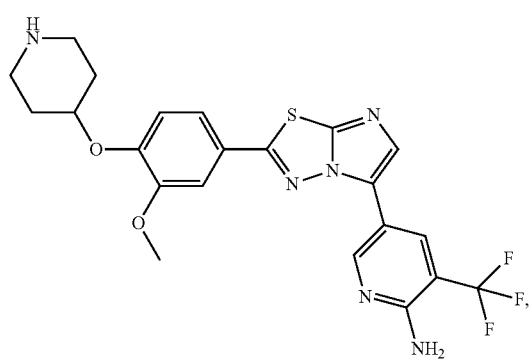
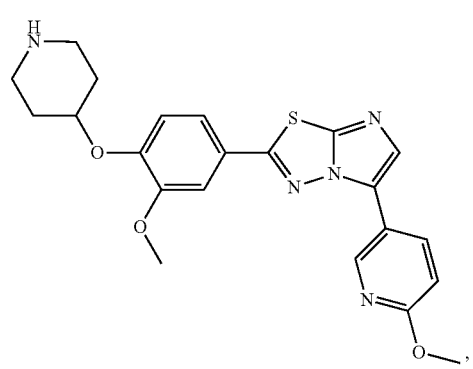
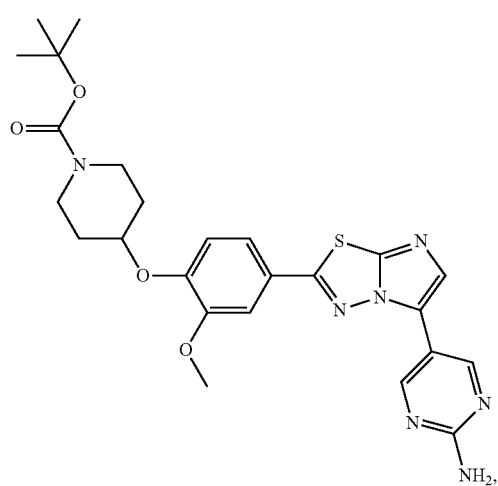
88
-continued
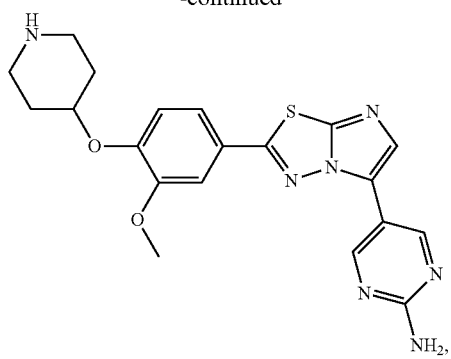
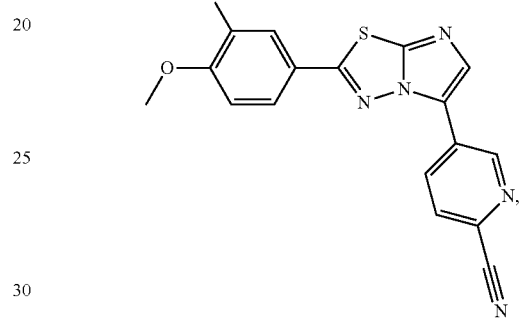
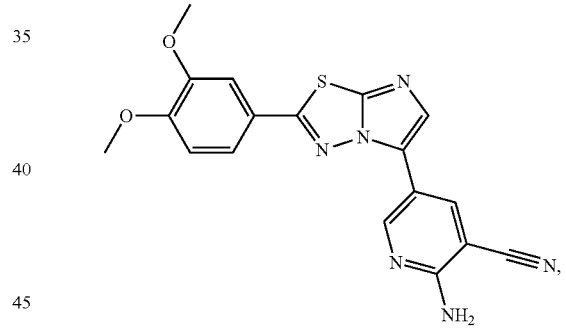
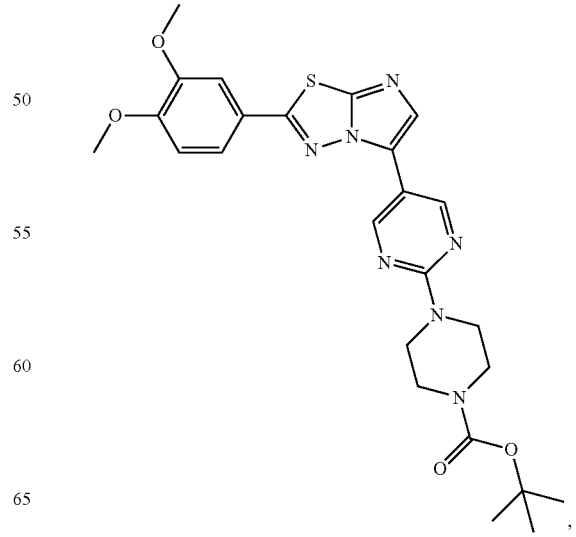

89
-continued
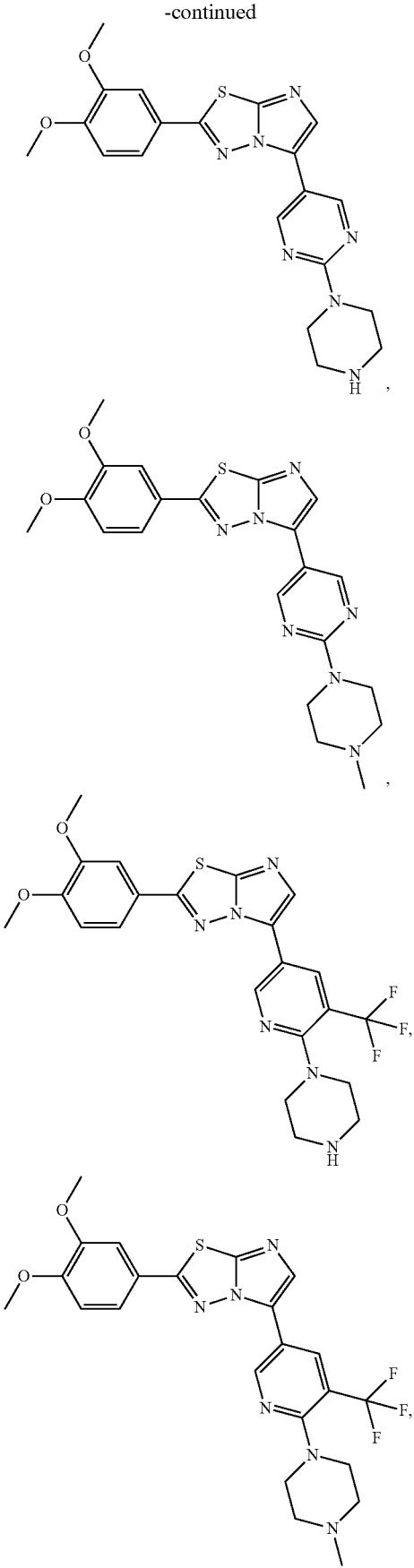
90
-continued
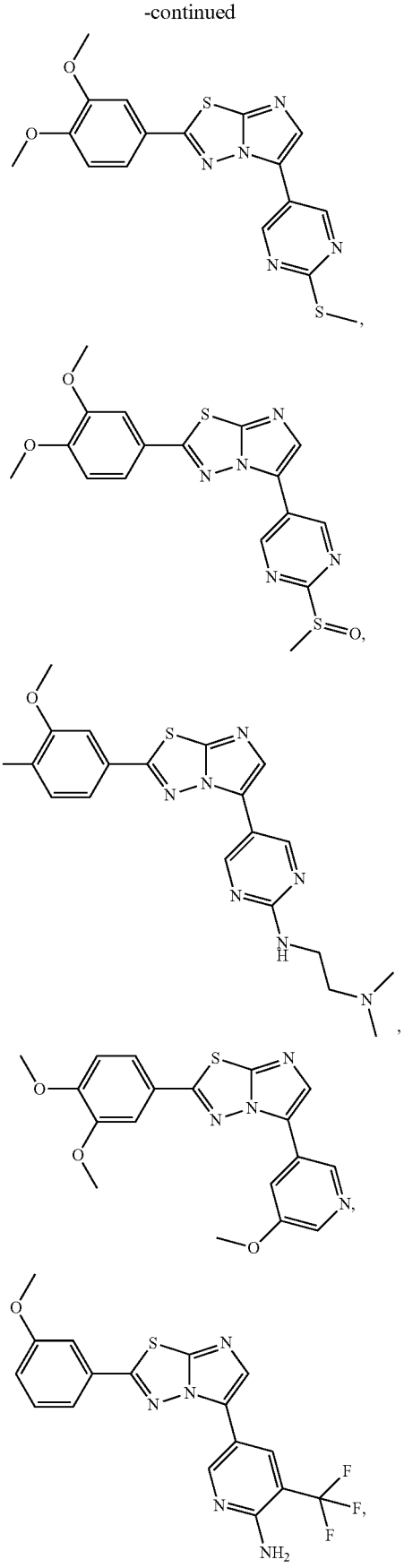

91
-continued
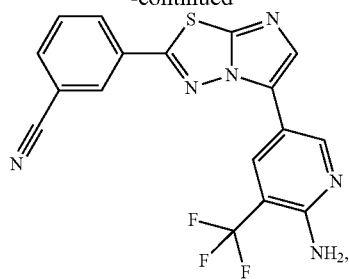
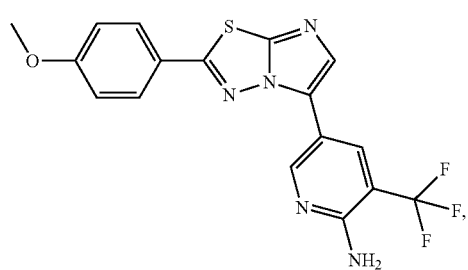
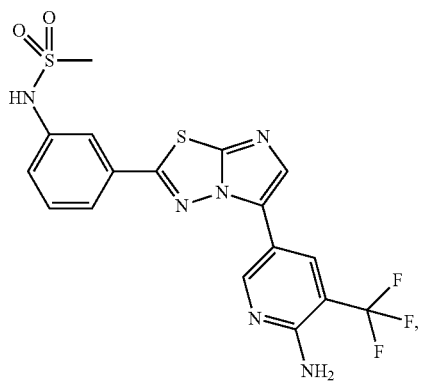
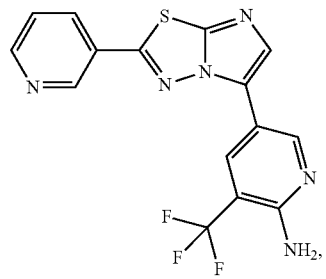
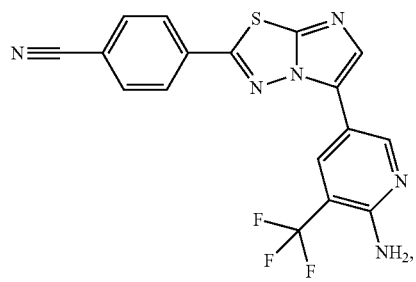
92
-continued
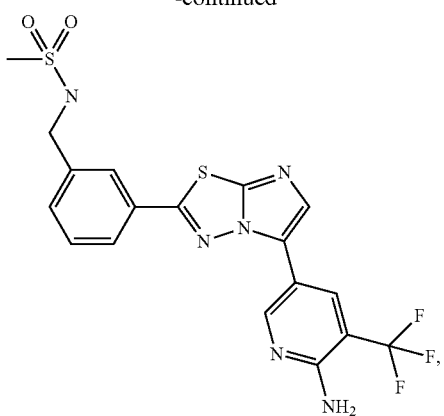
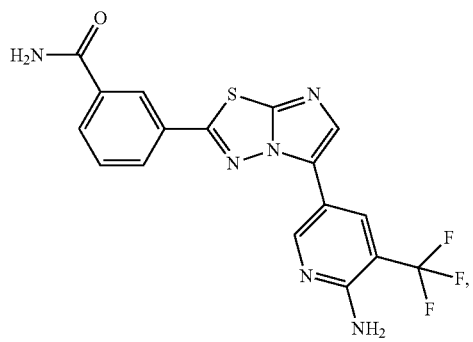
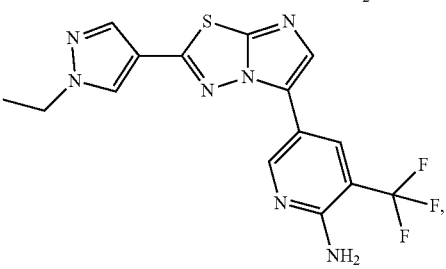
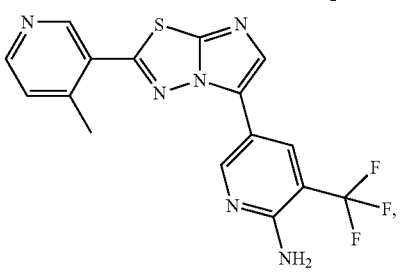
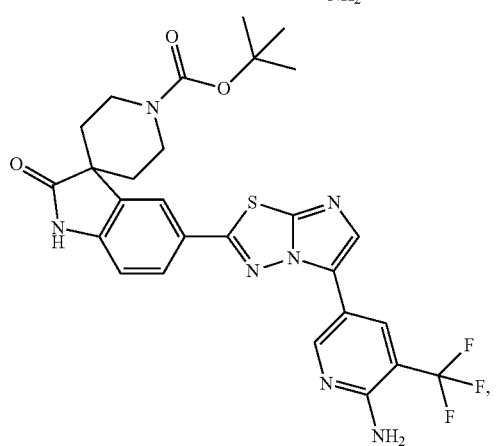

93
-continued
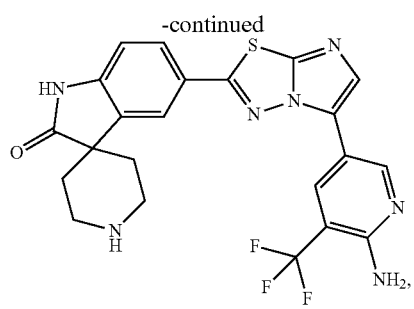
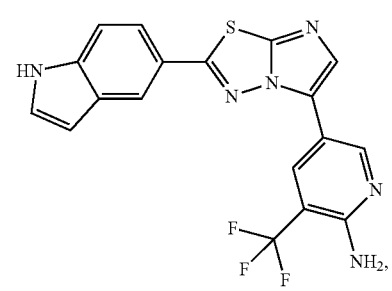
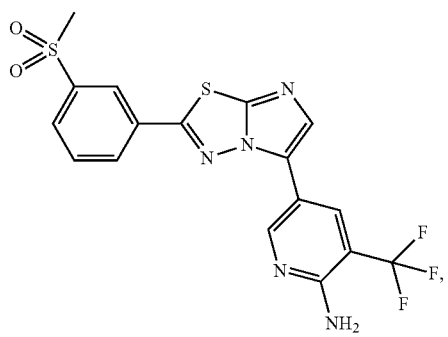
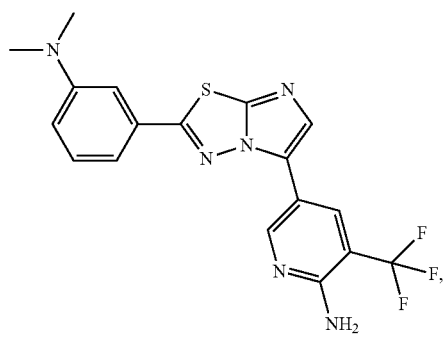
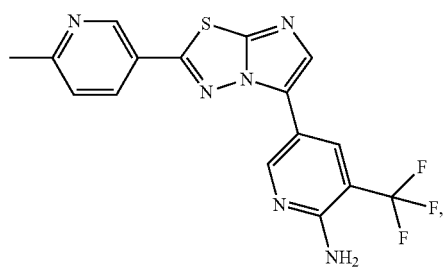
94
-continued
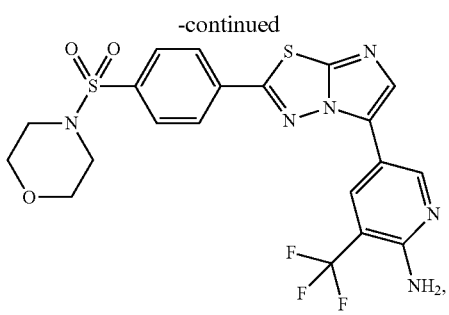
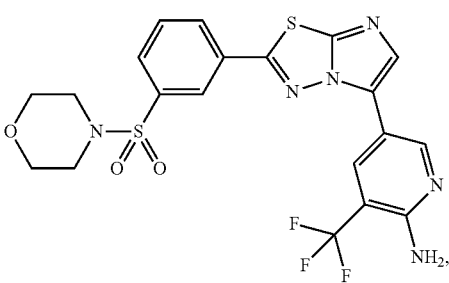
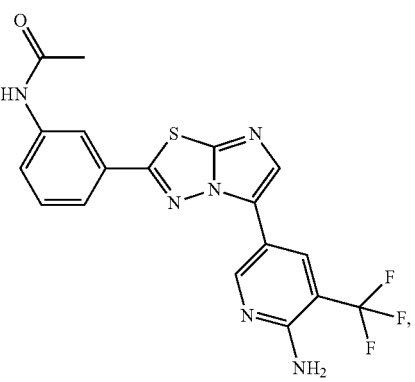
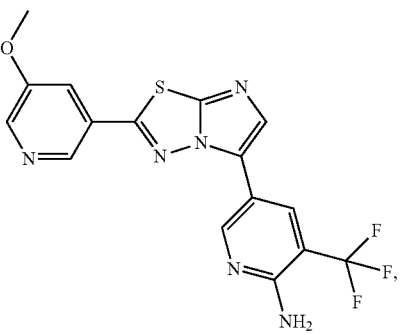
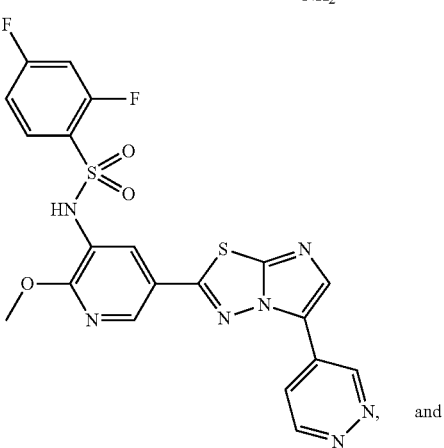
and -continued or a pharmaceutically acceptable ester, amide, solvate or salt thereof.

13. A compound selected from the group consisting of:

-continued or a pharmaceutically acceptable ester, amide, solvate or salt thereof.

14. A pharmaceutical formulation comprising a compound of claim 13, or a pharmaceutically acceptable ester, amide, solvate or salt thereof, in admixture with a pharmaceutically acceptable adjuvant, diluent or carrier.

15. A method of treatment of a cancer in which inhibition of a PI3-Kα is desired and/or required, said method comprising administration of a therapeutically effective amount of a compound according to claim 13, or a pharmaceutically-acceptable ester, amide, solvate or salt thereof, to a patient suffering from, or susceptible to, such a condition.

16. A combination product comprising:

(A) a compound according to claim 13, or a pharmaceutically-acceptable ester, amide, solvate or salt thereof; and (B) another therapeutic agent that is useful in the treatment of cancer and/or a proliferative disease, wherein each of components (A) and (B) is formulated in admixture with a pharmaceutically-acceptable adjuvant, diluent or carrier.

17. A process for the preparation of a compound of claim 13, or a pharmaceutically acceptable ester, amide, solvate or salt thereof, said process comprising: reaction of a compound of formula II,

II $R^1$—[structure]—$R^2$, $L^1$ with a compound of formula III $L^2$—$R^3$    III, wherein
R³ is selected from the group consisting of

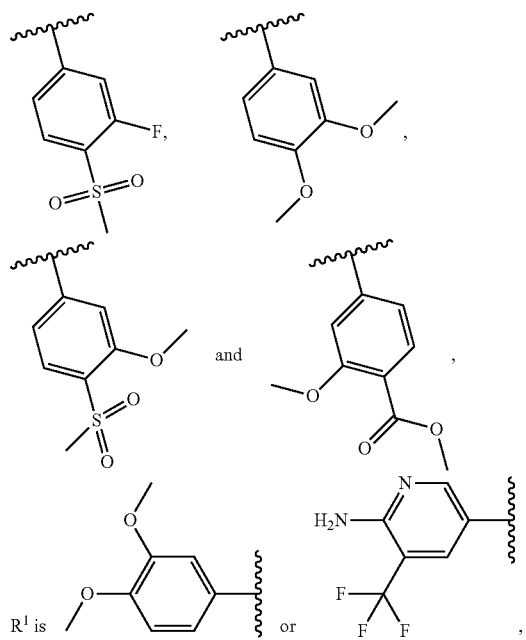

R² is hydrogen or methyl,
L¹ and L² independently represents a suitable leaving group.

18. A process for the preparation of a pharmaceutical formulation comprising a compound of claim 13, or a pharmaceutically acceptable ester, amide, solvate or salt thereof, in admixture with a pharmaceutically acceptable adjuvant, diluent or carrier, said process comprising bringing into association a compound of claim 13, or a pharmaceutically acceptable ester, amide, solvate or salt thereof with a pharmaceutically-acceptable adjuvant, diluent or carrier.

19. A process for the preparation of a combination product comprising:
   (A) a compound according to claim 13, or a pharmaceutically-acceptable ester, amide, solvate or salt thereof; and
   (B) another therapeutic agent that is useful in the treatment of cancer and/or a proliferative disease,
   wherein each of components (A) and (B) is formulated in admixture with a pharmaceutically-acceptable adjuvant, diluent or carrier,
   said process comprising bringing into association a compound according to claim 13, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

* * * * *

UNITED STATES PATENT AND TRADEMARK OFFICE
CERTIFICATE OF CORRECTION

PATENT NO. : 8,815,918 B2  
APPLICATION NO. : 13/262183  
DATED : August 26, 2014  
INVENTOR(S) : Joaquin Pastor Fernández et al.

Page 1 of 1

It is certified that error appears in the above-identified patent and that said Letters Patent is hereby corrected as shown below:

In the Claims:

In Claim 17, at column 97, lines 13-21, please replace the chemical structure with -- 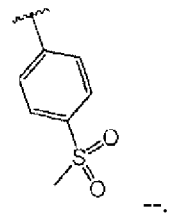 --.

Signed and Sealed this  
Twenty-fourth Day of March, 2015

Michelle K. Lee  
*Director of the United States Patent and Trademark Office*

UNITED STATES PATENT AND TRADEMARK OFFICE
CERTIFICATE OF CORRECTION

PATENT NO.         : 8,815,918 B2                          Page 1 of 1
APPLICATION NO.    : 13/262183
DATED              : August 26, 2014
INVENTOR(S)        : Joaquín Pastor Fernández et al.

It is certified that error appears in the above-identified patent and that said Letters Patent is hereby corrected as shown below:

On the title page, column 1: Delete "(73) Assignee: Centro Nacional de Investigaciones Oncologicas (CNIO)" and replace it with --(73) Assignee: Fundacion Centro Nacional de Investigaciones Oncologicas Carlos III--

Signed and Sealed this
Twenty-seventh Day of October, 2015

Michelle K. Lee
*Director of the United States Patent and Trademark Office*